(12) United States Patent
Grininger et al.

(10) Patent No.: US 11,078,468 B2
(45) Date of Patent: Aug. 3, 2021

(54) MICROBIOLOGICAL PRODUCTION OF SHORT FATTY ACIDS AND USES THEREOF

(71) Applicant: Johann Wolfgang Goethe-Universität Frankfurt am Main, Frankfurt am Main (DE)

(72) Inventors: Martin Grininger, Frankfurt (DE); Jan Gajewski, Frankfurt (DE); Eckhard Boles, Darmstadt (DE); Renata Pavlovic, Zedge (SG)

(73) Assignee: Johann Wolfgang Goethe-Universität Frankfurt am Main, Frankfurt am Main (DE)

( * ) Notice: Subject to any disclaimer, the term of this patent is extended or adjusted under 35 U.S.C. 154(b) by 0 days.

(21) Appl. No.: 15/561,201

(22) PCT Filed: Mar. 31, 2016

(86) PCT No.: PCT/EP2016/057167
§ 371 (c)(1),
(2) Date: Sep. 25, 2017

(87) PCT Pub. No.: WO2016/156548
PCT Pub. Date: Oct. 6, 2016

(65) Prior Publication Data
US 2018/0066240 A1    Mar. 8, 2018

(30) Foreign Application Priority Data
Apr. 1, 2015   (EP) ..................................... 15162192

(51) Int. Cl.
*C12N 9/10*   (2006.01)
*C12P 7/64*   (2006.01)
(Continued)

(52) U.S. Cl.
CPC ........... *C12N 9/1029* (2013.01); *C12N 15/82* (2013.01); *C12P 7/04* (2013.01); *C12P 7/6409* (2013.01);
(Continued)

(58) Field of Classification Search
None
See application file for complete search history.

(56) References Cited
U.S. PATENT DOCUMENTS
2009/0049572 A1   2/2009   Voelker et al.

FOREIGN PATENT DOCUMENTS
JP   2002027989 A   1/2002
WO   2008000277 A2   1/2008
(Continued)

OTHER PUBLICATIONS
Machine translation of JP2002-027989 (Year: 2002).*
(Continued)

*Primary Examiner* — Rebecca E Prouty
(74) *Attorney, Agent, or Firm* — Saliwanchik, Lloyd & Eisenschenk

(57) ABSTRACT

The present invention relates to proteins involved in fatty acid synthesis, such as fatty acid synthases (FAS) variants, comprising one or more polypeptide chains, wherein said polypeptide chain(s) comprise one or more subunits comprising a malonyl/palmitoyl transferase domain (MPT domain), acetyl transferase domain (AT domain), and ketoacyl synthase domain (KS domain), and at least one amino acid substitution in the MPT domain at a position corresponding to R130, in the AT domain at a position corresponding to I306, and/or in the KS domain, preferably in the acyl binding channel and/or at KS domain binding site to ACP, to modulate affinities of acyl intermediates, and optionally further amino acid substitution(s). The present invention relates to the respective polypeptide domains. The present invention further relates to nucleic acid molecules encoding the proteins (or the polypeptide domains) and to host cells containing said nucleic acid molecules. The present invention further relates to a method for the production of short fatty acids, CoA esters of short fatty acids, ethyl esters of short fatty acids, esters of short fatty acids with other metabolites, and/or enzyme bound short fatty acids ($C_6$ to $C_{12}$), comprising the expression of said nucleic acid molecules, preferably in said host cells. The present invention further relates to a method for the production of biofuels, flavoring compounds and/or fine chemicals, comprising the expression of said nucleic acid molecules, preferably in said host cells. The present invention also relates to the use of the proteins, nucleic acids molecule or host cells for the bulk production of short fatty acids ($C_6$ to $C_{12}$), the specific production of $C_6$ fatty acids and/or C8 fatty acids, the bulk production of CoA esters of short fatty acids ($C_6$ to $C_{12}$), the specific production of $C_6$-CoA esters and/or $C_8$-CoA esters, the bulk production of ethyl esters of short fatty acids ($C_6$ to $C_{12}$), the specific production of $C_6$ fatty acid ethyl esters and/or $C_8$ fatty acid ethyl esters, the bulk production of esters of short fatty acids ($C_6$ to $C_{12}$) with other metabolites, the specific production of $C_6$ fatty acid esters with other metabolites and/or $C_8$ fatty acid esters with other metabolites, the bulk production of enzyme bound short fatty acids ($C_6$ to $C_{12}$), the specific production of enzyme bound $C_6$ fatty acids and/or enzyme bound $C_8$ fatty acids, the production of biofuels, fine chemicals and/or flavoring substances.

4 Claims, 17 Drawing Sheets
Specification includes a Sequence Listing.

(51) Int. Cl.
*C12P 7/04* (2006.01)
*C12N 15/82* (2006.01)

(52) U.S. Cl.
CPC ............ *C12P 7/649* (2013.01); *C12P 7/6436* (2013.01); *Y02E 50/10* (2013.01)

(56) References Cited

FOREIGN PATENT DOCUMENTS

WO    2010117274  A1    10/2010
WO    2014202616  A2    12/2014

OTHER PUBLICATIONS

I.B. Lomakin et al. "The Crystal Structure of Yeast Fatty Acid Synthase, a Cellular Machine with Eight Active Sites Working Together", Cell 129:319-332. (Year: 2007).*

V.S. Rangan et al. "Alteration of the Substrate Specificity of the Malonyl-CoA/Acetyl-CoA:Acyl Carrier Protein S-Acyltransferase Domain of the Multifunctional Fatty Acid Synthase by Mutation of a Single Arginine Residue", J. biol. Chem. 272(18): 11975-11978 (Year: 1997).*

* cited by examiner

SEQUENCE LISTING

```
<160> NUMBER OF SEQ ID NOS: 30

<210> SEQ ID NO 1
<211> LENGTH: 429
<212> TYPE: PRT
<213> ORGANISM: Saccharomyces cerevisiae

<400> SEQUENCE: 1

Ser Ile Leu Asp Ile Val Ile Asn Asn Pro Val Asn Leu Thr Ile His
1               5                   10                  15

Phe Gly Glu Lys Gly Lys Arg Ile Arg Glu Asn Tyr Ser Ala Met
            20                  25                  30

Ile Phe Glu Thr Ile Val Asp Gly Lys Leu Lys Thr Glu Lys Ile Phe
        35                  40                  45

Lys Glu Ile Asn Glu His Ser Thr Ser Tyr Thr Phe Arg Ser Glu Lys
    50                  55                  60

Gly Leu Leu Ser Ala Thr Gln Phe Thr Gln Pro Ala Leu Thr Leu Met
65                  70                  75                  80

Glu Lys Ala Ala Phe Glu Asp Leu Lys Ser Lys Gly Leu Ile Pro Ala
                85                  90                  95

Asp Ala Thr Phe Ala Gly His Ser Leu Gly Glu Tyr Ala Ala Leu Ala
            100                 105                 110

Ser Leu Ala Asp Val Met Ser Ile Glu Ser Leu Val Glu Val Val Phe
        115                 120                 125

Tyr Arg Gly Met Thr Met Gln Val Ala Val Pro Arg Asp Glu Leu Gly
    130                 135                 140

Arg Ser Asn Tyr Gly Met Ile Ala Ile Asn Pro Gly Arg Val Ala Ala
145                 150                 155                 160

Ser Phe Ser Gln Glu Ala Leu Gln Tyr Val Val Glu Arg Val Gly Lys
                165                 170                 175
```

Arg Thr Gly Trp Leu Val Glu Ile Val Asn Tyr Asn Val Glu Asn Gln
            180                 185                 190

Gln Tyr Val Ala Ala Gly Asp Leu Arg Ala Leu Asp Thr Val Thr Asn
            195                 200                 205

Val Leu Asn Phe Ile Lys Leu Gln Lys Ile Asp Ile Glu Leu Gln
210                 215                 220

Lys Ser Leu Ser Leu Glu Glu Val Glu Gly His Leu Phe Glu Ile Ile
225                 230                 235                 240

Asp Glu Ala Ser Lys Lys Ser Ala Val Lys Pro Arg Pro Leu Lys Leu
                245                 250                 255

Glu Arg Gly Phe Ala Cys Ile Pro Leu Val Gly Ile Ser Val Pro Phe
            260                 265                 270

His Ser Thr Tyr Leu Met Asn Gly Val Lys Pro Phe Lys Ser Phe Leu
            275                 280                 285

Lys Lys Asn Ile Ile Lys Glu Asn Val Lys Val Ala Arg Leu Ala Gly
290                 295                 300

Lys Tyr Ile Pro Asn Leu Thr Ala Lys Pro Phe Gln Val Thr Lys Glu
305                 310                 315                 320

Tyr Phe Gln Asp Val Tyr Asp Leu Thr Gly Ser Glu Pro Ile Lys Glu
                325                 330                 335

Ile Ile Asp Asn Trp Glu Lys Tyr Glu Gln Ser Met Lys Pro Glu Val
            340                 345                 350

Glu Gln Glu Leu Ala His Ile Leu Leu Thr Glu Leu Leu Ala Tyr Gln
            355                 360                 365

Phe Ala Ser Pro Val Arg Trp Ile Glu Thr Gln Asp Val Phe Leu Lys
370                 375                 380

Asp Phe Asn Thr Glu Arg Val Val Glu Ile Gly Pro Ser Pro Thr Leu
385                 390                 395                 400

Ala Gly Met Ala Gln Arg Thr Leu Lys Asn Lys Tyr Glu Ser Tyr Asp
                405                 410                 415

Ala Ala Leu Ser Leu His Arg Glu Ile Leu Cys Tyr Ser
            420                 425

<210> SEQ ID NO 2
<211> LENGTH: 551
<212> TYPE: PRT
<213> ORGANISM: Saccharomyces cerevisiae

<400> SEQUENCE: 2

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
            20                  25                  30

Leu Gln Glu Gln Phe Asn Lys Ile Leu Pro Glu Pro Thr Glu Gly Phe
        35                  40                  45

Ala Ala Asp Asp Glu Pro Thr Thr Pro Ala Glu Leu Val Gly Lys Phe
    50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

```
Ala Arg Ile Met Ala Lys Arg Pro Phe Asp Lys Lys Ser Asn Ser Ala
        130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

Phe Thr Gln Gly Leu Asn Ile Leu Glu Trp Leu Glu Asn Pro Ser Asn
210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
        355                 360                 365

Ser Leu Val Asn Gly Ala Lys Asn Leu Val Val Ser Gly Pro Pro Gln
370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                405                 410                 415

Ser Asn Arg Phe Leu Pro Val Ala Ser Pro Phe His Ser His Leu Leu
            420                 425                 430

Val Pro Ala Ser Asp Leu Ile Asn Lys Asp Leu Val Lys Asn Asn Val
        435                 440                 445

Ser Phe Asn Ala Lys Asp Ile Gln Ile Pro Val Tyr Asp Thr Phe Asp
450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
                485                 490                 495

Lys Ala Thr His Ile Leu Asp Phe Gly Pro Gly Gly Ala Ser Gly Leu
            500                 505                 510

Gly Val Leu Thr His Arg Asn Lys Asp Gly Thr Gly Val Arg Val Ile
        515                 520                 525

Val Ala Gly Thr Leu Asp Ile Asn Pro Asp Asp Tyr Gly Phe Lys
530                 535                 540
```

Gln Glu Ile Phe Asp Val Thr
545                 550

<210> SEQ ID NO 3
<211> LENGTH: 650
<212> TYPE: PRT
<213> ORGANISM: Saccharomyces cerevisiae

<400> SEQUENCE: 3

Leu Glu Arg Val Ile Val Val Thr Gly Phe Ala Glu Val Gly Pro Trp
1               5                   10                  15

Gly Ser Ala Arg Thr Arg Trp Glu Met Glu Ala Phe Gly Glu Phe Ser
                20                  25                  30

Leu Glu Gly Cys Val Glu Met Ala Trp Ile Met Gly Phe Ile Ser Tyr
            35                  40                  45

His Asn Gly Asn Leu Lys Gly Arg Pro Tyr Thr Gly Trp Val Asp Ser
        50                  55                  60

Lys Thr Lys Glu Pro Val Asp Asp Lys Asp Val Lys Ala Lys Tyr Glu
65                  70                  75                  80

Thr Ser Ile Leu Glu His Ser Gly Ile Arg Leu Ile Glu Pro Glu Leu
                85                  90                  95

Phe Asn Gly Tyr Asn Pro Glu Lys Lys Glu Met Ile Gln Glu Val Ile
            100                 105                 110

Val Glu Glu Asp Leu Glu Pro Phe Glu Ala Ser Lys Glu Thr Ala Glu
        115                 120                 125

Gln Phe Lys His Gln His Gly Asp Lys Val Asp Ile Phe Glu Ile Pro
130                 135                 140

Glu Thr Gly Glu Tyr Ser Val Lys Leu Leu Lys Gly Ala Thr Leu Tyr
145                 150                 155                 160

Ile Pro Lys Ala Leu Arg Phe Asp Arg Leu Val Ala Gly Gln Ile Pro
                165                 170                 175

Thr Gly Trp Asn Ala Lys Thr Tyr Gly Ile Ser Asp Asp Ile Ile Ser
            180                 185                 190

Gln Val Asp Pro Ile Thr Leu Phe Val Leu Val Ser Val Glu Ala
        195                 200                 205

Phe Ile Ala Ser Gly Ile Thr Asp Pro Tyr Glu Met Tyr Lys Tyr Val
210                 215                 220

His Val Ser Glu Val Gly Asn Cys Ser Gly Ser Gly Met Gly Gly Val
225                 230                 235                 240

Ser Ala Leu Arg Gly Met Phe Lys Asp Arg Phe Lys Asp Glu Pro Val
                245                 250                 255

Gln Asn Asp Ile Leu Gln Glu Ser Phe Ile Asn Thr Met Ser Ala Trp
            260                 265                 270

Val Asn Met Leu Leu Ile Ser Ser Gly Pro Ile Lys Thr Pro Val
        275                 280                 285

Gly Ala Cys Ala Thr Ser Val Glu Ser Val Asp Ile Gly Val Glu Thr
        290                 295                 300

Ile Leu Ser Gly Lys Ala Arg Ile Cys Ile Val Gly Gly Tyr Asp Asp
305                 310                 315                 320

Phe Gln Glu Glu Gly Ser Phe Gly Phe Gly Asn Met Lys Ala Thr Ser
                325                 330                 335

Asn Thr Leu Glu Glu Phe Glu His Gly Arg Thr Pro Ala Glu Met Ser
            340                 345                 350

Arg Pro Ala Thr Thr Thr Arg Asn Gly Phe Met Glu Ala Gln Gly Ala
        355                 360                 365

Gly Ile Gln Ile Ile Met Gln Ala Asp Leu Ala Leu Lys Met Gly Val
    370                 375                 380

Pro Ile Tyr Gly Ile Val Ala Met Ala Ala Thr Ala Thr Asp Lys Ile
385                 390                 395                 400

Gly Arg Ser Val Pro Ala Pro Gly Lys Gly Ile Leu Thr Thr Ala Arg
                405                 410                 415

Glu His His Ser Ser Val Lys Tyr Ala Ser Pro Asn Leu Asn Met Lys
                420                 425                 430

Tyr Arg Lys Arg Gln Leu Val Thr Arg Glu Ala Gln Ile Lys Asp Trp
            435                 440                 445

Val Glu Asn Glu Leu Glu Ala Leu Lys Leu Glu Ala Glu Glu Ile Pro
    450                 455                 460

Ser Glu Asp Gln Asn Glu Phe Leu Leu Glu Arg Thr Arg Glu Ile His
465                 470                 475                 480

Asn Glu Ala Glu Ser Gln Leu Arg Ala Ala Gln Gln Gln Trp Gly Asn
                485                 490                 495

Asp Phe Tyr Lys Arg Asp Pro Arg Ile Ala Pro Leu Arg Gly Ala Leu
                500                 505                 510

Ala Thr Tyr Gly Leu Thr Ile Asp Asp Leu Gly Val Ala Ser Phe His
            515                 520                 525

Gly Thr Ser Thr Lys Ala Asn Asp Lys Asn Glu Ser Ala Thr Ile Asn
    530                 535                 540

Glu Met Met Lys His Leu Gly Arg Ser Glu Gly Asn Pro Val Ile Gly
545                 550                 555                 560

Val Phe Gln Lys Phe Leu Thr Gly His Pro Lys Gly Ala Ala Gly Ala
                565                 570                 575

Trp Met Met Asn Gly Ala Leu Gln Ile Leu Asn Ser Gly Ile Ile Pro
                580                 585                 590

Gly Asn Arg Asn Ala Asp Asn Val Asp Lys Ile Leu Glu Gln Phe Glu
            595                 600                 605

Tyr Val Leu Tyr Pro Ser Lys Thr Leu Lys Thr Asp Gly Val Arg Ala
    610                 615                 620

Val Ser Ile Thr Ser Phe Gly Phe Gly Gln Lys Gly Gly Gln Ala Ile
625                 630                 635                 640

Val Val His Pro Asp Tyr Leu Tyr Gly Ala
                645                 650

<210> SEQ ID NO 4
<211> LENGTH: 1287
<212> TYPE: DNA
<213> ORGANISM: Saccharomyces cerevisiae

<400> SEQUENCE: 4
tctatcttag acattgtcat taacaaccca gttaacttaa caattcactt cggtggtgaa    60
aagggtaaga ggatcagaga aaactattct gctatgatct ttgagactat cgtggatgga   120
aaattgaaga ctgaaaaaat tttcaaggaa attaatgagc acagtacttc ttacacattt   180
agatctgaaa aaggtttatt gtctgctact caatttacac aaccagcttt aactttgatg   240
gaaaaagctg cttttcgaaga cttgaaatct aaaggtttga tcccagccga tgctactttt   300
gctggtcact cttaggtga gtatgctgct ttggcctctt tggctgatgt tatgtctatc   360
gaatctttag ttgaagttgt gttctacaga ggtatgacta tgcaagttgc tgttccaaga   420
gatgagttgg gcagatccaa ctatggtatg attgccatta acccaggtag agtcgctgca   480

```
tcattctctc aagaagcttt gcaatatgtt gttgagagag ttggtaagag aaccggctgg      540
ttggttgaaa tcgtcaacta caacgttgaa aaccaacaat atgttgcagc tggtgatcta      600
agagctttag acaccgttac caatgttcta aacttcatca aattacaaaa aattgatatt      660
attgaactac aaaagtcctt atctttggaa gaagttgaag gtcatttgtt tgagatcatt      720
gacgaagctt ccaagaaatc tgctgtcaag cctcgcccac ttaaattgga gagaggtttt      780
gcttgtatcc cattagttgg tatttctgtt cctttccatt ccacctactt gatgaatggt      840
gttaaaccat tcaagagttt cttgaagaag aatatcataa agaaaatgt gaaggttgct       900
agattggccg aaagtacat tccaaacttg actgcaaaac cattccaggt tactaaggaa        960
tatttccagg acgtttatga tttgactggc tccgaaccta tcaaggaaat catcgacaac     1020
tgggaaaagt atgaacaatc catgaagccg gaagttgagc aagaattagc tcatattttg     1080
ctaactgaat tgttagctta tcaatttgcc tctcctgtga gatggattga aactcaagat    1140
gttttttga aggattttaa cactgaaagg gttgttgaaa tcggtccttc tccaactttg     1200
gctgggatgg ctcaaagaac cttgaagaat aaatacgaat cttacgatgc tgctctgtct    1260
ttacatagag aaatcttatg ctattcg                                         1287
```

<210> SEQ ID NO 5
<211> LENGTH: 1653
<212> TYPE: PRT
<213> ORGANISM: Saccharomyces cerevisiae

<400> SEQUENCE: 5

```
Ala Thr Gly Gly Ala Cys Gly Cys Thr Thr Ala Cys Thr Cys Cys Ala
  1               5                  10                  15
Cys Ala Ala Gly Ala Cys Cys Ala Thr Thr Ala Ala Cys Cys Cys Thr
             20                  25                  30
Ala Thr Cys Thr Cys Ala Cys Gly Gly Thr Cys Thr Thr Thr Ala
         35                  40                  45
Gly Ala Gly Cys Ala Cys Gly Thr Gly Cys Thr Cys Thr Gly Gly
     50                  55                  60
Thr Ala Cys Cys Ala Ala Cys Cys Gly Cys Thr Thr Cys Ala Thr Thr
 65                  70                  75                  80
Thr Thr Thr Cys Ala Thr Thr Gly Cys Thr Thr Cys Gly Cys Ala Ala
             85                  90                  95
Thr Thr Ala Cys Ala Ala Gly Ala Ala Cys Ala Ala Thr Thr Thr Ala
            100                 105                 110
Ala Thr Ala Ala Ala Ala Thr Thr Thr Thr Gly Cys Cys Cys Gly Ala
            115                 120                 125
Ala Cys Cys Cys Ala Cys Thr Gly Ala Ala Gly Gly Thr Thr Thr
        130                 135                 140
Gly Cys Thr Gly Cys Ala Gly Ala Thr Gly Ala Cys Gly Ala Gly Cys
145                 150                 155                 160
Cys Thr Ala Cys Cys Ala Cys Ala Cys Cys Thr Gly Cys Thr Gly Ala
            165                 170                 175
Ala Cys Thr Ala Gly Thr Gly Gly Gly Gly Ala Ala Thr Thr Cys
            180                 185                 190
Cys Thr Thr Gly Gly Cys Thr Ala Cys Gly Thr Ala Cys Thr Thr
        195                 200                 205
Cys Thr Cys Thr Ala Gly Thr Cys Gly Ala Ala Cys Cys Thr Cys
    210                 215                 220
Cys Ala Ala Gly Gly Thr Cys Gly Gly Thr Cys Ala Ala Thr Thr Cys
```

-continued

```
225                 230                 235                 240

Gly Ala Thr Cys Ala Gly Gly Thr Cys Thr Thr Gly Ala Ala Cys Cys
                245                 250                 255

Thr Thr Thr Gly Cys Thr Thr Ala Ala Cys Ala Gly Ala Ala Thr Thr
            260                 265                 270

Thr Gly Ala Ala Ala Ala Cys Thr Gly Thr Thr Ala Thr Thr Thr Ala
        275                 280                 285

Gly Ala Ala Gly Gly Cys Ala Ala Thr Gly Ala Cys Ala Thr Thr Cys
    290                 295                 300

Ala Cys Gly Cys Cys Thr Thr Gly Gly Cys Thr Gly Cys Thr Ala Ala
305                 310                 315                 320

Ala Cys Thr Ala Thr Thr Ala Cys Ala Gly Gly Ala Ala Ala Ala Cys
                325                 330                 335
Gly Ala Cys Ala Cys Ala Ala Cys Thr Thr Thr Ala Gly Thr Gly Ala
            340                 345                 350

Ala Gly Ala Cys Thr Ala Ala Ala Gly Ala Ala Cys Thr Ala Ala Thr
        355                 360                 365

Thr Ala Ala Ala Ala Ala Thr Thr Ala Thr Ala Thr Thr Ala Cys Cys
    370                 375                 380
Gly Cys Cys Ala Gly Ala Ala Thr Ala Ala Thr Gly Gly Cys Thr Ala
385                 390                 395                 400
Ala Gly Ala Gly Ala Cys Cys Ala Thr Thr Thr Gly Ala Cys Ala Ala
                405                 410                 415
Ala Ala Ala Ala Thr Cys Cys Ala Ala Cys Thr Cys Thr Gly Cys Thr
            420                 425                 430

Cys Thr Thr Thr Thr Thr Ala Gly Gly Gly Cys Cys Gly Thr Cys Gly
        435                 440                 445

Gly Cys Gly Ala Gly Gly Gly Thr Ala Ala Cys Gly Cys Ala Cys Ala
    450                 455                 460

Ala Thr Thr Gly Gly Thr Ala Gly Cys Cys Ala Thr Thr Thr Thr Cys
465                 470                 475                 480
Gly Gly Thr Gly Gly Thr Cys Ala Ala Gly Gly Thr Ala Ala Cys Ala
                485                 490                 495
Cys Cys Gly Ala Cys Gly Ala Cys Thr Ala Cys Thr Thr Thr Gly Ala
            500                 505                 510

Ala Gly Ala Ala Thr Thr Gly Cys Gly Thr Gly Ala Thr Cys Thr Ala
        515                 520                 525

Thr Ala Thr Cys Ala Ala Ala Cys Thr Thr Ala Thr Cys Ala Thr Gly
    530                 535                 540
Thr Cys Thr Thr Ala Gly Thr Gly Gly Gly Ala Gly Ala Thr Thr Thr
545                 550                 555                 560

Ala Ala Thr Cys Ala Ala Gly Thr Thr Cys Thr Cys Cys Gly Cys Thr
                565                 570                 575

Gly Ala Ala Ala Cys Thr Thr Thr Ala Ala Gly Thr Gly Ala Ala Cys
            580                 585                 590

Thr Gly Ala Thr Thr Ala Gly Ala Ala Cys Thr Ala Cys Thr Thr Thr
        595                 600                 605

Ala Gly Ala Thr Gly Cys Thr Gly Ala Ala Ala Ala Ala Gly Thr Cys
    610                 615                 620

Thr Thr Thr Ala Cys Thr Cys Ala Ala Gly Gly Thr Thr Thr Ala Ala
625                 630                 635                 640

Ala Cys Ala Thr Ala Thr Thr Gly Gly Ala Ala Thr Gly Gly Thr Thr
                645                 650                 655
```

```
Gly Gly Ala Gly Ala Ala Cys Cys Cys Thr Thr Cys Ala Ala Ala Thr
            660                 665                 670

Ala Cys Cys Cys Cys Ala Gly Ala Cys Ala Ala Gly Gly Ala Cys Thr
        675                 680                 685

Ala Thr Thr Thr Ala Cys Thr Thr Thr Cys Cys Ala Thr Thr Cys Cys
    690                 695                 700

Ala Ala Thr Thr Thr Cys Ala Thr Gly Cys Cys Cys Cys Thr Thr Ala
705                 710                 715                 720

Ala Thr Thr Gly Gly Thr Gly Thr Cys Ala Thr Thr Cys Ala Ala Thr
                725                 730                 735

Thr Gly Gly Cys Thr Cys Ala Cys Thr Ala Cys Gly Thr Ala Gly Thr
            740                 745                 750

Thr Ala Cys Thr Gly Cys Cys Ala Ala Gly Cys Thr Thr Thr Thr Gly
        755                 760                 765

Gly Gly Thr Thr Thr Cys Ala Cys Thr Cys Cys Ala Gly Gly Thr Gly
    770                 775                 780

Ala Gly Thr Thr Ala Ala Gly Ala Thr Cys Thr Thr Ala Cys Thr Thr
785                 790                 795                 800

Ala Ala Ala Ala Gly Gly Thr Gly Cys Thr Ala Cys Ala Gly Gly Thr
                805                 810                 815

Cys Ala Cys Thr Cys Thr Cys Ala Ala Gly Gly Thr Thr Thr Gly Gly
            820                 825                 830

Thr Thr Ala Cys Thr Gly Cys Thr Gly Thr Cys Gly Cys Cys Ala Thr
        835                 840                 845

Ala Gly Cys Thr Gly Ala Gly Ala Cys Gly Gly Ala Thr Thr Cys Cys
    850                 855                 860

Thr Gly Gly Gly Ala Ala Thr Cys Cys Thr Thr Cys Thr Thr Cys Gly
865                 870                 875                 880

Thr Cys Thr Cys Cys Gly Thr Ala Ala Gly Ala Ala Ala Ala Gly Cys
                885                 890                 895

Ala Ala Thr Thr Ala Cys Thr Gly Thr Ala Thr Thr Ala Thr Thr Cys
            900                 905                 910

Thr Thr Cys Ala Thr Cys Gly Gly Thr Gly Thr Thr Cys Gly Thr Thr
        915                 920                 925

Gly Thr Thr Ala Cys Gly Ala Ala Gly Cys Ala Thr Ala Cys Cys Cys
    930                 935                 940

Ala Ala Ala Cys Ala Cys Thr Thr Cys Cys Cys Thr Ala Cys Cys Ala
945                 950                 955                 960

Cys Cys Ala Thr Cys Cys Ala Thr Cys Thr Thr Gly Gly Ala Ala Gly
                965                 970                 975

Ala Thr Thr Cys Cys Thr Thr Gly Gly Ala Ala Ala Ala Cys Ala Ala
            980                 985                 990

Thr Gly Ala Ala Gly Gly Thr Gly  Thr Thr Cys Cys Ala  Thr Cys Thr
        995                 1000                 1005

Cys Cys  Ala Ala Thr Gly Thr  Thr Gly Thr Cys Cys  Ala Thr Thr
    1010                 1015                 1020

Thr Cys  Cys Ala Ala Thr Cys  Thr Ala Ala Cys Thr  Cys Ala Ala
    1025                 1030                 1035

Gly Ala  Ala Cys Ala Ala Gly  Thr Thr Cys Ala Ala  Gly Ala Cys
    1040                 1045                 1050

Thr Ala  Thr Gly Thr Ala Ala  Ala Thr Ala Ala Gly  Ala Cys Thr
    1055                 1060                 1065
```

-continued

```
Ala Ala  Cys Thr Cys Thr Cys  Ala Thr Thr Thr Gly  Cys Cys Ala
    1070                 1075                 1080

Gly Cys  Thr Gly Gly Thr Ala  Ala Ala Cys Ala Ala  Gly Thr Thr
    1085                 1090                 1095

Gly Ala  Ala Ala Thr Thr Thr  Cys Thr Cys Thr Ala  Gly Thr Cys
    1100                 1105                 1110

Ala Ala  Thr Gly Gly Thr Gly  Cys Gly Ala Ala Gly  Ala Ala Thr
    1115                 1120                 1125

Cys Thr  Ala Gly Thr Cys Gly  Thr Ala Thr Cys Gly  Gly Gly Cys
    1130                 1135                 1140

Cys Cys  Ala Cys Cys Ala Cys  Ala Ala Thr Cys Ala  Thr Thr Ala
    1145                 1150                 1155

Thr Ala  Thr Gly Gly Thr Thr  Thr Ala Ala Ala Cys  Thr Thr Gly
    1160                 1165                 1170

Ala Cys  Thr Thr Thr Ala Ala  Gly Ala Ala Ala Gly  Gly Cys Cys
    1175                 1180                 1185

Ala Ala  Gly Gly Cys Cys Cys  Cys Ala Thr Cys Thr  Gly Gly Ala
    1190                 1195                 1200

Cys Thr  Gly Gly Ala Thr Cys  Ala Ala Thr Cys Ala  Ala Gly Ala
    1205                 1210                 1215

Ala Thr  Cys Cys Cys Ala Thr  Thr Cys Ala Gly Cys  Gly Ala Ala
    1220                 1225                 1230

Ala Gly  Ala Ala Ala Ala Thr  Thr Gly Ala Ala Gly  Thr Thr Cys
    1235                 1240                 1245

Thr Cys  Cys Ala Ala Thr Ala  Gly Gly Thr Thr Cys  Thr Thr Ala
    1250                 1255                 1260

Cys Cys  Thr Gly Thr Thr Gly  Cys Ala Thr Cys Ala  Cys Cys Ala
    1265                 1270                 1275

Thr Thr  Cys Cys Ala Thr Thr  Cys Cys Cys Ala Thr  Cys Thr Ala
    1280                 1285                 1290

Thr Thr  Gly Gly Thr Thr Cys  Cys Ala Gly Cys Thr  Thr Cys Ala
    1295                 1300                 1305

Gly Ala  Thr Thr Thr Gly Ala  Thr Thr Ala Ala Cys  Ala Ala Ala
    1310                 1315                 1320

Gly Ala  Cys Thr Thr Ala Gly  Thr Cys Ala Ala Ala  Ala Ala Cys
    1325                 1330                 1335

Ala Ala  Thr Gly Thr Cys Ala  Gly Cys Thr Thr Thr  Ala Ala Cys
    1340                 1345                 1350

Gly Cys  Thr Ala Ala Ala Gly  Ala Thr Ala Thr Thr  Cys Ala Ala
    1355                 1360                 1365

Ala Thr  Cys Cys Cys Cys Gly  Thr Thr Thr Ala Cys  Gly Ala Cys
    1370                 1375                 1380

Ala Cys  Thr Thr Thr Thr Gly  Ala Thr Gly Gly Thr  Thr Cys Ala
    1385                 1390                 1395

Gly Ala  Thr Cys Thr Ala Ala  Gly Ala Gly Thr Cys  Cys Thr Thr
    1400                 1405                 1410

Thr Cys  Ala Gly Gly Thr Thr  Cys Cys Ala Thr Thr  Thr Cys Cys
    1415                 1420                 1425

Gly Ala  Gly Ala Gly Ala Ala  Thr Cys Gly Thr Cys  Gly Ala Cys
    1430                 1435                 1440

Thr Gly  Cys Ala Thr Cys Ala  Thr Thr Ala Gly Ala  Thr Thr Ala
    1445                 1450                 1455

Cys Cys  Thr Gly Thr Cys Ala  Ala Ala Thr Gly Gly  Gly Ala Ala
```

|      |      |      |      | 1460 |      |      |      | 1465 |      |      |      | 1470 |      |
|------|------|------|------|------|------|------|------|------|------|------|------|------|------|

Ala Cys Thr Ala Cys Thr Cys Ala Cys Ala Ala Thr Thr Cys
1475                    1480                  1485

Ala Ala Ala Gly Cys Cys Ala Cys Cys Cys Ala Cys Ala Thr Ala
          1490                  1495                  1500

Thr Thr Ala Gly Ala Cys Thr Thr Gly Gly Thr Cys Cys Ala
1505                    1510                  1515

Gly Gly Thr Gly Gly Ala Gly Cys Thr Thr Cys Gly Gly Thr
1520                    1525                  1530

Thr Thr Ala Gly Gly Thr Gly Thr Thr Thr Ala Ala Cys Cys
1535                    1540                  1545

Cys Ala Thr Cys Gly Thr Ala Ala Thr Ala Ala Ala Gly Ala Thr
          1550                  1555                  1560

Gly Gly Thr Ala Cys Thr Gly Gly Thr Gly Thr Cys Gly Thr
1565                    1570                  1575

Gly Thr Thr Ala Thr Cys Gly Thr Thr Gly Cys Cys Gly Gly Thr
          1580                  1585                  1590

Ala Cys Thr Cys Thr Cys Gly Ala Cys Ala Thr Ala Ala Cys
1595                    1600                  1605

Cys Cys Ala Gly Ala Thr Gly Ala Thr Gly Ala Thr Thr Ala Cys
          1610                  1615                  1620

Gly Gly Ala Thr Thr Cys Ala Ala Gly Cys Ala Ala Gly Ala Ala
1625                    1630                  1635

Ala Thr Cys Thr Thr Thr Gly Ala Thr Gly Thr Ala Cys Thr
1640                    1645                  1650

<210> SEQ ID NO 6
<211> LENGTH: 1950
<212> TYPE: DNA
<213> ORGANISM: Saccharomyces cerevisiae

<400> SEQUENCE: 6

| ttggaaagag | ttattgtagt | taccggtttt | gctgaagtcg | gcccatgggg | ttcggccaga | 60 |
| acaagatggg | aaatggaagc | ttttggtgaa | ttttcgttgg | aaggttgcgt | tgaaatggcc | 120 |
| tggattatgg | gcttcatttc | ataccataac | ggtaatttga | agggtcgtcc | atacactggt | 180 |
| tgggttgatt | ccaaaacaaa | agaaccagtt | gatgacaagg | acgttaaggc | caagtatgaa | 240 |
| acatcaatcc | tagaacacag | tggtatcaga | ttgatcgaac | cagagttatt | caatggttac | 300 |
| aacccagaaa | agaaggaaat | gattcaagaa | gtcattgtcg | aagaagactt | ggaaccattt | 360 |
| gaggcttcga | aggaaactgc | cgaacaattt | aaacaccaac | atggtgacaa | agtggatatc | 420 |
| ttcgaaatcc | cagaaacagg | agagtactct | gttaagttac | taaagggtgc | cactttatac | 480 |
| attccaaagg | ctttgagatt | tgaccgtttg | gttgcaggtc | aaattccaac | tggttggaat | 540 |
| gctaagactt | atggtatctc | tgatgatatc | atttctcagg | ttgacccaat | cacattattc | 600 |
| gttttggtct | ctgttgtgga | agcatttatt | gcatctggta | tcaccgaccc | atacgaaatg | 660 |
| tacaaatacg | tacatgtttc | tgaggttggt | aactgttctg | ttctggtat  | gggtggtgtt | 720 |
| tctgccttac | gtggtatgtt | taaggaccgt | tcaaggatg  | agcctgtcca | aaatgatatt | 780 |
| ttacaagaat | catttatcaa | caccatgtcc | gcttgggtta | atatgttgtt | gatttcctca | 840 |
| tctggtccaa | tcaagacacc | tgttggtgcc | tgtgccacat | ccgtggaatc | tgttgacatt | 900 |
| ggtgtagaaa | ccatccttgt | ctggtaaggct | agaatctgta | ttgtcggtgg | ttacgatgat | 960 |
| ttccaagaag | aaggctccct | tgagttcggt | aacatgaagg | ccacttccaa | cactttggaa | 1020 |

```
gaatttgaac atggtcgtac cccagcggaa atgtccagac ctgccaccac tacccgtaac    1080
ggttttatgg aagctcaagg tgctggtatt caaatcatca tgcaagctga tttagctttg    1140
aagatgggtg tgccaattta cggtattgtt gccatggctg ctaccgccac cgataagatt    1200
ggtagatctg tgccagctcc aggtaagggt attttaacca ctgctcgtga acaccactcc    1260
agtgttaagt atgcttcacc aaacttgaac atgaagtaca gaaagcgcca attggttact    1320
cgtgaagctc agattaaaga ttgggtagaa acgaattgg aagctttgaa gttggaggcc     1380
gaagaaattc caagcgaaga ccaaaacgag ttcttacttg aacgtaccag agaaatccac    1440
aacgaagctg aaagtcaatt gagagctgca caacaacaat ggggtaacga cttctacaag    1500
agggacccac gtattgctcc attgagagga gcactggcta cttacggttt aactattgat    1560
gacttgggtg tcgcttcatt ccacggtaca tccacaaagg ctaatgacaa gaacgaatct    1620
gccacaatta atgaaatgat gaagcatttg ggtagatctg aaggtaatcc cgtcattggt    1680
gttttccaaa agttcttgac tggtcatcca aagggtgctg ctggtgcatg gatgatgaat    1740
ggtgctttgc aaattctaaa cagtggtatt attccaggta accgtaacgc tgataacgtg    1800
gataagatct tggagcaatt tgaatacgtc ttgtacccat ccaagacttt aaagaccgac    1860
ggtgtcagag ccgtgtccat cacttctttc ggttttggtc aaaagggtgg tcaagctatt    1920
gtggttcatc cagactactt atacggtgct                                     1950
```

```
<210> SEQ ID NO 7
<211> LENGTH: 45
<212> TYPE: DNA
<213> ORGANISM: Artificial Sequence
<220> FEATURE:
<223> OTHER INFORMATION: Primer

<400> SEQUENCE: 7
ttcttcgctg gtgttcgttg ttacgaagca tacccaaaca cttcc                     45

<210> SEQ ID NO 8
<211> LENGTH: 45
<212> TYPE: DNA
<213> ORGANISM: Artificial Sequence
<220> FEATURE:
<223> OTHER INFORMATION: Primer

<400> SEQUENCE: 8
acaccagcga agaataatac agtaattgct tttcttacgg agacg                     45

<210> SEQ ID NO 9
<211> LENGTH: 42
<212> TYPE: DNA
<213> ORGANISM: Artificial Sequence
<220> FEATURE:
<223> OTHER INFORMATION: Primer

<400> SEQUENCE: 9
agttgtgttc tacaaaggta tgactatgca agttgctgtt cc                        42

<210> SEQ ID NO 10
<211> LENGTH: 49
<212> TYPE: DNA
<213> ORGANISM: Artificial Sequence
<220> FEATURE:
<223> OTHER INFORMATION: Primer

<400> SEQUENCE: 10
```
catagtcata cctttgtaga acacaacttc aactaaagat tcgatagac 49

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
tctggttctt ctatgggtgg tgtttctgcc ttacg 35

<210> SEQ ID NO 12
<211> LENGTH: 43
<212> TYPE: DNA
<213> ORGANISM: Artificial Sequence
<220> FEATURE:
<223> OTHER INFORMATION: Primer

<400> SEQUENCE: 12
catagaagaa ccagaacagt taccaacctc agaaacatgt acg 43

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
tctggttctt cttggggtgg tgtttctgcc ttacg 35

<210> SEQ ID NO 14
<211> LENGTH: 43
<212> TYPE: DNA
<213> ORGANISM: Artificial Sequence
<220> FEATURE:
<223> OTHER INFORMATION: Primer

<400> SEQUENCE: 14
ccaagaagaa ccagaacagt taccaacctc agaaacatgt acg 43

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
attttacaag aatcatatat caacaccatg tccgc 35

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
tgattcttgt aaaatatcat tttggacagg c 31

<210> SEQ ID NO 17
<211> LENGTH: 51
<212> TYPE: DNA
<213> ORGANISM: Artificial Sequence -continued

```
<220> FEATURE:
<223> OTHER INFORMATION: Primer

<400> SEQUENCE: 17
tcttgtaaaa tagcattttg dacaggctca tccttgaaac ggtccttaaa c        51

<210> SEQ ID NO 18
<211> LENGTH: 55
<212> TYPE: DNA
<213> ORGANISM: Artificial Sequence
<220> FEATURE:
<223> OTHER INFORMATION: Primer

<400> SEQUENCE: 18
cctgtccaaa atgctatttt acaagaatca tttatcaaca ccatgtccgc ttggg     55

<210> SEQ ID NO 19
<211> LENGTH: 51
<212> TYPE: DNA
<213> ORGANISM: Artificial Sequence
<220> FEATURE:
<223> OTHER INFORMATION: Primer

<400> SEQUENCE: 19
tcttgtaaaa tatcagcttg dacaggctca tccttgaaac ggtccttaaa c        51

<210> SEQ ID NO 20
<211> LENGTH: 55
<212> TYPE: DNA
<213> ORGANISM: Artificial Sequence
<220> FEATURE:
<223> OTHER INFORMATION: Primer

<400> SEQUENCE: 20
cctgtccaag ctgatatttt acaagaatca tttatcaaca ccatgtccgc ttggg     55

<210> SEQ ID NO 21
<211> LENGTH: 55
<212> TYPE: DNA
<213> ORGANISM: Artificial Sequence
<220> FEATURE:
<223> OTHER INFORMATION: Primer

<400> SEQUENCE: 21
gaataatgtg attgggtcaa ccgcagaaat gatatcatca gagataccat aagtc     55

<210> SEQ ID NO 22
<211> LENGTH: 48
<212> TYPE: DNA
<213> ORGANISM: Artificial Sequence
<220> FEATURE:
<223> OTHER INFORMATION: Primer

<400> SEQUENCE: 22
ctgcggttga cccaatcaca ttattcgttt tggtctctgt tgtggaag             48

<210> SEQ ID NO 23
<211> LENGTH: 55
<212> TYPE: DNA
<213> ORGANISM: Artificial Sequence
<220> FEATURE:
<223> OTHER INFORMATION: Primer

<400> SEQUENCE: 23
gaataatgtg attgggtcaa cctcagaaat gatatcatca gagataccat aagtc     55
```

<210> SEQ ID NO 24
<211> LENGTH: 48
<212> TYPE: DNA
<213> ORGANISM: Artificial Sequence
<220> FEATURE:
<223> OTHER INFORMATION: Primer

<400> SEQUENCE: 24
ctgaggttga cccaatcaca ttattcgttt tggtctctgt tgtggaag        48

<210> SEQ ID NO 25
<211> LENGTH: 51
<212> TYPE: DNA
<213> ORGANISM: Artificial Sequence
<220> FEATURE:
<223> OTHER INFORMATION: Primer

<400> SEQUENCE: 25
tcttgtaaaa tatcatcttg gacaggctca tccttgaaac ggtccttaaa c        51

<210> SEQ ID NO 26
<211> LENGTH: 55
<212> TYPE: DNA
<213> ORGANISM: Artificial Sequence
<220> FEATURE:
<223> OTHER INFORMATION: Primer

<400> SEQUENCE: 26
cctgtccaag atgatatttt acaagaatca tttatcaaca ccatgtccgc ttggg        55

<210> SEQ ID NO 27
<211> LENGTH: 67
<212> TYPE: DNA
<213> ORGANISM: Artificial Sequence
<220> FEATURE:
<223> OTHER INFORMATION: Primer

<400> SEQUENCE: 27
cagtgaattg taatacgact cactataggg cgaattggag ctggcaaaac gtaggggcaa        60
acaaacg        67

<210> SEQ ID NO 28
<211> LENGTH: 64
<212> TYPE: DNA
<213> ORGANISM: Artificial Sequence
<220> FEATURE:
<223> OTHER INFORMATION: Primer

<400> SEQUENCE: 28
gcaaaatatg agctaattct tgctcaactt ccggcttcat tgtgtattac gatatagtta        60
atag        64

<210> SEQ ID NO 29
<211> LENGTH: 71
<212> TYPE: DNA
<213> ORGANISM: Artificial Sequence
<220> FEATURE:
<223> OTHER INFORMATION: Primer

<400> SEQUENCE: 29
gcatacaatc aactatcaac tattaactat atcgtaatac acaatgaagc cggaagttga        60
gcaagaatta g        71

```
<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
cacacaggaa acagctatga c                                              21
```

MICROBIOLOGICAL PRODUCTION OF SHORT FATTY ACIDS AND USES THEREOF

CROSS REFERENCE TO A RELATED APPLICATION

This application is a National Stage Application of International Application Number PCT/EP2016/057167, filed Mar. 31, 2016; which claims priority to European Patent Application No. 15162192.7, filed Apr. 1, 2015; both of which are incorporated herein by reference in their entirety.

The Sequence Listing for this application is labeled "SeqList-14Sep17-ST25.txt", which was created on Sep. 14, 2017, and is 38 KB. The entire content is incorporated herein by reference in its entirety.

FIELD OF THE INVENTION

The present invention relates to proteins involved in fatty acid synthesis, such as fatty acid synthases (FAS) variants, comprising one or more polypeptide chains, wherein said polypeptide chain(s) comprise one or more subunits comprising a malonyl/palmitoyl transferase domain (MPT domain), acetyl transferase domain (AT domain), and ketoacyl synthase domain (KS domain), and at least one amino acid substitution in the MPT domain at a position corresponding to R130, in the AT domain at a position corresponding to I306, and/or in the KS domain, preferably in the acyl binding channel and/or at KS domain binding site to ACP, to modulate affinities of acyl intermediates, and optionally further amino acid substitution(s). The present invention relates to the respective polypeptide domains.

The present invention further relates to nucleic acid molecules encoding the proteins (or the polypeptide domains) and to host cells containing said nucleic acid molecules. The present invention further relates to a method for the production of short fatty acids, CoA esters of short fatty acids, ethyl esters of short fatty acids, esters of short fatty acids with other metabolites, and/or enzyme bound short fatty acids ($C_6$ to $C_{12}$), comprising the expression of said nucleic acid molecules, preferably in said host tells. The present invention further relates to a method for the production of biofuels, flavoring compounds and/or fine chemicals, comprising the expression of said nucleic acid molecules, preferably in said host cells. The present invention also relates to the use of the proteins, nucleic acids molecule or host cells for the bulk production of short fatty acids ($C_6$ to $C_{12}$), the specific production of $C_6$ fatty acids and/or $C_8$ fatty acids, the bulk production of CoA esters of short fatty acids ($C_6$ to $C_{12}$), the specific production of $C_6$-CoA esters and/or $C_8$-CoA esters, the bulk production of ethyl esters of short fatty acids ($C_6$ to $C_{12}$), the specific production of $C_6$ fatty acid ethyl esters and/or $C_8$ fatty acid ethyl esters, the bulk production of esters of short fatty acids ($C_6$ to $C_{12}$) with other metabolites, the specific production of $C_6$ fatty acid esters with other metabolites and/or $C_8$ fatty acid esters with other metabolites, the bulk production of enzyme bound short fatty acids ($C_6$ to $C_{12}$), the specific production of enzyme bound $C_6$ fatty acids and/or enzyme bound $C_8$ fatty acids, the production of biofuels, fine chemicals and/or flavoring substances.

BACKGROUND OF THE INVENTION

With the rising demand for industrial products from a growing world population, the call for chemicals from renewable sources has become louder. Especially the efforts have been intensified, where fatty acids (FA) can play a crucial role as a platform chemical in the production of fine chemicals or even to replace fossil derived fuel by biofuels (Runguphan & Keasling, 2014; Choi & Lee, 2013). Accordingly, the production of FA in microorganisms has been investigated extensively, constantly pushing the limits: Yields have been shown in S. cerevisiae of up to 400 mg/L free FA (Runguphan & Keasling, 2014) and more recently even 2.2 g/L (Leber et al., 2015) (in both cases products were mostly in the long chain range); and up to 4.8 g/L in E. coli (predominantly $C_{14}$ and $C_{16}$) (Liu et al., 2012).

In microorganisms themselves, FA serve several purposes, mainly as a part of membranes, in signaling but also in energy storage. Their de-novo production is tightly regulated and conducted by an enzyme group, the fatty acid synthases (FASs) (Tehlivets et al., 2007). Throughout all organisms, their reaction mechanisms and their chemistry are essentially the same: A ketoacyl synthase (KS) is responsible for the elongation of an acyl chain starter molecule, typically an acetyl-CoA, with malonyl. The resulting β-ketoacyl intermediate is then processed in a series of reaction steps, in the ketoacyl reductase (KR), the dehydratase (DH) and enoyl reductase (ER), to a fully reduced acyl chain. This acyl chain which is now extended by two carbons, serves as a starter for the next cycle. The process repeats itself until the final product is cleft off.

As far as the overall structural organization of fatty acid synthases (FASs) is concerned, two types are distinguished: In type I FASs, all necessary enzymatic functions of FA production are concentrated in one multienzymatic complex, whereas in type II FAS systems, each reaction is catalyzed by a separate enzyme. Type II FASs are found in bacteria, while type I FASs are typical for few actinobacteria and all eukaryotic organisms, among these also S. cerevisiae.

In detail, in the S. cerevisiae FAS, one set of domains is distributed on two genes, fas1 and fas2. Multiple copies of the corresponding two polypeptide chains form the heterododecameric $\alpha_6\beta_6$ 2.6 MDa complex, which has been object of extensive x-ray structural analysis with resolutions up to 3.1 Å (see e.g. Jenni et al., 2007; Johansson et al., 2008). Its interpretation has led to substantially new insights in the reaction mechanisms of the whole FAS enzyme family (Grininger 2014; Beld et al., 2015). Above that, the kinetic parameters of S. cerevisiae FAS have been studied for decades.

The product distribution of the S. cerevisiae FAS is naturally in the long chain range of $C_{16}$ and $C_{18}$ (Tehlivets et al., 2007) and not directly suitable for applications where short FA are needed, as for instance biofuels in the petrol range. For this purpose, products typically have to have a length of $C_4$ to $C_{12}$ (Peralta-Yahya et al., 2012). Previous engineering efforts for the production of short FA have heavily relied on the utilization of thioesterases (TEs) with known specificities for short chain products (Beld et al., 2015), e.g. in a proof of principle study for the alkane production in E. coli (Choi & Lee, 2013) or the production of the precursors, short FA, in S. cerevisiae (with total yields up to 111 mg/L) (Leber & da Silva, 2014). In contrast, the rational engineering for the production of short FA was believed to be hard to achieve (Beld et al., 2015; Leber & da Silva, 2014).

US 2003/0145350 A1 discloses DNA sequences which code for a protein having the enzymatic activity of a beta-ketoacyl ACP synthase (KAS) of the enzyme complex of the fatty acid synthase (FAS). US 2003/0145350 A1 further discloses transgenic plants and micro-organisms which containing said nucleic acid sequences and a method for influencing the fatty acid pattern and/or for increasing the fatty acid content, especially the content of short and middle chain fatty acids, in plants, especially in seed tissues that synthesize and/or store triacylglycerols, as well as in micro-organisms, especially bacteria and algae. The method comprises the expression of proteins having the activity of a KAS of the enzyme complex or the fatty acid synthase in transgenic plants or micro-organisms.

There is a need in the art for further as well as improved means and methods for producing fatty acids in microorganisms, in particular fatty acids that are suitable for biofuel production, fine chemicals and other compounds.

SUMMARY OF THE INVENTION

According to the present invention this object is solved by a polypeptide or protein involved in fatty acid synthesis, said polypeptide or protein comprising one or more polypeptide chains, wherein said polypeptide chain(s) comprise
  (i) one or more subunits comprising the amino acid sequences of
    SEQ ID NO: 1 (malonyl/palmitoyl transferase domain, MPT domain);
    SEQ ID NO: 2 (acetyl transferase domain, AT domain), and/or
    SEQ ID NO: 3 (ketoacyl synthase domain, KS domain);
  (ii) at least one amino acid substitution
    in the MPT domain at a position corresponding to R130 of the amino acid sequence of SEQ ID NO: 1;
    in the AT domain at a position corresponding to I306 of the amino acid sequence of SEQ ID NO: 2;
    and/or
    in the KS domain, preferably in the acyl binding channel, preferably selected from a position corresponding to G236, M237 and F265 of the amino acid sequence of SEQ ID NO: 3;
  wherein the amino acid sequence comprising the at least one amino acid substitution has at least 60%, or preferably at least 70% or 80% or 90% or 95% sequence identity to the respective amino acid sequence of SEQ ID NO: 1, 2 and/or 3.

According to the present invention this object is solved by a polypeptide or protein involved in fatty acid synthesis, as defined above, comprising at least one further amino acid substitution in the KS domain, preferably selected from a position corresponding to Q193, N258 and D259 of the amino acid sequence of SEQ ID NO: 3.

According to the present invention this object is solved by a polypeptide domain comprising
  (i) one or more subunits comprising the amino acid sequences of
    SEQ ID NO: 1 (malonyl/palmitoyl transferase domain, MPT domain);
    SEQ ID NO: 2 (acetyl transferase domain, AT domain), or
    SEQ ID NO: 3 (ketoacyl synthase domain, KS domain);
  (ii) at least one amino acid substitution
    in the MPT domain at a position corresponding to R130 of the amino acid sequence of SEQ ID NO: 1;
    in the AT domain at a position corresponding to I306 of the amino acid sequence of SEQ ID NO: 2;
    and/or
    in the KS domain, preferably in the acyl binding channel, preferably selected from a position corresponding to G236, M237 and F265 of the amino acid sequence of SEQ ID NO: 3;
  wherein the amino acid sequence comprising the at least one amino acid substitution has at least 60%, or preferably at least 70% or 80% or 90% or 95% sequence identity to the respective amino acid sequence of SEQ ID NO: 1, 2 and/or 3.

According to the present invention this object is solved by a polypeptide domain, as defined above, comprising at least one further amino acid substitution in the KS domain, preferably selected from a position corresponding to Q193, N258 and D259 of the amino acid sequence of SEQ ID NO: 3.

According to the present invention this object is solved by a nucleic acid molecule coding for a protein of the present invention or a polypeptide domain of the present invention.

According to the present invention this object is solved by a host cell, containing a nucleic acid molecule of the present invention and preferably expressing said nucleic acid molecule, wherein said host cell is preferably selected from a bacterial cell or a fungus cell, more preferably a yeast cell, or an algae cell.

According to the present invention this object is solved by a method for the production of short fatty acids, CoA esters of short fatty acids, ethyl esters of short fatty acids, esters of short fatty acids with other metabolites, and/or enzyme bound short fatty acids ($C_6$ to $C_{12}$), comprising the expression of a nucleic acid molecule according to the present invention, preferably in a host cell according to the present invention.

According to the present invention this object is solved by a method for the production of biofuels, flavoring compounds and/or fine chemicals comprising the expression of a nucleic acid molecule according to the present invention, preferably in a host cell according to the present invention.

According to the present invention this object is solved by using a protein or polypeptide according to the present invention, a nucleic acid molecule according to the present invention, or a host cell according to the present invention for the bulk production of short fatty acids ($C_6$ to $C_{12}$).

According to the present invention this object is solved by using a protein or polypeptide according to the present invention, a nucleic acid molecule according to the present invention, or a host cell according to the present invention for the specific production of $C_6$ fatty acids.

According to the present invention this object is solved by using a protein or polypeptide according to the present invention, a nucleic acid molecule according to the present invention, or a host cell according to the present invention for the specific production of $C_8$ fatty acids.

According to the present invention this object is solved by using a protein or polypeptide according to the present invention, a nucleic acid molecule according to the present invention, or a host cell according to the present invention for the bulk production of CoA esters of short fatty acids ($C_6$ to $C_{12}$).

According to the present invention this object is solved by using a protein or polypeptide according to the present invention, a nucleic acid molecule according to the present invention, or a host cell according to the present invention for the specific production of $C_6$-CoA esters.

According to the present invention this object is solved by using a protein or polypeptide according to the present invention, a nucleic acid molecule according to the present invention, or a host cell according to the present invention for the specific production of $C_8$-CoA esters.

According to the present invention this object is solved by using a protein or polypeptide according to the present invention, a nucleic acid molecule according to the present invention, or a host cell according to the present invention for the bulk production of ethyl esters of short fatty acids ($C_6$ to $C_{12}$) or esters of short fatty acids ($C_6$ to $C_{12}$) with other metabolites.

According to the present invention this object is solved by using a protein or polypeptide according to the present invention, a nucleic acid molecule according to the present invention, or a host cell according to the present invention for the specific production of $C_6$ fatty acid ethyl esters or $C_6$ fatty acid esters with other metabolites.

According to the present invention this object is solved by using a protein or polypeptide according to the present invention, a nucleic acid molecule according to the present invention, or a host cell according to the present invention for the specific production of $C_8$ fatty acid ethyl esters or $C_8$ fatty acid esters with other metabolites.

According to the present invention this object is solved by using a protein or polypeptide according to the present invention, a nucleic acid molecule according to the present invention, or a host cell according to the present invention for the bulk production of enzyme bound short fatty acids ($C_6$ to $C_{12}$).

According to the present invention this object is solved by using a protein or polypeptide according to the present invention, a nucleic acid molecule according to the present invention, or a host cell according to the present invention for the specific production of enzyme bound $C_6$ fatty acids.

According to the present invention this object is solved by using a protein or polypeptide according to the present invention, a nucleic acid molecule according to the present invention, or a host cell according to the present invention for the specific production of enzyme bound $C_8$ fatty acids.

According to the present invention this object is solved by using a protein or polypeptide according to the present invention, a nucleic acid molecule according to the present invention, or a host cell according to the present invention for the production of biofuels, such as short alkanes, short alkenes, short alkynes, short esters and/or alcohols.

According to the present invention this object is solved by using a protein or polypeptide according to the present invention, a nucleic acid molecule according to the present invention, or a host cell according to the present invention for the production of fine chemicals, such as natural compounds where preferably short fatty acids ($C_6$ to $C_{12}$) or their derivatives (such as CoA esters, methyl/ethyl esters, esters with other metabolites, enzyme bound fatty acids, alcohols) are used as building block(s).

According to the present invention this object is solved by using a protein or polypeptide according to the present invention, a nucleic acid molecule according to the present invention, or a host cell according to the present invention for the production of flavoring substances, such as esters from short fatty acids ($C_6$ to $C_{12}$).

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Fatty Acid Synthase Variants and Domains

As discussed above, the present invention provides fatty acid synthase (FAS) variants, in particular type I fatty acid synthase (type I FAS) variants.

The polypeptides or proteins of the present invention comprise one or more polypeptide chains. Said one or more polypeptide chains comprise one or more subunits comprising a malonyl/palmitoyl transferase domain (MPT domain), an acetyl transferase domain (AT domain), and/or a ketoacyl synthase domain (KS domain).

The invention provides a protein or polypeptide involved in fatty acid synthesis, preferably having fatty acid synthase activity.

The invention also provides polypeptide domain(s) which are involved in fatty acid synthesis activity, such as subunits comprising a malonyl/palmitoyl transferase domain (MPT domain), an acetyl transferase domain (AT domain), and/or a ketoacyl synthase domain (KS domain).

Fatty acid synthases or polypeptides/proteins involved in fatty acid synthesis comprise one or more polypeptide chains, such as two, three, four or more polypeptide chains.

Fatty acid synthases or polypeptides/proteins involved in fatty acid synthesis furthermore comprise several different catalytic domains or subunits. Said catalytic domains or subunits can be located on said different/one or more polypeptide chains. The catalytic domains or subunits can also be split in parts and the different parts can be located on said different/one or more polypeptide chains (such as in case for the MPT domain of the type I FAS from *S. cerevisiae*).

According to the invention, the polypeptides or proteins of the present invention further comprise at least one amino acid substitution in the MPT domain at a position corresponding to R130, in the AT domain at a position corresponding to I306, and/or in the KS domain, preferably in the acyl binding channel, to modulate affinities of acyl intermediates, and optionally further amino acid substitution(s).

In particular, the present invention provides a polypeptide or protein involved in fatty acid synthesis, said polypeptide comprising one or more polypeptide chains, said polypeptide chain(s) comprising (i) at least one subunit comprising the amino acid sequences of
SEQ ID NO: 1 (malonyl/palmitoyl transferase domain, MPT domain);
SEQ ID NO: 2 (acetyl transferase domain, AT domain), and/or
SEQ ID NO: 3 (ketoacyl synthase domain, KS domain);
(ii) at least one amino acid substitution
in the MPT domain at a position corresponding to R130 of the amino acid sequence of SEQ ID NO: 1;
in the AT domain at a position corresponding to I306 of the amino acid sequence of SEQ ID NO: 2;
and/or
in the KS domain, preferably in the acyl binding channel, preferably selected from a position corresponding to G236, M237 and F265 of the amino acid sequence of SEQ ID NO: 3.

In particular, the present invention provides a polypeptide or protein involved in fatty acid synthesis, as defined above, comprising at least one further amino acid substitution in the KS domain, preferably in the acyl binding channel and/or at KS domain binding site to ACP, preferably selected from a position corresponding to Q193, N258 and D259 of the amino acid sequence of SEQ ID NO: 3.

According to the present invention, the amino acid sequence comprising the at least one amino acid substitution has at least 60%, or preferably at least 70% or 80% or 90% or 95% sequence identity to the respective amino acid sequence of SEQ ID NO: 1, 2 and/or 3.

In a preferred embodiment, the amino acid sequence comprising the at least one amino acid substitution has at least 80%, or preferably at least 90% or 95% sequence identity to the respective amino acid sequence of SEQ ID NO: 3.

In particular, the present invention provides a polypeptide domain comprising
(i) one or more subunits comprising the amino acid sequences of
SEQ ID NO: 1 (malonyl/palmitoyl transferase domain, MPT domain);
SEQ ID NO: 2 (acetyl transferase domain, AT domain), or
SEQ ID NO: 3 (ketoacyl synthase domain, KS domain);
(ii) at least one amino acid substitution
in the MPT domain at a position corresponding to R130 of the amino acid sequence of SEQ ID NO: 1;
in the AT domain at a position corresponding to I306 of the amino acid sequence of SEQ ID NO: 2;
and/or
in the KS domain, preferably in the acyl binding channel, preferably selected from a position corresponding to G236, M237 and F265 of the amino acid sequence of SEQ ID NO: 3;

In particular, the present invention provides a polypeptide domain, as defined above, comprising at least one further amino acid substitution in the KS domain, preferably at KS domain binding site to ACP, preferably selected from a position corresponding to Q193, N258 and D259 of the amino acid sequence of SEQ ID NO: 3.

According to the present invention, the amino acid sequence comprising the at least one amino acid substitution has at least 60%, or preferably at least 70% or 80% or 90% or 95% sequence identity to the respective amino acid sequence of SEQ ID NO: 1, 2 and/or 3.

In a preferred embodiment, the amino acid sequence comprising the at least one amino acid substitution has at least 80%, or preferably at least 90% or 95% sequence identity to the respective amino acid sequence of SEQ ID NO: 3.

In a preferred embodiment, the MPT and/or AT domain of the polypeptide(s) or protein(s) (or the polypeptide domain(s)) have an in vitro and/or in vivo transferase activity; and/or the KS domain of the polypeptide(s) or protein(s) has an in vitro and/or in vivo ketoacyl synthase activity.

This means that even though there is at least one amino acid substitution in the MPT domain, AT domain and/or KS domain, as disclosed herein, the MPT and/or AT domain of the polypeptide(s) or protein(s) have an in vitro and/or in vivo transferase activity; and/or the KS domain of the polypeptide(s) or protein(s) has an in vitro and/or in vivo ketoacyl synthase activity.

There are two principal classes of fatty acid synthases.

Type I systems utilize a single large, multifunctional enzyme and are common to both mammals and fungi (although the structural arrangement of fungal and mammalian synthases differ). A Type I fatty acid synthase system is also found in the CMN group of bacteria (corynebacteria, mycobacteria, and nocardia). In these bacteria, the FAS I system produces palmititic acid, and cooperates with the FAS II system to produce a greater diversity of lipid products. Type II is found in archaea and bacteria, and is characterized by the use of discrete, monofunctional enzymes for fatty acid synthesis.

For example, mammalian FAS usually consists of a homodimer of two identical protein subunits, in which three catalytic domains in the N-terminal section (-ketoacyl synthase (KS), malonyl/acetyltransferase (MAT), and dehydratase (DH)), are separated by a core region of 600 residues from four C-terminal domains (enoyl reductase (ER), -ketoacyl reductase (KR), acyl carrier protein (ACP) and thioesterase (TE)).

In one embodiment, the protein or polypeptide of the present invention is a type I FAS, such as type I FAS of Saccharomyces cerevisiae. In the case of Saccharomyces cerevisiae, the FAS is split into two polypeptide chains, but still is considered a type I FAS since the catalytic centers are organized in one enzyme complex.

In one embodiment, the protein or polypeptide of the present invention is the type I FAS of Saccharomyces cerevisiae.

The particular type I FAS from S. cerevisiae comprises two polypeptide chains which among other domains, contain
on a first polypeptide chain FAS 1:
the malonyl/palmitoyl transferase domain, MPT domain
and
the acetyl transferase domain, AT domain
on a second polypeptide chain, FAS 2
ketoacyl synthase domain, KS domain.

In S. cerevisiae, the chains are encoded by fas1 (to be found in Genbank: M30162.1) and fas2 (to be found in Genbank: J03936.1).

SEQ ID NO: 1 shows the amino acid sequence of the MPT domain (part of sequence of Uniprot Identifier: P07149 and of P19097)

Malonyl/palmitoyl transferase (MPT domain), (sequence is split in S. cerevisiae with the splitting site indicated by *: from residue 1-347 shown here, it is part of S. cerevisiae FAS 1 (beta chain), Uniprot Identifier: P07149; from residue 348-429 shown here, it is part of S. cerevisiae FAS 2 (beta alpha), Uniprot Identifier: P19097)

```
SILDIVINNPVNLTIHFGGEKGKRIRENYSAMIFETIVDGKLKTEKIFKE

INEHSTSYTFRSEKGLLSATQFTQPALTLMEKAAFEDLKSKGLIPADATF

AGHSLGEYAALASLADVMSIESLVEVVFYRGMTMQVAVPRDELGRSNYGM

IAINPGRVAASFSQEALQYVVERVGKRTGWLVEIVNYNVENQQYVAAGDL

RALDTVTNVLNFIKLQKIDIIELQKSLSLEEVEGHLFEIIDEASKKSAVK

PRPLKLERGFACIPLVGISVPFHSTYLMNGVKPFKSFLKKNIIKENVKVA

RLAGKYIPNLTAKPFQVTKEYFQDVYDLTGSEPIKEIIDNWEKYEQS*

MKPEVEQELAHILLTELLAYQFASPVRWIETQDVFLKDFNTERVVEIGPS

PTLAGMAQRTLKNKYESYDAALSLHREILCYS
```

SEQ ID NO: 2 shows the amino acid sequence of the AT domain (part of sequence of Uniprot Identifier: P07149)

Acetyl transferase (AT domain), (part of S. cerevisiae FAS 1 (beta chain),
Uniprot Identifier: P07149

```
MDAYSTRPLTLSHGSLEHVLLVPTASFFIASQLQEQFNKILPEPTEGFAA

DDEPTTPAELVGKFLGYVSSLVEPSKVGQFDQVLNLCLTEFENCYLEGND
```

```
IHALAAKLLQENDTTLVKTKELIKNYITARIMAKRPFDKKSNSALFRAVG

EGNAQLVAIFGGQGNTDDYFEELRDLYQTYHVLVGDLIKFSAETLSELIR

TTLDAEKVFTQGLNILEWLENPSNTPDKDYLLSIPISCPLIGVIQLAHYV

VTAKLLGETPGELRSYLKGATGHSQGLVTAVAIAETDSWESFFVSVRKAI

TVLFFIGVRCYEAYPNTSLPPSILEDSLENNEGVPSPMLSISNLTQEQVQ

DYVNKTNSHLPAGKQVEISLVNGAKNLVVSGPPQSLYGLNLTLRKAKAPS

GLDQSRIPFSERKLKESNRFLPVASPFHSHLLVPASDLINKDLVKNNVSF

NAKDIQIPVYDTEDGSDLRVLSGSISERIVDCIIRLPVKWETTTQFKATH

ILDFGPGGASGLGVLTHRNKDGTGVRVIVAGTLDINPDDDYGFKQEIFDV

T
```

SEQ ID NO: 3 shows the amino acid sequence of the KS domain (part of sequence of Uniprot Identifier: P19097)

Ketoacyl synthase (KS domain), (part of S. cerevisiae FAS 2 (alpha chain), Uniprot Identifier: P19097)

```
LERVIVVTGFAEVGPWGSARTRWEMEAFGEFSLEGCVEMAWIMGFISYHN

GNLKGRPYTGWVDSKTKEPVDDKDVKAKYETSILEHSGIRLIEPELFNGY

NPEKKEMIQEVIVEEDLEPFEASKETAEQFKHQHGDKVDIFEIPETGEYS

VKLLKGATLYIPKALRFDRLVAGQIPTGWNAKTYGISDDIISQVDPITLF

VLVSVVEAFIASGITDPYEMYKYVHVSEVGNCSGSGMGGVSALRGMFKDR

FKDEPVQNDILQESFINTMSAWVNMLLISSSGPIKTPVGACATSVESVDI

GVETILSGKARICIVGGYDDFQEEGSFEFGNMKATSNTLEEFEHGRTPAE

MSRPATTTRNGFMEAQGAGIQIIMQADLALKMGVPIYGIVAMAATATDKI

GRSVPAPGKGILTTAREHHSSVKYASPNLNMKYRKRQLVTREAQIKDWVE

NELEALKLEAEEIPSEDQNEFLLERTREIHNEAESQLRAAQQQWGNDFYK

RDPRIAPLRGALATYGLTIDDLGVASFHGTSTKANDKNESATINEMMKHL

GRSEGNPVIGVFQKFLTGHPKGAAGAWMMNGALQILNSGIIPGNRNADNV

DKILEQFEYVLYPSKTLKTDGVRAVSITSFGFGQKGGQAIVVHPDYLYGA
```

As far as the overall structural organization of fatty acid synthases (FASs) is concerned, two types are distinguished: In type I FASs, all necessary enzymatic functions of fatty acid (FA) production are concentrated in one multienzymatic complex, whereas in type II FAS systems, each reaction is catalyzed by a separate enzyme. For type I FAS systems, the intermediates are always covalently bound to the multienzymatic complex leading to extremely high efficiency. Type II FASs are found in bacteria, while type I FASs are typical for few actinobacteria and all eukaryotic organisms, among these also S. cerevisiae.

In detail, in the S. cerevisiae FAS, one set of domains is distributed on two genes, fas1 (encoding the β chain or FAS1) and fas2 (encoding the α chain or FAS2). On the β chain, the AT domain, the ER domain, the DH domain and part of the MPT domain are located in the order as written here. The rest of the MPT domain, the ACP domain, the KR domain, the KS domain and the PPT domain can be found on the a chain correspondingly. Multiple copies of the corresponding two polypeptide chains form the heterododecameric $\alpha_6\beta_6$ 2.6 MDa complex, which has been object of extensive x-ray structural analysis with resolutions up to 3.1 Å (see e.g. Jenni et al., 2007; Johansson et al., 2008). Its interpretation has led to substantially new insights in the reaction mechanisms of the whole FAS enzyme family (Grininger 2014; Beld et al., 2015). Above that, the kinetic parameters of S. cerevisiae FAS have been studied for decades.

As used herein, the term "at a position corresponding to" means the respective position in SEQ ID No: 1, 2 or 3 which, however, in related polypeptide chains can have another relative position number. The equivalent substitution can be determined by comparing a position in both sequences, which may be aligned for the purpose of comparison. The relative position of the amino acid can vary due to different length of the related polypeptide, or deletions or additions of amino acids in the related polypeptide.

The polypeptides of the present invention, in particular the type I FAS variants, have an in vitro and/or in vivo fatty acid synthase I (FAS I) enzymatic activity.

As used herein, the term "percent (%) identical" refers to sequence identity between two amino acid sequences. Identity can be determined by comparing a position in both sequences, which may be aligned for the purpose of comparison. When an equivalent position in the compared sequences is occupied by the same amino acid, the molecules are considered to be identical at that position.

As used herein, the term "functional equivalent" refers to amino acid sequences that are not 100% identical to the amino acid sequence of SEQ ID NO. 1, 2 or 3 and comprise amino acid additions and/or insertions and/or deletions and/or substitutions and/or exchanges, which do not alter or change the activity or function of the protein as compared to the protein having the amino acid sequence of SEQ ID NO: 1, 2 or 3, i.e. an "functional equivalent", for example, encompasses an amino acid sequence with conservative amino acid substitutions or smaller deletions and/or insertions as long as these modifications do not substantially affect the in vitro and/or in vivo fatty acid synthase (FAS) enzymatic activity.

Generally, a person skilled in the art is aware of the fact that some amino acid exchanges in the amino acid sequence of a protein do not have an influence on the (secondary or tertiary) structure, function and/or activity of that protein. Amino acid sequences with such "neutral" amino acid exchanges as compared to the amino acid sequences disclosed herein fall within the scope of the present invention.

In some embodiments, the polypeptide(s) or protein(s) have one, two, three, four, five, six or more amino acid substitutions in the MPT domain, AT domain and/or KS domain.

For example, a polypeptide of the present inventions has one amino acid substitution in each of the MPT domain, AT domain and/or KS domain.

For example, a polypeptide of the present inventions has two amino acid substitutions, such as:
one amino acid substitution in each of the MPT domain and the AT domain,
one amino acid substitution in each of the MPT domain and the KS domain,
one amino acid substitution in each of the AT domain and the KS domain,
two amino acid substitutions in the MPT domain,
two amino acid substitutions in the AT domain,
two amino acid substitutions in the KS domain.

For example, a polypeptide of the present inventions has three amino acid substitutions, such as:
three amino acid substitutions in the MPT domain,
three amino acid substitutions in the AT domain,
three amino acid substitutions in the KS domain.

two amino acid substitutions in the MPT domain and one amino acid substitution in either one of the AT domain and the KS domain, two amino acid substitutions in the AT domain and one amino acid substitution in either one of the MPT domain and the KS domain, two amino acid substitutions in the KS domain and one amino acid substitution in either one of MPT domain and the AT domain, one amino acid substitution in each of the MPT domain, AT domain and KS domain.

Preferably, the polypeptides or proteins according to the present invention comprise the amino acid substitution R130K in the MPT domain (SEQ ID NO. 1), and/or the amino acid substitution I306A in the AT domain (SEQ ID NO: 2).

Preferably, the polypeptides or proteins according to the present invention comprise amino acid substitution(s) in the acyl binding channel of the KS domain, more preferably amino acid substitution(s) G236S, M237W and/or F265Y in the KS domain (SEQ ID NO: 3).

Preferably, the polypeptides or proteins according to the present invention comprise the amino acid substitution R130K in the MPT domain (SEQ ID NO. 1), and/or the amino acid substitution I306A in the AT domain (SEQ ID NO: 2), and/or the amino acid substitution(s) G236S, M237W and/or F265Y in the KS domain (SEQ ID NO: 3)

and/or the amino acid substitution(s) Q193A, Q193E, N258A, N258D and/or D259A in the KS domain (SEQ ID NO: 3).

Disclaimer:

The present invention does not encompass polypeptide domain(s) that only comprise the amino acid substitution G236S in the KS domain.

In an embodiment, where the polypeptide domain of the present invention comprises the KS domain and an amino acid substitution G236S in said KS domain (SEQ ID NO. 3), it comprises at least one additional amino acid substitution in said KS domain.

The present invention does not encompass polypeptides or proteins that only comprise the amino acid substitution G236S in the KS domain.

In an embodiment, where the polypeptide or protein of the present invention comprises the amino acid substitution G236S in the KS domain (SEQ ID NO. 3), it comprises at least one additional amino acid substitution.

Preferably, the proteins or polypeptides according to the present invention are selected from the group of a protein comprising the amino acid substitutions I306A and G236S;

a protein comprising the amino acid substitutions I306A, R130K and F265Y;

a protein comprising the amino acid substitutions I306A, R130K and G236S;

a protein comprising the amino acid substitution R130K;

a protein comprising the amino acid substitutions I306A, R130K, G236S and M237W;

a protein comprising the amino acid substitutions I306A, G236S and M237W;

a protein comprising the amino acid substitutions G236S and M237W;

a protein comprising the amino acid substitutions I306A and R130K;

a protein comprising the amino acid substitutions R130K and G236S;

a protein comprising the amino acid substitutions I306A and F265Y;

a protein comprising the amino acid substitutions I306A, G236S and F265Y;

a protein comprising the amino acid substitutions R130K, G236S and M237W;

a protein comprising the amino acid substitutions G236S and F265Y;

a protein comprising the amino acid substitutions R130K, G236S and F265Y;

a protein comprising the amino acid substitutions I306A, R130K, G236S and F265Y;

a protein comprising the amino acid substitutions I306A, G236S, M237W and F265Y;

a protein comprising the amino acid substitution I306A;

a protein comprising the amino acid substitution M237W;

a protein comprising the amino acid substitution F265Y;

a protein comprising the amino acid substitutions I306A and M237W;

a protein comprising the amino acid substitutions R130K and M237W;

a protein comprising the amino acid substitutions R130K and F265Y;

a protein comprising the amino acid substitutions I306A, R130K and M237W;

a protein comprising the amino acid substitutions I306A, M237W and F265Y;

a protein comprising the amino acid substitutions R130K, M237W and F265Y;

a protein comprising the amino acid substitutions G236S, M237W and F265Y;

a protein comprising the amino acid substitutions M237W and F265Y;

a protein comprising the amino acid substitutions I306A, R130K, M237W and F265Y;

a protein comprising the amino acid substitutions R130K, G236S, M237W and F265Y;

a protein comprising the amino acid substitutions I306A, R130K, G236S, M237W and F265Y;

a protein comprising the amino acid substitutions I306A, R130K, G236S and D259A;

a protein comprising the amino acid substitutions I306A, R130K, G236S, M237W and D259A;

a protein comprising the amino acid substitutions I306A, R130K, G236S and N258A;

a protein comprising the amino acid substitutions I306A, R130K, G236S, M237W and N258A;

a protein comprising the amino acid substitutions I306A, R130K, G236S and N258D;

a protein comprising the amino acid substitutions I306A, R130K, G236S, M237W and N258D;

a protein comprising the amino acid substitutions I306A, R130K, G236S and Q193A;

a protein comprising the amino acid substitutions I306A, R130K, G236S, M237W and Q193A;

a protein comprising the amino acid substitutions I306A, R130K, G236S and Q193E;

a protein comprising the amino acid substitutions I306A, R130K, G236S, M237W and Q193E.

The present invention preferably provides the following proteins or polypeptides/type I FAS variants:

variant I306A/G236S;

variant I306A/R130K/F265Y;

variant I306A/R130K/G236S;
variant R130K;
variant I306A/R130K/G236S/M237W;
variant I306A/G236S/M237W;
variant G236S/M237W;
variant I306A/R130K;
variant R130K/G236S;
variant I306A/F265Y;
variant I306A/G236S/F265Y;
variant R130K/G236S/M237W;
variant G236S/F265Y;
variant R130K/G236S/F265Y;
variant I306A/R130K/G236S/F265Y;
variant I306A/G236S/M237W/F265Y;
variant I306A;
variant M237W;
variant F265Y;
variant I306A/M237W;
variant R130K/M237W;
variant R130K/F265Y;
variant I306A/R130K/M237W;
variant I306A/M237W/F265Y;
variant R130K/M237W/F265Y;
variant G236S/M237W/F265Y;
variant M237W/F265Y;
variant I306A/R130K/M237W/F265Y;
variant R130K/G236S/M237W/F265Y;
variant I306A/R130K/G236S/M237W/F265Y;
variant I306A/R130K/G236S/D259A,
variant I306A/R130K/G236S/M237W/D259A;
variant I306A/R130K/G236S/N258A;
variant I306A/R130K/G236S/M237W/N258A;
variant I306A/R130K/G236S/N258D;
variant I306A/R130K/G236S/M237W/N258D;
variant I306A/R130K/G236S/Q193A;
variant I306A/R130K/G236S/M237W/Q193A;
variant I306A/R130K/G236S/Q193E; and
variant I306A/R130K/G236S/M237W/Q193E.

Preferably, the protein (s) or polypeptide(s) of the present invention result in elevated overall production of short fatty acids, CoA esters of short fatty acids, ethyl esters of short fatty acids, esters of short fatty acids with other metabolites, and/or enzyme bound short fatty acids ($C_6$ to $C_{12}$) compared to the wild type polypeptide(s) or the polypeptide(s) without such amino acid substitution(s).

The elevated overall production of short fatty acids, CoA esters of short fatty acids, short fatty acid ethyl esters, short fatty acid esters with other metabolites, and/or enzyme bound short fatty acids ($C_6$ to $C_{12}$) is increased at least 2-fold, or preferably at least 5-fold or 10-fold or 20-fold or 27-fold.

The term "short fatty acid" refers to a fatty acid of short to medium length with $C_6$ to $C_{12}$.

Variants with Increased Selectivity for $C_6$

In a preferred embodiment, the polypeptide(s) of the present invention show(s) an increased selectivity for the production of $C_6$ fatty acids, $C_6$ CoA esters, $C_6$ fatty acid ethyl esters, $C_6$ fatty acid esters with other metabolites, and/or enzyme bound $C_6$ fatty acids compared to wild type polypeptide(s) or the polypeptide without such amino acid substitution(s).

The selectivity for the production of $C_6$ fatty acids, $C_6$ CoA esters, $C_6$ fatty acid ethyl esters, $C_6$ fatty acid esters with other metabolites, and/or enzyme bound $C_6$ fatty acids compared to wild type is increased where the share of $C_6$ makes up at least 30%, or preferably at least 40% or 50% or 70% or 80% or 90% of the detected chain length between $C_6$ and $C_{12}$.

In particular, proteins or polypeptides of the present invention, wherein the amino acid substitution(s) is/are selected from I306A (in the AT domain on SEQ ID NO: 2) and G236S (in the KS domain on SEQ ID NO: 3);

I306A (in the AT domain on SEQ ID NO: 2) and F265Y (in the KS domain on SEQ ID NO: 3);

I306A (in the AT domain on SEQ ID NO: 2), G236S and M237W (in the KS domain on SEQ ID NO: 3);

I306A (in the AT domain on SEQ ID NO: 2), R130K (in the MPT domain on SEQ ID NO: 1) and G236S (in the KS domain on SEQ ID NO: 3);

G236S and M237W (in the KS domain on SEQ ID NO: 3);

I306A (in the AT domain on SEQ ID NO: 2), R130K (in the MPT domain on SEQ ID NO: 1), G236S and M237W (in the KS domain on SEQ ID NO: 3);

R130K (in the MPT domain on SEQ ID NO: 1);

I306A (in the AT domain on SEQ ID NO: 2), G236S and F265Y (in the KS domain on SEQ ID NO: 3);

I306A (in the AT domain on SEQ ID NO: 2), R130K (in the MPT domain on SEQ ID NO: 1) and F265Y (in the KS domain on SEQ ID NO: 3);

I306A (in the AT domain on SEQ ID NO: 2) and R130K (in the MPT domain on SEQ ID NO: 1);

R130K (in the MPT domain on SEQ ID NO: 1) and G236S (in the KS domain on SEQ ID NO: 3);

R130K (in the MPT domain on SEQ ID NO: 1), G236S and M237W (in the KS domain on SEQ ID NO: 3);

G236S and F265Y (in the KS domain on SEQ ID NO: 3);

R130K (in the MPT domain on SEQ ID NO: 1), G236S and F265Y (in the KS domain on SEQ ID NO: 3);

I306A (in the AT domain on SEQ ID NO: 2), R130K (in the MPT domain on SEQ ID NO: 1), G236S and F265Y (in the KS domain on SEQ ID NO: 3);

I306A (in the AT domain on SEQ ID NO: 2), G236S, M237W and F265Y (in the KS domain on SEQ ID NO: 3);

I306A (in the AT domain on SEQ ID NO: 2);

M237W (in the KS domain on SEQ ID NO: 3);

F265Y (in the KS domain on SEQ ID NO: 3);

I306A (in the AT domain on SEQ ID NO: 2) and M237W (in the KS domain on SEQ ID NO: 3);

R130K (in the MPT domain on SEQ ID NO: 1) and M237W (in the KS domain on SEQ ID NO: 3);

R130K (in the MPT domain on SEQ ID NO: 1) and F265Y (in the KS domain on SEQ ID NO: 3);

I306A (in the AT domain on SEQ ID NO: 2), R130K (in the MPT domain on SEQ ID NO: 1) and M237W (in the KS domain on SEQ ID NO: 3);

I306A (in the AT domain on SEQ ID NO: 2), M237W and F265Y (in the KS domain on SEQ ID NO: 3);

R130K (in the MPT domain on SEQ ID NO: 1), M237W and F265Y (in the KS domain on SEQ ID NO: 3);

G236S, M237W and F265Y (in the KS domain on SEQ ID NO: 3);

M237W and F265Y (in the KS domain on SEQ ID NO: 3);

I306A (in the AT domain on SEQ ID NO: 2), R130K (in the MPT domain on SEQ ID NO: 1), M237W and F265Y (in the KS domain on SEQ ID NO: 3);

R130K (in the MPT domain on SEQ ID NO: 1), G236S, M237W and F265Y (in the KS domain on SEQ ID NO: 3);

I306A (in the AT domain on SEQ ID NO: 2), R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S and N258A (in the KS domain on SEQ ID NO: 3);
I306A (in the AT domain on SEQ ID NO: 2), R130K (in the MPT domain on SEQ ID NO: 1), G236S and N258D (in the KS domain on SEQ ID NO: 3);
I306A (in the AT domain on SEQ ID NO: 2), R130K (in the MPT domain on SEQ ID NO: 1), G236S, M237W and N258A (in the KS domain on SEQ ID NO: 3);
I306A (in the AT domain on SEQ ID NO: 2), R130K (in the MPT domain on SEQ ID NO: 1), G236S, M237W and N258D (in the KS domain on SEQ ID NO: 3);
preferably selected from
I306A (in the AT domain on SEQ ID NO: 2) and G236S (in the KS domain on SEQ ID NO: 3);
I306A (in the AT domain on SEQ ID NO: 2) and F265Y (in the KS domain on SEQ ID NO: 3);
I306A (in the AT domain on SEQ ID NO: 2), G236S and M237W (in the KS domain on SEQ ID NO: 3);
I306A (in the AT domain on SEQ ID NO: 2), R130K (in the MPT domain on SEQ ID NO: 1) and G236S (in the KS domain on SEQ ID NO: 3)
G236S and M237W (in the KS domain on SEQ ID NO: 3).

increase(s) the selectivity for the production of $C_6$ fatty acids, $C_6$ CoA, $C_6$ fatty acid ethyl esters, $C_6$ fatty acid esters with other metabolites, esters and/or enzyme bound $C_6$ fatty acids compared to wild type polypeptide(s) or the polypeptide without such amino acid substitution(s).

Namely, proteins or polypeptides of the present invention, wherein the amino acid substitution(s) is/are selected from
I306A and G236S;
I306A and F265Y;
I306A, G236S and M237W;
I306A, R130K and G236S;
G236S and M237W;
I306A, R130K, G236S and M237W;
R130K;
I306A, G236S and F265Y;
I306A, R130K and F265Y;
I306A and R130K;
R130K and G236S;
R130K, G236S and M237W;
G236S and F265Y;
R130K, G236S and F265Y;
I306A, R130K, G236S and F265Y;
I306A, G236S, M237W and F265Y;
I306A;
M237W;
F265Y;
I306A and M237W;
R130K and M237W;
R130K and F265Y;
I306A, R130K and M237W;
I306A, M237W and F265Y;
R130K, M237W and F265Y;
G236S, M237W and F265Y;
M237W and F265Y;
I306A, R130K, M237W and F265Y;
R130K, G236S, M237W and F265Y;
I306A, R130K, G236S, M237W and F265Y;
I306A, R130K, G236S and N258A;
I306A, R130K, G236S and N258D;
I306A, R130K, G236S, M237W and N258A;
I306A, R130K, G236S, M237W and N258D;
preferably selected from
I306A and G236S;
I306A and F265Y;
I306A, G236S and M237W;
I306A, R130K and G236S;
G236S and M237W;
more preferably
I306A and G236S,
I306A and F265Y,
I306A, G236S and M237W,
I306A, R130K and G236S,
increase(s) the selectivity for the production of $C_6$ fatty acids, $C_6$ fatty acid CoA esters, $C_6$ fatty acid ethyl esters, $C_6$ fatty acid esters with other metabolites, esters and/or enzyme bound $C_6$ fatty acids compared to wild type polypeptide(s) or the polypeptide without such amino acid substitution(s).

Variants with Increased Selectivity for $C_8$

In a preferred embodiment, the protein (s) or polypeptide(s) of the present invention show(s) an increased selectivity for the production of $C_8$ fatty acids, $C_8$ fatty acid CoA esters, $C_8$ fatty acid ethyl esters, $C_8$ fatty acid esters with other metabolites, and/or enzyme bound $C_8$ fatty acids compared to wild type polypeptide(s) or the polypeptide without such amino acid substitution(s).

The selectivity for the production of $C_8$ fatty acids, $C_8$ fatty acid CoA esters and/or enzyme bound $C_8$ fatty acids compared to wild type is increased where the share of $C_8$ makes up at least 30%, or preferably at least 40% or 50% or 70% or 80% or 89% of the detected chain length between $C_6$ and $C_{12}$.

In particular, proteins or polypeptides of the present invention, wherein the amino acid substitution(s) is/are selected from
I306A (in the AT domain on SEQ ID NO: 2), R130K (in the MPT domain on SEQ ID NO: 1) and F265Y (in the KS domain on SEQ ID NO: 3)
R130K (in the MPT domain on SEQ ID NO: 1);
I306A (in the AT domain on SEQ ID NO: 2), R130K (in the MPT domain on SEQ ID NO: 1), G236S and M237W (in the KS domain on SEQ ID NO: 3);
R130K (in the MPT domain on SEQ ID NO: 1) and G236S (in the KS domain on SEQ ID NO: 3);
I306A (in the AT domain on SEQ ID NO: 2) and R130K (in the MPT domain on SEQ ID NO: 1);
G236S and M237W (in the KS domain on SEQ ID NO: 3);
I306A (in the AT domain on SEQ ID NO: 2), R130K (in the MPT domain on SEQ ID NO: 1) and G236S (in the KS domain on SEQ ID NO: 3);
I306A (in the AT domain on SEQ ID NO: 2), G236S and M237W (in the KS domain on SEQ ID NO: 3);
R130K (in the MPT domain on SEQ ID NO: 1), G236S and M237W (in the KS domain on SEQ ID NO: 3);
I306A (in the AT domain on SEQ ID NO: 2) and F265Y (in the KS domain on SEQ ID NO: 3);
M237W (in the KS domain on SEQ ID NO: 3);
I306A (in the AT domain on SEQ ID NO: 2), G236S and F265Y (in the KS domain on SEQ ID NO: 3);
G236S and F265Y (in the KS domain on SEQ ID NO: 3);
I306A (in the AT domain on SEQ ID NO: 2) and G236S (in the KS domain on SEQ ID NO: 3);
R130K (in the MPT domain on SEQ ID NO: 1), G236S and F265Y (in the KS domain on SEQ ID NO: 3)
I306A (in the AT domain on SEQ ID NO: 2), R130K (in the MPT domain on SEQ ID NO: 1), G236S and F265Y (in the KS domain on SEQ ID NO: 3);

I306A (in the AT domain on SEQ ID NO: 2), G236S, M237W and F265Y (in the KS domain on SEQ ID NO: 3);
I306A (in the AT domain on SEQ ID NO: 2);
F265Y (in the KS domain on SEQ ID NO: 3);
I306A (in the AT domain on SEQ ID NO: 2) and M237W (in the KS domain on SEQ ID NO: 3);
R130K (in the MPT domain on SEQ ID NO: 1) and M237W (in the KS domain on SEQ ID NO: 3);
R130K (in the MPT domain on SEQ ID NO: 1) and F265Y (in the KS domain on SEQ ID NO: 3);
I306A (in the AT domain on SEQ ID NO: 2), R130K (in the MPT domain on SEQ ID NO: 1) and M237W (in the KS domain on SEQ ID NO: 3);
I306A (in the AT domain on SEQ ID NO: 2), M237W and F265Y (in the KS domain on SEQ ID NO: 3);
R130K (in the MPT domain on SEQ ID NO: 1), M237W and F265Y (in the KS domain on SEQ ID NO: 3);
G236S, M237W and F265Y (in the KS domain on SEQ ID NO: 3);
M237W and F265Y (in the KS domain on SEQ ID NO: 3);
I306A (in the AT domain on SEQ ID NO: 2), R130K (in the MPT domain on SEQ ID NO: 1), M237W and F265Y (in the KS domain on SEQ ID NO: 3);
R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S and D259A (in the KS domain on SEQ ID NO: 3);
I306A (in the AT domain on SEQ ID NO: 2), R130K (in the MPT domain on SEQ ID NO: 1), G236S, M237W and D259A (in the KS domain on SEQ ID NO: 3);
I306A (in the AT domain on SEQ ID NO: 2), R130K (in the MPT domain on SEQ ID NO: 1), G236S and N258A (in the KS domain on SEQ ID NO: 3);
I306A (in the AT domain on SEQ ID NO: 2), R130K (in the MPT domain on SEQ ID NO: 1), G236S, M237W and N258A (in the KS domain on SEQ ID NO: 3);
I306A (in the AT domain on SEQ ID NO: 2), R130K (in the MPT domain on SEQ ID NO: 1), G236S and N258D (in the KS domain on SEQ ID NO: 3);
I306A (in the AT domain on SEQ ID NO: 2), R130K (in the MPT domain on SEQ ID NO: 1), G236S, M237W and N258D (in the KS domain on SEQ ID NO: 3);
I306A (in the AT domain on SEQ ID NO: 2), R130K (in the MPT domain on SEQ ID NO: 1), G236S and Q193A (in the KS domain on SEQ ID NO: 3);
I306A (in the AT domain on SEQ ID NO: 2), R130K (in the MPT domain on SEQ ID NO: 1), G236S, M237W and Q193A (in the KS domain on SEQ ID NO: 3);
I306A (in the AT domain on SEQ ID NO: 2), R130K (in the MPT domain on SEQ ID NO: 1), G236S and Q193E (in the KS domain on SEQ ID NO: 3);
I306A (in the AT domain on SEQ ID NO: 2), R130K (in the MPT domain on SEQ ID NO: 1), G236S, M237W and Q193E (in the KS domain on SEQ ID NO: 3);
preferably selected from
I306A (in the AT domain on SEQ ID NO: 2), R130K (in the MPT domain on SEQ ID NO: 1) and F265Y (in the KS domain on SEQ ID NO: 3)
R130K (in the MPT domain on SEQ ID NO: 1);
I306A (in the AT domain on SEQ ID NO: 2), R130K (in the MPT domain on SEQ ID NO: 1), G236S and M237W (in the KS domain on SEQ ID NO: 3);
R130K (in the MPT domain on SEQ ID NO: 1) and G236S (in the KS domain on SEQ ID NO: 3);
I306A (in the AT domain on SEQ ID NO: 2) and R130K (in the MPT domain on SEQ ID NO: 1);
G236S and M237W (in the KS domain on SEQ ID NO: 3);
I306A (in the AT domain on SEQ ID NO: 2), R130K (in the MPT domain on SEQ ID NO: 1) and G236S (in the KS domain on SEQ ID NO: 3);
I306A (in the AT domain on SEQ ID NO: 2), G236S and M237W (in the KS domain on SEQ ID NO: 3);
R130K (in the MPT domain on SEQ ID NO: 1), G236S and M237W (in the KS domain on SEQ ID NO: 3);
increase(s) the selectivity for the production of $C_8$ fatty acids, $C_8$ fatty acid CoA esters, $C_8$ fatty acid ethyl esters, $C_8$ fatty acid esters with other metabolites, and/or enzyme bound $C_8$ fatty acids compared to wild type polypeptide(s) or the polypeptide without such amino acid substitution(s).

Namely, proteins or polypeptides of the present invention, wherein the amino acid substitution(s) is/are selected from
I306A, R130K and F265Y;
R130K;
I306A, R130K, G236S and M237W;
R130K and G236S;
I306A and R130K;
G236S and M237W;
I306A, R130K and G236S;
I306A, G236S and M237W;
R130K, G236S and M237W;
I306A and F265Y;
M237W;
I306A, G236S and F265Y;
G236S and F265Y;
I306A and G236S;
R130K, G236S and F265Y;
I306A, R130K, G236S and F265Y;
I306A, G236S, M237W and F265Y;
I306A;
F265Y;
I306A and M237W;
R130K and M237W;
R130K and F265Y;
I306A, R130K and M237W;
I306A, M237W and F265Y;
R130K, M237W and F265Y;
G236S, M237W and F265Y;
M237W and F265Y;
I306A, R130K, M237W and F265Y;
R130K, G236S, M237W and F265Y;
I306A, R130K, G236S, M237W and F265Y;
I306A, R130K, G236S and D259A,
I306A, R130K, G236S and N258A;
I306A, R130K, G236S and N258D;
I306A, R130K, G236S and Q193A;
I306A, R130K, G236S and Q193E;
I306A, R130K, G236S, M237W and D259A;
I306A, R130K, G236S, M237W and N258A;
I306A, R130K, G236S, M237W and N258D;
I306A, R130K, G236S, M237W and Q193A; and
I306A, R130K, G236S, M237W and Q193E;
preferably selected from
I306A, R130K and F265Y;
R130K;
I306A, R130K, G236S and M237W;

R130K and G236S;
I306A and R130K;
G236S and M237W
I306A, R130K and G236S;
I306A, G236S and M237W;
R130K, G236S and M237W;
more preferably selected from
I306A, R130K and F265Y;
R130K;
I306A, R130K, G236S and M237W;
R130K and G236S;
I306A and R130K;
G236S and M237W;
I306A, R130K and G236S;
increase(s) the selectivity for the production of $C_8$ fatty acids, $C_8$ fatty acid CoA esters, $C_8$ fatty acid ethyl esters, $C_8$ fatty acid esters with other metabolites, and/or enzyme bound $C_8$ fatty acids compared to wild type polypeptide(s) or the polypeptide without such amino acid substitution(s).

Variants with Increased Selectivity for C10 to C12

In a preferred embodiment, the protein (s) or polypeptide(s) of the present invention show(s) an increased selectivity for the production of $C_{10}$ to $C_{12}$ fatty acids, $C_{10}$ to $C_{12}$ fatty acid CoA esters, $C_{10}$ to $C_{12}$ fatty acid ethyl esters, $C_{10}$ to $C_{12}$ fatty acid esters with other metabolites, and/or enzyme bound $C_{10}$ to $C_{12}$ fatty acids compared to wild type polypeptide(s) or the polypeptide without such amino acid substitution(s).

In particular, proteins or polypeptides of the present invention, wherein the amino acid substitution(s) is/are selected from I306A (in the AT domain on SEQ ID NO: 2), R130K (in the MPT domain on SEQ ID NO: 1), G236S and M237W (in the KS domain on SEQ ID NO: 3);
G236S and M237W (in the KS domain on SEQ ID NO: 3);
R130K (in the MPT domain on SEQ ID NO: 1);
I306A (in the AT domain on SEQ ID NO: 2), G236S and F265Y (in the KS domain on SEQ ID NO: 3);
I306A (in the AT domain on SEQ ID NO: 2), R130K (in the MPT domain on SEQ ID NO: 1) and G236S (in the KS domain on SEQ ID NO: 3);
R130K (in the MPT domain on SEQ ID NO: 1) and G236S (in the KS domain on SEQ ID NO: 3);
I306A (in the AT domain on SEQ ID NO: 2) and R130K (in the MPT domain on SEQ ID NO: 1);
I306A (in the AT domain on SEQ ID NO: 2), G236S and M237W (in the KS domain on SEQ ID NO: 3);
I306A (in the AT domain on SEQ ID NO: 2) and F265Y (in the KS domain on SEQ ID NO: 3);
M237W (in the KS domain on SEQ ID NO: 3);
I306A (in the AT domain on SEQ ID NO: 2), R130K (in the MPT domain on SEQ ID NO: 1) and F265Y (in the KS domain on SEQ ID NO: 3);
R130K (in the MPT domain on SEQ ID NO: 1), G236S and M237W (in the KS domain on SEQ ID NO: 3);
G236S and F265Y (in the KS domain on SEQ ID NO: 3);
I306A (in the AT domain on SEQ ID NO: 2) and G236S (in the KS domain on SEQ ID NO: 3);
R130K (in the MPT domain on SEQ ID NO: 1), G236S and F265Y (in the KS domain on SEQ ID NO: 3);
I306A (in the AT domain on SEQ ID NO: 2), R130K (in the MPT domain on SEQ ID NO: 1), G236S and F265Y (in the KS domain on SEQ ID NO: 3);
I306A (in the AT domain on SEQ ID NO: 2), G236S, M237W and F265Y (in the KS domain on SEQ ID NO: 3);
I306A (in the AT domain on SEQ ID NO: 2);
F265Y (in the KS domain on SEQ ID NO: 3);
I306A (in the AT domain on SEQ ID NO: 2) and M237W (in the KS domain on SEQ ID NO: 3);
R130K (in the MPT domain on SEQ ID NO: 1) and M237W (in the KS domain on SEQ ID NO: 3);
R130K (in the MPT domain on SEQ ID NO: 1) and F265Y (in the KS domain on SEQ ID NO: 3);
I306A (in the AT domain on SEQ ID NO: 2), R130K (in the MPT domain on SEQ ID NO: 1) and M237W (in the KS domain on SEQ ID NO: 3);
I306A (in the AT domain on SEQ ID NO: 2), M237W and F265Y (in the KS domain on SEQ ID NO: 3);
R130K (in the MPT domain on SEQ ID NO: 1), M237W and F265Y (in the KS domain on SEQ ID NO: 3);
G236S, M237W and F265Y (in the KS domain on SEQ ID NO: 3);
M237W and F265Y (in the KS domain on SEQ ID NO: 3);
I306A (in the AT domain on SEQ ID NO: 2), R130K (in the MPT domain on SEQ ID NO: 1), M237W and F265Y (in the KS domain on SEQ ID NO: 3);
R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S and D259A (in the KS domain on SEQ ID NO: 3);
I306A (in the AT domain on SEQ ID NO: 2), R130K (in the MPT domain on SEQ ID NO: 1), G236S, M237W and D259A (in the KS domain on SEQ ID NO: 3);
I306A (in the AT domain on SEQ ID NO: 2), R130K (in the MPT domain on SEQ ID NO: 1), G236S and N258A (in the KS domain on SEQ ID NO: 3);
I306A (in the AT domain on SEQ ID NO: 2), R130K (in the MPT domain on SEQ ID NO: 1), G236S, M237W and N258A (in the KS domain on SEQ ID NO: 3);
I306A (in the AT domain on SEQ ID NO: 2), R130K (in the MPT domain on SEQ ID NO: 1), G236S and N258D (in the KS domain on SEQ ID NO: 3);
I306A (in the AT domain on SEQ ID NO: 2), R130K (in the MPT domain on SEQ ID NO: 1), G236S, M237W and N258D (in the KS domain on SEQ ID NO: 3);
I306A (in the AT domain on SEQ ID NO: 2), R130K (in the MPT domain on SEQ ID NO: 1), G236S and Q193A (in the KS domain on SEQ ID NO: 3);
I306A (in the AT domain on SEQ ID NO: 2), R130K (in the MPT domain on SEQ ID NO: 1), G236S, M237W and Q193A (in the KS domain on SEQ ID NO: 3);
I306A (in the AT domain on SEQ ID NO: 2), R130K (in the MPT domain on SEQ ID NO: 1), G236S and Q193E (in the KS domain on SEQ ID NO: 3);
I306A (in the AT domain on SEQ ID NO: 2), R130K (in the MPT domain on SEQ ID NO: 1), G236S, M237W and Q193E (in the KS domain on SEQ ID NO: 3);
preferably selected from
I306A (in the AT domain on SEQ ID NO: 2), R130K (in the MPT domain on SEQ ID NO: 1), G236S and M237W (in the KS domain on SEQ ID NO: 3);
G236S and M237W (in the KS domain on SEQ ID NO: 3); R130K (in the MPT domain on SEQ ID NO: 1);
increase(s) the selectivity for the production of $C_{10}$ to $C_{12}$ fatty acids, $C_{10}$ to $C_{12}$ fatty acid CoA esters, $C_{10}$ to $C_{12}$ fatty acid ethyl esters, $C_{10}$ to $C_{12}$ fatty acid esters with other metabolites, and/or enzyme bound $C_{10}$ to $C_{12}$ fatty acids compared to wild type polypeptide(s) or the polypeptide without such amino acid substitution(s).

Namely, proteins or polypeptides of the present invention, wherein the amino acid substitution(s) is/are selected from
I306A, R130K, G236S and M237W;
G236S and M237W;
R130K;
I306A, G236S and F265Y;
I306A, R130K and G236S;
R130K and G236S;
I306A and R130K;
I306A, G236S and M237W;
I306A and F265Y;
I306A, R130K and G236S;
M237W;
I306A, R130K and F265Y;
R130K, G236S and M237W;
G236S and F265Y;
I306A and G236S;
R130K, G236S and F265Y;
I306A, R130K, G236S and F265Y;
I306A, G236S, M237W and F265Y;
I306A;
F265Y;
I306A and M237W;
R130K and M237W;
R130K and F265Y;
I306A, R130K and M237W;
I306A, M237W and F265Y;
R130K, M237W and F265Y;
G236S, M237W and F265Y;
M237W and F265Y;
I306A, R130K, M237W and F265Y;
R130K, G236S, M237W and F265Y;
I306A, R130K, G236S, M237W and F265Y;
I306A, R130K, G236S and D259A,
I306A, R130K, G236S and N258A;
I306A, R130K, G236S and N258D;
I306A, R130K, G236S and Q193A;
I306A, R130K, G236S and Q193E;
I306A, R130K, G236S, M237W and D259A;
I306A, R130K, G236S, M237W and N258A;
I306A, R130K, G236S, M237W and N258D;
I306A, R130K, G236S, M237W and Q193A; and
I306A, R130K, G236S, M237W and Q193E;
preferably selected from
I306A, R130K, G236S and M237W
G236S and M237W
R130K
increase(s) the selectivity for the production of $C_{10}$ to $C_{12}$ fatty acids, $C_{10}$ to $C_{12}$ fatty acid CoA esters, $C_{10}$ to $C_{12}$ fatty acid ethyl esters, $C_{10}$ to $C_{12}$ fatty acid esters with other metabolites, and/or enzyme bound $C_{10}$ to $C_{12}$ fatty acids compared to wild type polypeptide(s) or the polypeptide without such amino acid substitution(s).

Nucleic Acid Molecules

As discussed above, the present invention provides a nucleic acid molecule, coding for a protein or polypeptide according to the present invention.

As discussed above, the present invention provides nucleic acid molecules, coding for the proteins or polypeptides according to the present invention.

As discussed above, the present invention provides a nucleic acid molecule, coding for a domain or subunit of a polypeptide/protein according to the present invention.

Preferably the nucleic acid molecules of the invention comprise or consist of the nucleic acid sequences of SEQ ID NO: 4 coding for the MPT domain (with polypeptide sequence SEQ ID NO: 1), SEQ ID NO: 5 coding for the AT domain (with polypeptide sequence SEQ ID NO: 2) and/or SEQ ID NO: 6 coding for the KS domain (with polypeptide sequence SEQ ID NO: 3),
which comprise the respective nucleotide exchanges which lead to the amino acid substitution(s) of the present invention.

SEQ ID NO. 4 shows the nucleic acid sequence (part of GenBank: M30162.1 and J03936.1, split indicated by *) coding for the MPT domain (SEQ ID NO: 1):

```
TCTATCTTAGACATTGTCATTAACAACCCAGTTAACTTAACAATTCACTT

CGGTGGTGAAAAGGGTAAGAGGATCAGAGAAAACTATTCTGCTATGATCT

TTGAGACTATCGTGGATGGAAAATTGAAGACTGAAAAAATTTTCAAGGAA

ATTAATGAGCACAGTACTTCTTACACATTTAGATCTGAAAAAGGTTTATT

GTCTGCTACTCAATTTACACAACCAGCTTTAACTTTGATGGAAAAAGCTG

CTTTCGAAGACTTGAAATCTAAAGGTTTGATCCCAGCCGATGCTACTTTT

GCTGGTCACTCTTTAGGTGAGTATGCTGCTTTGGCCTCTTTGGCTGATGT

TATGTCTATCGAATCTTTAGTTGAAGTTGTGTTCTACAGAGGTATGACTA

TGCAAGTTGCTGTTCCAAGAGATGAGTTGGGCAGATCCAACTATGGTATG

ATTGCCATTAACCCAGGTAGAGTCGCTGCATCATTCTCTCAAGAAGCTTT

GCAATATGTTGTTGAGAGAGTTGGTAAGAGAACCGGCTGGTTGGTTGAAA

TCGTCAACTACAACGTTGAAAACCAACAATATGTTGCAGCTGGTGATCTA

AGAGCTTTAGACACCGTTACCAATGTTCTAAACTTCATCAAATTACAAAA

AATTGATATTATTGAACTACAAAAGTCCTTATCTTTGGAAGAAGTTGAAG

GTCATTTGTTTGAGATCATTGACGAAGCTTCCAAGAAATCTGCTGTCAAG

CCTCGCCCACTTAAATTGGAGAGAGGTTTTGCTTGTATCCCATTAGTTGG

TATTTCTGTTCCTTTCCATTCCACCTACTTGATGAATGGTGTTAAACCAT

TCAAGAGTTTCTTGAAGAAGAATATCATAAAAGAAAATGTGAAGGTTGCT

AGATTGGCCGGAAAGTACATTCCAAACTTGACTGCAAAACCATTCCAGGT

TACTAAGGAATATTTCCAGGACGTTTATGATTTGACTGGCTCCGAACCTA

TCAAGGAAATCATCGACAACTGGGAAAAGTATGAACAATCC*

ATGAAGCCGGAAGTTGAGCAAGAATTAGCTCATATTTTGCTAACTGAATT

GTTAGCTTATCAATTTGCCTCTCCTGTGAGATGGATTGAAACTCAAGATG

TTTTTTTGAAGGATTTTAACACTGAAAGGGTTGTTGAAATCGGTCCTTCT

CCAACTTTGGCTGGGATGGCTCAAAGAACCTTGAAGAATAAATACGAATC

TTACGATGCTGCTCTGTCTTTACATAGAGAAATCTTATGCTATTCG
```

SEQ ID NO: 5 shows the nucleic acid sequence (part of GenBank: M30162.1) coding for the AT domain (SEQ ID NO: 2)

```
ATGGACGCTTACTCCACAAGACCATTAACCCTATCTCACGGTTCTTTAGAG

CACGTGCTTCTGGTACCAACCGCTTCATTTTTCATTGCTTCGCAATTACAA

GAACAATTTAATAAAATTTTGCCCGAACCCACTGAAGGGTTTGCTGCAGAT
```

GACGAGCCTACCACACCTGCTGAACTAGTGGGGAAATTCCTTGGCTACGTA

TCTTCTCTAGTCGAACCTTCCAAGGTCGGTCAATTCGATCAGGTCTTGAAC

CTTTGCTTAACAGAATTTGAAAACTGTTATTTAGAAGGCAATGACATTCAC

GCCTTGGCTGCTAAACTATTACAGGAAAACGACACAACTTTAGTGAAGACT

AAAGAACTAATTAAAAATTATATTACCGCCAGAATAATGGCTAAGAGACCA

TTTGACAAAAAATCCAACTCTGCTCTTTTTAGGGCCGTCGGCGAGGGTAAC

GCACAATTGGTAGCCATTTTCGGTGGTCAAGGTAACACCGACGACTACTTT

GAAGAATTGCGTGATCTATATCAAACTTATCATGTCTTAGTGGGAGATTTA

ATCAAGTTCTCCGCTGAAACTTTAAGTGAACTGATTAGAACTACTTTAGAT

GCTGAAAAGTCTTTACTCAAGGTTTAAACATATTGGAATGGTTGGAGAAC

CCTTCAAATACCCCAGACAAGGACTATTTACTTTCCATTCCAATTTCATGC

CCCTTAATTGGTGTCATTCAATTGGCTCACTACGTAGTTACTGCCAAGCTT

TTGGGTTTCACTCCAGGTGAGTTAAGATCTTACTTAAAAGGTGCTACAGGT

CACTCTCAAGGTTTGGTTACTGCTGTCGCCATAGCTGAGACGGATTCCTGG

GAATCCTTCTTCGTCTCCGTAAGAAAAGCAATTACTGTATTATTCTTCATC

GGTGTTCGTTGTTACGAAGCATACCCAAACACTTCCCTACCACCATCCATC

TTGGAAGATTCCTTGGAAAACAATGAAGGTGTTCCATCTCCAATGTTGTCC

ATTTCCAATCTAACTCAAGAACAAGTTCAAGACTATGTAAATAAGACTAAC

TCTCATTTGCCAGCTGGTAAACAAGTTGAAATTTCTCTAGTCAATGGTGCG

AAGAATCTAGTCGTATCGGCCCACCACAATCATTATATGGTTTAAACTTG

ACTTTAAGAAAGGCCAAGGCCCCATCTGGACTGGATCAATCAAGAATCCCA

TTCAGCGAAAGAAAATTGAAGTTCTCCAATAGGTTCTTACCTGTTGCATCA

CCATTCCATTCCCATCTATTGGTTCCAGCTTCAGATTTGATTAACAAAGAC

TTAGTCAAAACAATGTCAGCTTTAACGCTAAAGATATTCAAATCCCCGTT

TACGACACTTTTGATGGTTCAGATCTAAGAGTCCTTTCAGGTTCCATTTCC

GAGAGAATCGTCGACTGCATCATTAGATTACCTGTCAAATGGGAAACTACT

ACACAATTCAAAGCCACCCACATATTGACTTTGGTCCAGGTGGAGCTTCC

GGTTTAGGTGTTTTAACCCATCGTAATAAAGATGGTACTGGTGTTCGTGTT

ATCGTTGCCGGTACTCTCGACATTAACCCAGATGATGATTACGGATTCAAG

CAAGAAATCTTTGATGTTACT

SEQ ID NO: 6 shows the nucleic acid sequence (part of GenBank: J03936.1) coding for the KS domain (SEQ ID NO: 3)

TTGGAAAGAGTTATTGTAGTTACCGGTTTTGCTGAAGTCGGCCCATGGGG

TTCGGCCAGAACAAGATGGGAAATGGAAGCTTTTGGTGAATTTTCGTTGG

AAGGTTGCGTTGAAATGGCCTGGATTATGGGCTTCATTTCATACCATAAC

GGTAATTTGAAGGGTCGTCCATACACTGGTTGGGTTGATTCCAAAACAAA

AGAACCAGTTGATGACAAGGACGTTAAGGCCAAGTATGAAACATCAATCC

TAGAACACAGTGGTATCAGATTGATCGAACCAGAGTTATTCAATGGTTAC

AACCCAGAAAAGAAGGAAATGATTCAAGAAGTCATTGTCGAAGAAGACTT

GGAACCATTTGAGGCTTCGAAGGAAACTGCCGAACAATTTAAACACCAAC

ATGGTGACAAAGTGGATATCTTCGAAATCCCAGAAACAGGAGAGTACTCT

GTTAAGTTACTAAAGGGTGCCACTTTATACATTCCAAAGGCTTTGAGATT

TGACCGTTTGGTTGCAGGTCAAATTCCAACTGGTTGGAATGCTAAGACTT

ATGGTATCTCTGATGATATCATTTCTCAGGTTGACCCAATCACATTATTC

GTTTTGGTCTCTGTTGTGGAAGCATTTATTGCATCTGGTATCACCGACCC

ATACGAAATGTACAAATACGTACATGTTTCTGAGGTTGGTAACTGTTCTG

GTTCTGGTATGGGTGGTGTTTCTGCCTTACGTGGTATGTTTAAGGACCGT

TTCAAGGATGAGCCTGTCCAAAATGATATTTTACAAGAATCATTTATCAA

CACCATGTCCGCTTGGGTTAATATGTTGTTGATTTCCTCATCTGGTCCAA

TCAAGACACCTGTTGGTGCCTGTGCCACATCCGTGGAATCTGTTGACATT

GGTGTAGAAACCATCTTGTCTGGTAAGGCTAGAATCTGTATTGTCGGTGG

TTACGATGATTTCCAAGAAGAAGGCTCCTTTGAGTTCGGTAACATGAAGG

CCACTTCCAACACTTTGGAAGAATTTGAACATGGTCGTACCCCAGCGGAA

ATGTCCAGACCTGCCACCACTACCCGTAACGGTTTTATGGAAGCTCAAGG

TGCTGGTATTCAAATCATCATGCAAGCTGATTTAGCTTTGAAGATGGGTG

TGCCAATTTACGGTATTGTTGCCATGGCTGCTACCGCCACCGATAAGATT

GGTAGATCTGTGCCAGCTCCAGGTAAGGGTATTTTAACCACTGCTCGTGA

ACACCACTCCAGTGTTAAGTATGCTTCACCAAACTTGAACATGAAGTACA

GAAAGCGCCAATTGGTTACTCGTGAAGCTCAGATTAAAGATTGGGTAGAA

AACGAATTGGAAGCTTTGAAGTTGGAGGCCGAAGAAATTCCAAGCGAAGA

CCAAAACGAGTTCTTACTTGAACGTACCAGAGAAATCCACAACGAAGCTG

AAAGTCAATTGAGAGCTGCACAACAACAATGGGGTAACGACTTCTACAAG

AGGGACCCACGTATTGCTCCATTGAGAGGAGCACTGGCTACTTACGGTTT

AACTATTGATGACTTGGGTGTCGCTTCATTCCACGGTACATCCACAAAGG

CTAATGACAAGAACGAATCTGCCACAATTAATGAAATGATGAAGCATTTG

GGTAGATCTGAAGGTAATCCCGTCATTGGTGTTTTCCAAAAGTTCTTGAC

TGGTCATCCAAAGGGTGCTGCTGGTGCATGGATGATGAATGGTGCTTTGC

AAATTCTAAACAGTGGTATTATTCCAGGTAACCGTAACGCTGATAACGTG

GATAAGATCTTGGAGCAATTTGAATACGTCTTGTACCCATCCAAGACTTT

AAAGACCGACGGTGTCAGAGCCGTGTCCATCACTTCTTTCGGTTTTGGTC

AAAAGGGTGGTCAAGCTATTGTGGTTCATCCAGACTACTTATACGGTGCT

In one embodiment, the nucleic acid molecule of the present invention further comprises:

vector nucleic acid sequences, preferably expression vector sequences, and/or promoter nucleic acid sequences and terminator nucleic acid sequences, and/or comprises other regulatory nucleic acid sequence.

In one embodiment, the nucleic acid molecule of the present invention comprises dsDNA, ssDNA, cDNA, LNA, PNA, CNA, RNA or mRNA or combinations thereof.

The nucleic acid molecules according to the invention preferably comprise nucleic acid sequences, which are (except for the addition of the amino acid substitution(s)

according to the invention) identical with the naturally occurring nucleic acid sequence or are codon-optimized for the use in a host cell.

The nucleic acid molecule used according to the present invention is preferably a nucleic acid expression construct.

Nucleic acid expression constructs according to the invention are expression cassettes comprising a nucleic acid molecule according to the invention, or expression vectors comprising a nucleic acid molecule according to the invention or an expression cassette, for example.

A nucleic acid expression construct preferably comprises regulatory sequences, such as promoter and terminator sequences, which are operatively linked with the nucleic acid sequence coding for the polypeptide(s) of the invention.

The nucleic acid expression construct may further comprise 5' and/or 3' recognition sequences and/or selection markers.

Host Cells

As discussed above, the present invention provides host cells containing a nucleic acid molecule according to the present invention.

Preferably, the host cells of the present invention express said nucleic acid molecule.

Preferably, a host cell according to the present invention is a bacterial cell.

The bacterial cell is more preferably a member of a genus selected from the group *Corynebacterium, Mycobacterium, Escherichia, Nocordia, Bacillus, Clostridium, Pseudomonas, Lactobacillus* or *Leuconostoc.*

The bacterial cell is more preferably a member of a species selected from the group of *Corynebacterium glutamicum, Escherichia coli, Bacillus subtilis; Clostridium ljungdahlii, Pseudomonas putida; Lactobacillus bifermentans* or *Leuconostoc mesenteroides.*

Preferably, a host cell according to the present invention is a fungus cell and more preferably a yeast cell.

The yeast cell is preferably a member of a genus selected from the group of *Saccharomyces* species, *Kluyveromyces* sp., *Hansenula* sp., *Arxula* sp., *Rhodosporidium* sp., *Pichia* sp. or *Yarrowia* sp.

The yeast cell is more preferably a member of a species selected from the group of *S. cerevisiae, S. bulderi, S. barnetti, S. exiguus, S. uvarum, S. diastaticus, K lactis, K marxianus, K fragilis, H. polymorpha, P. pastoris* and *Y. lipolytica*, such as *S. cerevisiae, K lactis, H. polymorpha, P. pastoris, K. marxianus,* or *Y. lipolytica.*

In a preferred embodiment, the host cell belongs to the species *Saccharomyces cerevisiae.*

Preferably, a host cell according to the present invention is an algae cell.

The algae cell is more preferably a member of a genus selected from the group *Chlamydomonas, Chlorella, Haematococcus, Dunaliella, Nannochloropsis, Thalassiosira, Phaeodactylum, Porphyridium* or *Scenedesmus*

The algae cell is more preferably a member of a species selected from the group of *Chlamydomonas reinhardtii* or *Haematococcus pluvialis.*

Preferably, the host cell (preferably yeast cell) has an elevated overall production of short fatty acids, CoA esters of short fatty acids, ethyl esters of short fatty acids, esters of short fatty acids with other metabolites, and/or enzyme bound short fatty acids ($C_6$ to $C_{12}$) compared to a cell not containing a nucleic acid molecule according to the present invention.

In a preferred embodiment, the host cell has an increased yield or increased selectivity in the production of $C_6$ fatty acids, $C_6$ fatty acid CoA esters, $C_6$ fatty acid ethyl esters, $C_6$ fatty acid esters with other metabolites, and/or enzyme bound $C_6$ fatty acids compared to a cell not containing a nucleic acid molecule according to the present invention.

The selectivity for the production of $C_6$ fatty acids, $C_6$ CoA esters and/or enzyme bound $C_6$ fatty acids compared to wild type is increased where the share of $C_6$ makes up at least 30%, or preferably at least 40% or 50% or 70% or 80% or 90% of the detected chain length between $C_6$ and $C_{12}$.

As discussed above, in particular proteins or polypeptides of the present invention, wherein the amino acid substitution(s) is/are selected from I306A (in the AT domain on SEQ ID NO: 2) and G236S (in the KS domain on SEQ ID NO: 3);

I306A (in the AT domain on SEQ ID NO: 2) and F265Y (in the KS domain on SEQ ID NO: 3);

I306A (in the AT domain on SEQ ID NO: 2), G236S and M237W (in the KS domain on SEQ ID NO: 3);

I306A (in the AT domain on SEQ ID NO: 2), R130K (in the MPT domain on SEQ ID NO: 1) and G236S (in the KS domain on SEQ ID NO: 3);

G236S and M237W (in the KS domain on SEQ ID NO: 3);

I306A (in the AT domain on SEQ ID NO: 2), R130K (in the MPT domain on SEQ ID NO: 1), G236S and M237W (in the KS domain on SEQ ID NO: 3);

R130K (in the MPT domain on SEQ ID NO: 1);

I306A (in the AT domain on SEQ ID NO: 2), G236S and F265Y (in the KS domain on SEQ ID NO: 3);

I306A (in the AT domain on SEQ ID NO: 2), R130K (in the MPT domain on SEQ ID NO: 1) and F265Y (in the KS domain on SEQ ID NO: 3);

I306A (in the AT domain on SEQ ID NO: 2) and R130K (in the MPT domain on SEQ ID NO: 1);

R130K (in the MPT domain on SEQ ID NO: 1) and G236S (in the KS domain on SEQ ID NO: 3);

R130K (in the MPT domain on SEQ ID NO: 1), G236S and M237W (in the KS domain on SEQ ID NO: 3);

G236S and F265Y (in the KS domain on SEQ ID NO: 3);

R130K (in the MPT domain on SEQ ID NO: 1), G236S and F265Y (in the KS domain on SEQ ID NO: 3);

I306A (in the AT domain on SEQ ID NO: 2), R130K (in the MPT domain on SEQ ID NO: 1), G236S and F265Y (in the KS domain on SEQ ID NO: 3);

I306A (in the AT domain on SEQ ID NO: 2), G236S, M237W and F265Y (in the KS domain on SEQ ID NO: 3);

I306A (in the AT domain on SEQ ID NO: 2);

M237W (in the KS domain on SEQ ID NO: 3);

F265Y (in the KS domain on SEQ ID NO: 3);

I306A (in the AT domain on SEQ ID NO: 2) and M237W (in the KS domain on SEQ ID NO: 3);

R130K (in the MPT domain on SEQ ID NO: 1) and M237W (in the KS domain on SEQ ID NO: 3);

R130K (in the MPT domain on SEQ ID NO: 1) and F265Y (in the KS domain on SEQ ID NO: 3);

I306A (in the AT domain on SEQ ID NO: 2), R130K (in the MPT domain on SEQ ID NO: 1) and M237W (in the KS domain on SEQ ID NO: 3);

I306A (in the AT domain on SEQ ID NO: 2), M237W and F265Y (in the KS domain on SEQ ID NO: 3);

R130K (in the MPT domain on SEQ ID NO: 1), M237W and F265Y (in the KS domain on SEQ ID NO: 3);

G236S, M237W and F265Y (in the KS domain on SEQ ID NO: 3);

M237W and F265Y (in the KS domain on SEQ ID NO: 3);

I306A (in the AT domain on SEQ ID NO: 2), R130K (in the MPT domain on SEQ ID NO: 1), M237W and F265Y (in the KS domain on SEQ ID NO: 3);

R130K (in the MPT domain on SEQ ID NO: 1), G236S, M237W and F265Y (in the KS domain on SEQ ID NO: 3);

I306A (in the AT domain on SEQ ID NO: 2), R130K (in the MPT domain on SEQ ID NO: 1), G236S, M237W and F265Y (in the KS domain on SEQ ID NO: 3);

I306A (in the AT domain on SEQ ID NO: 2), R130K (in the MPT domain on SEQ ID NO: 1), G236S and N258A (in the KS domain on SEQ ID NO: 3);

I306A (in the AT domain on SEQ ID NO: 2), R130K (in the MPT domain on SEQ ID NO: 1), G236S and N258D (in the KS domain on SEQ ID NO: 3);

I306A (in the AT domain on SEQ ID NO: 2), R130K (in the MPT domain on SEQ ID NO: 1), G236S, M237W and N258A (in the KS domain on SEQ ID NO: 3);

I306A (in the AT domain on SEQ ID NO: 2), R130K (in the MPT domain on SEQ ID NO: 1), G236S, M237W and N258D (in the KS domain on SEQ ID NO: 3);

preferably selected from

I306A (in the AT domain on SEQ ID NO: 2) and G236S (in the KS domain on SEQ ID NO: 3);

I306A (in the AT domain on SEQ ID NO: 2) and F265Y (in the KS domain on SEQ ID NO: 3);

I306A (in the AT domain on SEQ ID NO: 2), G236S and M237W (in the KS domain on SEQ ID NO: 3);

I306A (in the AT domain on SEQ ID NO: 2), R130K (in the MPT domain on SEQ ID NO: 1) and G236S (in the KS domain on SEQ ID NO: 3)

G236S and M237W (in the KS domain on SEQ ID NO: 3), more preferably

I306A and G236S,

I306A and F265Y,

I306A, G236S and M237W,

I306A, R130K and G236S, increase(s) the selectivity for the production of $C_6$ fatty acids, $C_6$ CoA, $C_6$ fatty acid ethyl esters, $C_6$ fatty acid esters with other metabolites, esters and/or enzyme bound $C_6$ fatty acids compared to wild type polypeptide(s) or the polypeptide without such amino acid substitution(s).

In a preferred embodiment, the host cell has an increased yield or increased selectivity in the production of $C_8$ fatty acids, $C_8$ fatty acid CoA esters, $C_8$ fatty acid ethyl esters, $C_8$ fatty acid esters with other metabolites, and/or enzyme bound $C_8$ fatty acids compared to a cell not containing a nucleic acid molecule according to the present invention.

The selectivity for the production of $C_8$ fatty acids, $C_8$ CoA esters and/or enzyme bound $C_8$ fatty acids compared to wild type is increased where the share of $C_8$ makes up at least 30%, or preferably at least 40% or 50% or 70% or 80% or 89% of the detected chain length between $C_6$ and $C_{12}$.

As discussed above, in particular proteins or polypeptides of the present invention, wherein the amino acid substitution(s) is/are selected from I306A (in the AT domain on SEQ ID NO: 2), R130K (in the MPT domain on SEQ ID NO: 1) and F265Y (in the KS domain on SEQ ID NO: 3)

R130K (in the MPT domain on SEQ ID NO: 1);

I306A (in the AT domain on SEQ ID NO: 2), R130K (in the MPT domain on SEQ ID NO: 1), G236S and M237W (in the KS domain on SEQ ID NO: 3);

R130K (in the MPT domain on SEQ ID NO: 1) and G236S (in the KS domain on SEQ ID NO: 3);

I306A (in the AT domain on SEQ ID NO: 2) and R130K (in the MPT domain on SEQ ID NO: 1);

G236S and M237W (in the KS domain on SEQ ID NO: 3);

I306A (in the AT domain on SEQ ID NO: 2), R130K (in the MPT domain on SEQ ID NO: 1) and G236S (in the KS domain on SEQ ID NO: 3);

I306A (in the AT domain on SEQ ID NO: 2), G236S and M237W (in the KS domain on SEQ ID NO: 3);

R130K (in the MPT domain on SEQ ID NO: 1), G236S and M237W (in the KS domain on SEQ ID NO: 3);

I306A (in the AT domain on SEQ ID NO: 2) and F265Y (in the KS domain on SEQ ID NO: 3);

M237W (in the KS domain on SEQ ID NO: 3);

I306A (in the AT domain on SEQ ID NO: 2), G236S and F265Y (in the KS domain on SEQ ID NO: 3);

G236S and F265Y (in the KS domain on SEQ ID NO: 3);

I306A (in the AT domain on SEQ ID NO: 2) and G236S (in the KS domain on SEQ ID NO: 3);

R130K (in the MPT domain on SEQ ID NO: 1), G236S and F265Y (in the KS domain on SEQ ID NO: 3)

I306A (in the AT domain on SEQ ID NO: 2), R130K (in the MPT domain on SEQ ID NO: 1), G236S and F265Y (in the KS domain on SEQ ID NO: 3);

I306A (in the AT domain on SEQ ID NO: 2), G236S, M237W and F265Y (in the KS domain on SEQ ID NO: 3);

I306A (in the AT domain on SEQ ID NO: 2);

F265Y (in the KS domain on SEQ ID NO: 3);

I306A (in the AT domain on SEQ ID NO: 2) and M237W (in the KS domain on SEQ ID NO: 3);

R130K (in the MPT domain on SEQ ID NO: 1) and M237W (in the KS domain on SEQ ID NO: 3);

R130K (in the MPT domain on SEQ ID NO: 1) and F265Y (in the KS domain on SEQ ID NO: 3);

I306A (in the AT domain on SEQ ID NO: 2), R130K (in the MPT domain on SEQ ID NO: 1) and M237W (in the KS domain on SEQ ID NO: 3);

I306A (in the AT domain on SEQ ID NO: 2), M237W and F265Y (in the KS domain on SEQ ID NO: 3);

R130K (in the MPT domain on SEQ ID NO: 1), M237W and F265Y (in the KS domain on SEQ ID NO: 3);

G236S, M237W and F265Y (in the KS domain on SEQ ID NO: 3);

M237W and F265Y (in the KS domain on SEQ ID NO: 3);

I306A (in the AT domain on SEQ ID NO: 2), R130K (in the MPT domain on SEQ ID NO: 1), M237W and F265Y (in the KS domain on SEQ ID NO: 3);

R130K (in the MPT domain on SEQ ID NO: 1), G236S, M237W and F265Y (in the KS domain on SEQ ID NO: 3);

I306A (in the AT domain on SEQ ID NO: 2), R130K (in the MPT domain on SEQ ID NO: 1), G236S, M237W and F265Y (in the KS domain on SEQ ID NO: 3);

I306A (in the AT domain on SEQ ID NO: 2), R130K (in the MPT domain on SEQ ID NO: I), G236S and D259A (in the KS domain on SEQ ID NO: 3);

I306A (in the AT domain on SEQ ID NO: 2), R130K (in the MPT domain on SEQ ID NO: 1), G236S, M237W and D259A (in the KS domain on SEQ ID NO: 3);

I306A (in the AT domain on SEQ ID NO: 2), R130K (in the MPT domain on SEQ ID NO: 1), G236S and N258A (in the KS domain on SEQ ID NO: 3);

I306A (in the AT domain on SEQ ID NO: 2), R130K (in the MPT domain on SEQ ID NO: 1), G236S, M237W and N258A (in the KS domain on SEQ ID NO: 3);

I306A (in the AT domain on SEQ ID NO: 2), R130K (in the MPT domain on SEQ ID NO: 1), G236S and N258D (in the KS domain on SEQ ID NO: 3);
I306A (in the AT domain on SEQ ID NO: 2), R130K (in the MPT domain on SEQ ID NO: 1), G236S, M237W and N258D (in the KS domain on SEQ ID NO: 3);
I306A (in the AT domain on SEQ ID NO: 2), R130K (in the MPT domain on SEQ ID NO: 1), G236S and Q193A (in the KS domain on SEQ ID NO: 3);
I306A (in the AT domain on SEQ ID NO: 2), R130K (in the MPT domain on SEQ ID NO: 1), G236S, M237W and Q193A (in the KS domain on SEQ ID NO: 3);
I306A (in the AT domain on SEQ ID NO: 2), R130K (in the MPT domain on SEQ ID NO: 1), G236S and Q193E (in the KS domain on SEQ ID NO: 3);
I306A (in the AT domain on SEQ ID NO: 2), R130K (in the MPT domain on SEQ ID NO: 1), G236S, M237W and Q193E (in the KS domain on SEQ ID NO: 3);
preferably selected from
I306A (in the AT domain on SEQ ID NO: 2), R130K (in the MPT domain on SEQ ID NO: 1) and F265Y (in the KS domain on SEQ ID NO: 3)
R130K (in the MPT domain on SEQ ID NO: 1);
I306A (in the AT domain on SEQ ID NO: 2), R130K (in the MPT domain on SEQ ID NO: 1), G236S and M237W (in the KS domain on SEQ ID NO: 3);
R130K (in the MPT domain on SEQ ID NO: 1) and G236S (in the KS domain on SEQ ID NO: 3);
I306A (in the AT domain on SEQ ID NO: 2) and R130K (in the MPT domain on SEQ ID NO: 1);
G236S and M237W (in the KS domain on SEQ ID NO: 3);
I306A (in the AT domain on SEQ ID NO: 2), R130K (in the MPT domain on SEQ ID NO: 1) and G236S (in the KS domain on SEQ ID NO: 3);
I306A (in the AT domain on SEQ ID NO: 2), G236S and M237W (in the KS domain on SEQ ID NO: 3);
R130K (in the MPT domain on SEQ ID NO: 1), G236S and M237W (in the KS domain on SEQ ID NO: 3);
more preferably,
I306A, R130K and F265Y;
R130K;
I306A, R130K, G236S and M237W;
R130K and G236S;
I306A and R130K;
G236S and M237W;
I306A, R130K and G236S;
increase(s) the selectivity for the production of $C_8$ fatty acids, $C_8$ fatty acid CoA esters, $C_8$ fatty acid ethyl esters, $C_8$ fatty acid esters with other metabolites, and/or enzyme bound $C_8$ fatty acids compared to wild type polypeptide(s) or the polypeptide without such amino acid substitution(s).

In a preferred embodiment, the host cell has an increased yield or increased selectivity in the production of $C_{10}$ to $C_{12}$ fatty acids, $C_{10}$ to $C_{12}$ fatty acid CoA esters, $C_{10}$ to $C_{12}$ fatty acid ethyl esters, $C_{10}$ to $C_{12}$ fatty acid esters with other metabolites, and/or enzyme bound $C_{10}$ to $C_{12}$ fatty acids compared to a cell not containing a nucleic acid molecule according to the present invention.

As discussed above, in particular proteins or polypeptides of the present invention, wherein the amino acid substitution(s) is/are selected from
I306A (in the AT domain on SEQ ID NO: 2), R130K (in the MPT domain on SEQ ID NO: 1), G236S and M237W (in the KS domain on SEQ ID NO: 3);
G236S and M237W (in the KS domain on SEQ ID NO: 3);
R130K (in the MPT domain on SEQ ID NO: 1);
I306A (in the AT domain on SEQ ID NO: 2), G236S and F265Y (in the KS domain on SEQ ID NO: 3);
I306A (in the AT domain on SEQ ID NO: 2), RI30K (in the MPT domain on SEQ ID NO: 1) and G236S (in the KS domain on SEQ ID NO: 3);
R130K (in the MPT domain on SEQ ID NO: 1) and G236S (in the KS domain on SEQ ID NO: 3);
I306A (in the AT domain on SEQ ID NO: 2) and R130K (in the MPT domain on SEQ ID NO: 1);
I306A (in the AT domain on SEQ ID NO: 2), G236S and M237W (in the KS domain on SEQ ID NO: 3);
I306A (in the AT domain on SEQ ID NO: 2) and F265Y (in the KS domain on SEQ ID NO: 3);
M237W (in the KS domain on SEQ ID NO: 3);
I306A (in the AT domain on SEQ ID NO: 2), R130K (in the MPT domain on SEQ ID NO: 1) and F265Y (in the KS domain on SEQ ID NO: 3);
R130K (in the MPT domain on SEQ ID NO: 1), G236S and M237W (in the KS domain on SEQ ID NO: 3);
G236S and F265Y (in the KS domain on SEQ ID NO: 3);
I306A (in the AT domain on SEQ ID NO: 2) and G236S (in the KS domain on SEQ ID NO: 3);
R130K (in the MPT domain on SEQ ID NO: 1), G236S and F265Y (in the KS domain on SEQ ID NO: 3);
I306A (in the AT domain on SEQ ID NO: 2), R130K (in the MPT domain on SEQ ID NO: 1), G236S and F265Y (in the KS domain on SEQ ID NO: 3);
I306A (in the AT domain on SEQ ID NO: 2), G236S, M237W and F265Y (in the KS domain on SEQ ID NO: 3);
I306A (in the AT domain on SEQ ID NO: 2);
F265Y (in the KS domain on SEQ ID NO: 3);
I306A (in the AT domain on SEQ ID NO: 2) and M237W (in the KS domain on SEQ ID NO: 3);
R130K (in the MPT domain on SEQ ID NO: 1) and M237W (in the KS domain on SEQ ID NO: 3);
R130K (in the MPT domain on SEQ ID NO: 1) and F265Y (in the KS domain on SEQ ID NO: 3);
I306A (in the AT domain on SEQ ID NO: 2), R130K (in the MPT domain on SEQ ID NO: 1) and M237W (in the KS domain on SEQ ID NO: 3);
I306A (in the AT domain on SEQ ID NO: 2), M237W and F265Y (in the KS domain on SEQ ID NO: 3);
R130K (in the MPT domain on SEQ ID NO: 1), M237W and F265Y (in the KS domain on SEQ ID NO: 3);
G236S, M237W and F265Y (in the KS domain on SEQ ID NO: 3);
M237W and F265Y (in the KS domain on SEQ ID NO: 3);
I306A (in the AT domain on SEQ ID NO: 2), R130K (in the MPT domain on SEQ ID NO: 1), M237W and F265Y (in the KS domain on SEQ ID NO: 3);
R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S, M237W and F265Y (in the KS domain on SEQ ID NO: 3);
I306A (in the AT domain on SEQ ID NO: 2), R130K (in the MPT domain on SEQ ID NO: 1), G236S and D259A (in the KS domain on SEQ ID NO: 3);
I306A (in the AT domain on SEQ ID NO: 2), R130K (in the MPT domain on SEQ ID NO: 1), G236S, M237W and D259A (in the KS domain on SEQ ID NO: 3);

I306A (in the AT domain on SEQ ID NO: 2), R130K (in the MPT domain on SEQ ID NO: 1), G236S and N258A (in the KS domain on SEQ ID NO: 3);
I306A (in the AT domain on SEQ ID NO: 2), R130K (in the MPT domain on SEQ ID NO: 1), G236S, M237W and N258A (in the KS domain on SEQ ID NO: 3);
I306A (in the AT domain on SEQ ID NO: 2), R130K (in the MPT domain on SEQ ID NO: 1), G236S and N258D (in the KS domain on SEQ ID NO: 3);
I306A (in the AT domain on SEQ ID NO: 2), R130K (in the MPT domain on SEQ ID NO: 1), G236S, M237W and N258D (in the KS domain on SEQ ID NO: 3);
I306A (in the AT domain on SEQ ID NO: 2), R130K (in the MPT domain on SEQ ID NO: 1), G236S and Q193A (in the KS domain on SEQ ID NO: 3);
I306A (in the AT domain on SEQ ID NO: 2), R130K (in the MPT domain on SEQ ID NO: 1), G236S, M237W and Q193A (in the KS domain on SEQ ID NO: 3);
I306A (in the AT domain on SEQ ID NO: 2), R130K (in the MPT domain on SEQ ID NO: 1), G236S and Q193E (in the KS domain on SEQ ID NO: 3);
I306A (in the AT domain on SEQ ID NO: 2), R130K (in the MPT domain on SEQ ID NO: 1), G236S, M237W and Q193E (in the KS domain on SEQ ID NO: 3);
preferably selected from
I306A (in the AT domain on SEQ ID NO: 2), R130K (in the MPT domain on SEQ ID NO: 1), G236S and M237W (in the KS domain on SEQ ID NO: 3);
G236S and M237W (in the KS domain on SEQ ID NO: 3);
R130K (in the MPT domain on SEQ ID NO: 1);
increase(s) the selectivity for the production of $C_{10}$ to $C_{12}$ fatty acids, $C_{10}$ to $C_{12}$ fatty acid CoA esters, $C_{10}$ to $C_{12}$ fatty acid ethyl esters, $C_{10}$ to $C_{12}$ fatty acid esters with other metabolites, and/or enzyme bound $C_{10}$ to $C_{12}$ fatty acids compared to wild type polypeptide(s) or the polypeptide without such amino acid substitution(s).

Methods and Uses for Producing Fatty Acids and/or Biofuels and/or Flavoring Substances and/or Fine Chemicals As discussed above, the present invention provides a method for the production of short fatty acids, CoA esters of short fatty acids, short fatty acid ethyl esters, short fatty acid esters with other metabolites, and/or enzyme bound short fatty acids ($C_6$ to $C_{12}$).

Said method comprises the expression of a nucleic acid molecule according to the present invention, preferably in a host cell according to the present invention.

As discussed above, the present invention provides a method for the production of
biofuels,
flavoring compounds or substances
and/or
fine chemicals.

Said method comprises the expression of a nucleic acid molecule according to the present invention, preferably in a host cell according to the present invention.

Biofuels which can be produced with the method are, for example, short alkanes, short alkenes, short alkynes, short esters or alcohols.

Flavoring compounds or substances which can be produced with the method are, for example, fatty acids esterified with short alcohols or esters from short fatty acids ($C_6$ to $C_{12}$).

Fine chemicals which can be produced with the method are, for example, natural compounds, where preferably short fatty acids ($C_6$ to $C_{12}$) or their derivatives (such as CoA esters, methyl/ethyl esters, esters with other metabolites, alcohols) are used as building block(s).

As discussed above, the present invention provides the use of
a protein or polypeptide according to the present invention,
a nucleic acid molecule according to the present invention, or
a host cell according to the present invention,
for
the bulk production of short fatty acids ($C_6$ to $C_{12}$), CoA esters of short fatty acids, short fatty acid ethyl esters, short fatty acid esters with other metabolites, enzyme bound short fatty acids; or
the specific production of short fatty acids ($C_6$ or $C_8$), $C_6$-CoA esters or $C_8$-CoA esters, fatty acid ($C_6$ or $C_8$) ethyl esters, fatty acid ($C_6$ or $C_8$) esters with other metabolites, enzyme bound short fatty acids ($C_6$ or $C_8$).

In particular, the present invention provides the use of a protein or polypeptide according to the present invention, a nucleic acid molecule according to the present invention, or a host cell according to the present invention, for
the bulk production of short fatty acids ($C_6$ to $C_{12}$),
the specific production of $C_6$ fatty acids,
the specific production of $C_8$ fatty acids,
the bulk production of CoA esters of short fatty acids ($C_6$ to $C_{12}$),
the specific production of $C_6$ fatty acid CoA esters,
the specific production of $C_8$ fatty acid CoA esters,
the bulk production of ethyl esters of short fatty acids ($C_6$ to $C_{12}$),
the specific production of $C_6$ fatty acid ethyl esters,
the specific production of $C_8$ fatty acid ethyl esters,
the bulk production of short fatty acids ($C_6$ to $C_{12}$) esters with other metabolites,
the specific production of $C_6$ fatty acid esters with other metabolites,
the specific production of $C_8$ fatty acid esters with other metabolites,
the bulk production of enzyme bound short fatty acids ($C_6$ to $C_{12}$),
the specific production of enzyme bound $C_6$ fatty acids, or
the specific production of enzyme bound $C_8$ fatty acids.

As discussed above, the present invention further provides the use of
a protein or polypeptide according to the present invention,
a nucleic acid molecule according to the present invention, or
a host cell according to the present invention,
for
the production of biofuels, such as short alkanes, short alkenes, short alkynes, short esters or alcohols,
the production of fine chemicals, such as natural compounds where preferably short fatty acids ($C_6$ to $C_{12}$) or their derivatives (such as CoA esters, methyl/ethyl esters, esters with other metabolites, alcohols) are used as building block(s), or
the production of flavoring compounds or substances, such as esters from short fatty acids ($C_6$ to $C_{12}$).

Further Description of Preferred Embodiments

The study shown here, is the first one reported where by rational design *S. cerevisiae* strains were created to produce short fatty acids. It was not only possible to show significant increase in their overall production with the highest yield of 118 mg/L (27-fold increase over the wild type) in regular YPD but also the production of specific chain lengths was demonstrated: One strain optimized for hexanoic acid ($C_6$) showed yields of 20 mg/L corresponding to 90% of the detected short FA ($C_6$ to $C_{12}$) in that strain. For specific octanoic acid ($C_8$) production, a share of 89% was shown at an output level of 48 mg/L.

Abstract

In the present invention, the production of short fatty acids was achieved by a structural based rational design, where only key residues in FAS were changed to impose a system of chain length control.

Besides elevated overall levels of short fatty acids (118 mg/L, a 27-fold increase over the wild type) also the specific production of $C_6$ (20 mg/L corresponding to 90% of the detected short FA, $C_6$ to $C_{12}$) and $C_8$ (48 mg/L, 89% of detected short FA) was possible.

Results

For the production of short FA in *S. cerevisiae*, a Δfas1 Δfas2 strain was created. Two heterozygotic strains with one deletion each, were mated and then sporulated to gain the double knockout strain. The two chains of FAS were transformed into cells on two separate low copy vectors (pRS315 and pRS313 respectively) under control of their natural promoters and terminators (Chirala 1992). The plasmid FAS system was then the only source of de-novo fatty acids.

The FAS itself, only produces FA as CoA esters and not as free acids. For *S. cerevisiae* several proteins were reported recently (see e.g. Knight et al., 2014) which putatively hydrolyze the short CoA esters to the free FA. These putative TEs can also contribute to the distinct product distribution due to their own substrate specificity. For the actual quantification, the media was analyzed because short chain free FA produced by *S. cerevisiae* are exported from the cell (Leber & da Silva, 2014).

For the production of short fatty acids, the fatty acids cycle was manipulated in all enzymatic centers that are potentially involved in chain length control (see FIG. 1), the condensation domain (KS) and the transferases (MPT and AT). While the modifying domains (KR, DH and ER) can have different affinities towards intermediates of different lengths, they do not play the key role in determining the product length.

1. Ketoacyl Synthase (KS) Domain:

The KS domain catalyzes the condensation step in the fatty acid synthesis, meaning the actual elongation of intermediates. Mechanistically, the catalyzed reaction works in a ping-pong mechanism: In a first step, the acyl-intermediate is loaded from the ACP into the KS where it binds covalently to C291 (ping step). When the ACP returns to the KS with a bound malonyl, the latter is decarboxylated. The produced carboxylanion reacts with the acyl chain in the KS and thereby cleaves it off from the active center of the KS (pong step).

The mutations introduced into the KS domain (see FIG. 4) for chain length control are influencing the ping step of the reaction by restricting the loading of acyl chains beyond a certain length. As an elongation is less likely (or inhibited), more short FA are produced.

In the first position, a G236S mutation was introduced. This mutation has been linked to enhanced resistance to Cerulenin, a common FAS inhibitor. In *S. cerevisiae* strains with this mutation used for Sake production, an increased level of $C_6$ and its ester derivatives was reported (Aritomi et al., 2004; see also JP 2002/027989 A).

In comparison with the wild type, the G236S strain shows a significant increase of $C_6$ with 15.3 mg/L on average, a 9-fold increase over the wild type (see FIG. 2).

As a second position in the KS, the neighboring M237 was mutated. Comparison of the structural data of the FAS with a bound Cerulenin (Johansson et al., 2008) and the FAS without the latter (Leibundgut et al., 2007), indicated two conformations for M237: a) It was found in a position pointing directly into the KS binding channel and b) pushed aside by Cerulenin which is mimicking a bound acyl substrate. A gatekeeper function of a methionine in this position in the KS binding channel has also previously postulated to explain the bimodal product spectrum found for the Hsmt-KAS (Christensen et al., 2007). Most likely the reported lower binding for $C_8$-ACP (Zhang et al., 2005) can be linked to the rearrangement of the methionine residue as well.

Our intention was to enhance the gatekeeper effect of this crucial position and hinder the elongation of acyl intermediates beyond certain length by replacing it with a bigger, bulkier residue. A M237W mutation was chosen.

The double mutant G236S-M237W was tested and increased levels of $C_6$ (with 19.9 mg/L, 12-fold increase over wild type) and $C_8$ (32.7 mg/L, 56-fold increase over wild type) were found (FIG. 2).

Also, a third promising position in the KS was mutated based on sequence alignments with organisms known to produce $C_6$ at least as an intermediate, such as *Aspergillus parasiticus* and *Aspergillus flavus* (see e.g. Hitchman et al., 2001). The F235Y mutation is located on the opposite side of the G236S-M237W mutation in the binding channel of the KS (see FIG. 4) but is believed to also impede binding of acyl chains beyond $C_6$. Effects of the measured G236S-F237Y double mutant strain could hardly be interpreted since its growth was highly inhibited resulting in very low short FA output. Its results in combination with mutations in the transferases are reported below.

The positions Q193, N258 and D259 are also located at the surface of the KS domain, where they interfere with interaction of the ACP and KS domain. The mutated positions are to lower probability of this interaction. Consequently, an elongation of produced fatty acids is less likely, because intermediates (which are bound to the ACP domain) are not elongated directly and the chances of an early export by the promiscuous MPT domain are increased, leading to shorter fatty acids (FA).

2. Malonyl-/Palmitoyl-Transferase (MPT) Domain:

In the yeast FAS systems, the MPT domain is responsible for malonyl-CoA loading and also for unloading of products (typically $C_{16}$ and $C_{18}$) as CoA esters. Similar to the KS domain, transferases in FAS also work in ping-pong mechanism. A substrate is first loaded from a CoA into the transferase where it binds covalently and is then transferred onto the ACP domain or vice versa. In the MPT specifically, both compound groups, malonyl substrates and acyl products, are transferred via this mechanism and essentially compete in the ping step for one residue, S104, in the active center. The MPT's responsibility in product cleave off made it a target for engineering.

Inherently, the MPT domain is a transferase with a generally broad substrate spectrum, which includes short acyl chains as well. The approach of destabilizing malonyl binding in the MPT and thus, shifting the equilibrium of substrate loading and product unloading in favor of the latter was implemented. It was previously shown in structural studies for other, distant related transferases, that a central arginine stabilizes the carboxyl group of malonyl (see e.g. Bunkoczi et al., 2009). In the present study, a R130K mutation was introduced in the MPT domain, which was believed to have two effects on chain length control: 1) Products could be released more easily since the active site is less often occupied with malonyl. 2) Malonyl as an elongation substrate is loaded less likely into the enzyme, which would have a comparable effect to an overall decrease in malonyl concentration; a condition which has been linked to the production of shorter fatty acids (see e.g. Kawaguchi et al., 1980).

The effects of the R130K mutation in MPT domain on the product spectrum are dramatic (FIG. 2): The overall production of short FA made up from mostly $C_8$ was 100 mg/L, a 23-fold increase over the wild type.

3. Acetyl Transferase (AT) Domain:

In the *S. cerevisiae* FAS, the loading of acetyl onto the enzyme is catalyzed by a second transferase, the acetyl transferase (AT). Despite the differences in substrate specificity, all acyl transferases show high homologies. Since the mentioned studies (see e.g. Bunkoczi et al., 2009) also lead to an increased acetyl binding, similar engineering on the AT domain was considered, potentially leading to an increased acetyl/malonyl ratio on the enzyme, which is beneficial for the production of short FA.

In the present study, an I306A mutation was introduced. As a second desirable effect, an acquired ability to transfer short acyl chains could open up a new way for product release.

4. Combinations of Mutations:

The mutations in different domains were also combined in several variations (FIG. 2), not only leading to increased overall amounts, but also several yeast strains with high chain length specificity. See Table 1.

Table 1 also gives an indication which chain length is favored with the introduction of a particular mutation. For some mutations, it can be clearly seen, that if an increased short FA output was found, this was mainly due to a higher yield in $C_6$ as found when the G236S or the I306A mutation is added to an existing combination. The introduction of the M237W or the R130K mutation, however, rather leads to an increase in $C_8$, if an increase in short FA was detected at all.

A few combinations and their effects are listed here:

The highest total yield was achieved with the combination of I306A-R130K-G236S (AT MPT KS mutant), producing a total amount of 118 mg/L.

For the specific production of $C_6$, the double mutant I306A-G236S (AT KS mutant) showed best results with 20 mg/L of $C_6$ accounting for 90% of the measured short FA ($C_6$ to $C_{12}$).

A similar specificity, but for the production for $C_8$, was possible with the triple mutant I306A-R130K-F265Y (AT MPT KS mutant) with a yield of 48 mg/L for $C_8$ specifically representing 89% of its short FA output.

With the I306A-R130K-G236S-N258A construct but a slightly different vector (promoter exchanged ADH2 promotor and buffered medium, 100 mM K2HPO4/KH2PO4), the total yield was also very high with 344 mg/L.

Discussion

In our study, we focused on one aspect of reaction control of fatty acid production, the chain length regulation, and its rational manipulation in the enzyme responsible for its production, the fatty acid synthase. Only key residues were to be modified providing a minimally invasive system for the in vivo production of short fatty acids in *S. cerevisiae*. The FAS was brought into a fas1 fas2 knockout strain via a vector, but under its natural promoter and only on a low copy plasmid, mimicking natural conditions. Hence, the system was not optimized for best overall FA production but instead was rather to ensure highest possible control, also providing the ability to directly map the relations between mutations and yield in short FA.

In order to alter the product spectrum, the FAS was modified in all active centers potentially regulating chain length:

1) In the KS domain located on FAS 2, six residues were altered in order to limit elongation of intermediate products (G236S, M237W, F265Y, Q193A/E, N258A/D, D259A).

2) In the MPT domain located on FAS 1, loading of malonyl used for elongation was artificially limited and product release accordingly facilitated (R130K).

3) In the AT domain located on FAS 1, binding channels were broadened to increase acetyl influx or more likely, providing a new way for short chain product release (I306A).

The engineering presented here can be understood as metabolic engineering. Fluxes were changed rather than only the ability of one individually domain to process a certain reaction. On the FAS itself, twelve reaction steps can be catalyzed (when transferase steps are included) and this is not considering that eight of them are iteratively repeated several times until a certain chain length is reached. In this complex network of reactions which are essentially influencing each other, we were able to alter affinities and consequently change the kinetics and reaction rates with the introduction of concise mutations.

An expansive influence on the FA chain length could be shown. The effects were measured with the result of different overall amounts of short FA and a highest overall yield of 118 mg/L. The increase is 27-fold higher than in the wild type, that clearly only produces short FA as a minor byproduct in the range of 4.3 mg/L. Also distinct and controllable selectivity of chain lengths was demonstrated. For specific production of $C_6$, the I306A-G236S mutant was favorable (20 mg/L, 90% share $C_6$), for $C_8$, the I306A-R130K-F265Y mutant respectively (48 mg/L, 89% share of $C_8$).

The immediate products of the FAS, the acyl CoA esters, were not quantified but instead the extracellular free FA. This implies proteins with thioesterase activity hydrolyzing acyl CoA esters intracellularly (Knight et al., 2014). These proteins and fatty acid transporters potentially contribute to distinct product spectra.

The scope of the study was to modulate chain length in a non-invasive approach. This means that the fas1 fas2 knockout strain was complemented with fas1 and fas2 variants set under their native promoters and terminators.

In our experiments, the viability of the cells was influenced by the specific mutations in the FAS. The data suggest that some of the mutations significantly influenced the fatty acid spectrum, i.e. decreasing intracellular $C_{16}/C_{18}$ fatty acid (CoA esters) levels, so that growth was affected. Such an impact on the viability of cells by some of our mutations is supported by supplementation studies with $C_{18:1}$, that generally restored normal growth behavior (Table 2). This implies that the system is highly complex and short chain fatty acid production has to be adapted to host cell architecture.

TABLE 1

Increase/Decrease of yield after introduction of mutations.
To quantify how beneficial a mutation is, the strain without the mutation (first line) is compared to the same strain with the mutation (second line). By dividing the second value by the first value, the increase a mutation adds to the yield (for $C_6$, $C_8$ and total short FA) is given as a factor ("x-fold increase"). Accordingly, values above 1 (in bold) are equivalent to a positive, higher yield; for values below 1, the yield dropped with the introduction of the mutation.

| Mutation | | $C_6$ (mg/L) | $C_8$ (mg/L) | total ($C_6$ to $C_{12}$) (mg/L) |
|---|---|---|---|---|
| G236S (KS domain) | wild type | 1.7 | 0.6 | 4.3 |
| | G236S | 15.3 | 3.9 | 21.6 |
| | X-fold increase | 9.1 | 6.7 | 5.0 |
| | R130K | 15.7 | 80.2 | 100.1 |
| | R130K G236S | 9.4 | 26.7 | 39.5 |
| | X-fold increase | 0.6 | 0.3 | 0.4 |
| M237W (KS domain) | G236S | 15.3 | 3.9 | 21.6 |
| | G236S M237W | 19.9 | 32.7 | 57.2 |
| | X-fold increase | 1.3 | 8.3 | 2.6 |
| | I306A G236S | 20.4 | 1.0 | 22.8 |
| | G236S M237W I306A | 37.1 | 25.6 | 65.9 |
| | X-fold increase | 1.8 | 25.2 | 2.9 |
| | I306A R130K G236S | 52.1 | 63.1 | 118.2 |
| | G236S M237W R130K I306A | 13.0 | 77.1 | 104.1 |
| | X-fold increase | 0.2 | 1.2 | 0.9 |
| F265Y (KS domain) | I306A R130K | 10.1 | 25.1 | 37.4 |
| | I306A R130K F265Y | 2.2 | 47.9 | 53.9 |
| | X-fold increase | 0.2 | 1.9 | 1.4 |
| I306A (AT domain) | G236S | 15.3 | 3.9 | 21.6 |
| | G236S I306A | 20.4 | 1.0 | 22.8 |
| | X-fold increase | 1.3 | 0.3 | 1.1 |
| | G236S M237W | 19.9 | 32.7 | 57.2 |
| | G236S M237W I306A | 37.1 | 25.6 | 65.9 |
| | X-fold increase | 1.9 | 0.8 | 1.2 |
| | R130K | 15.7 | 80.2 | 100.1 |
| | R130K I306A | 10.1 | 25.1 | 37.4 |
| | X-fold increase | 0.6 | 0.3 | 0.4 |
| R130K (MPT domain) | wild type | 1.7 | 0.6 | 4.3 |
| | R130K | 15.7 | 80.2 | 100.1 |
| | X-fold increase | 9.4 | 137.3 | 23.4 |
| | G236S | 15.3 | 3.9 | 21.6 |
| | G236S R130K | 9.4 | 26.7 | 39.5 |
| | X-fold increase | 0.6 | 6.8 | 1.8 |
| | I306A G236S | 20.4 | 1.0 | 22.8 |
| | I306A G236S R130K | 52.1 | 63.1 | 118.2 |
| | X-fold increase | 2.6 | 62.2 | 5.2 |
| | G236S M237W I306A | 37.1 | 25.6 | 65.9 |
| | G236S M237W I306A R130K | 13.0 | 77.1 | 104.1 |
| | X-fold increase | 0.4 | 3.0 | 1.6 |

The following examples and drawings illustrate the present invention without, however, limiting the same thereto.

The FAS carries modifications in the KS, AT and MPT domain to produce shorter fatty acids (instead of its native product, typically $C_{16}$- or $C_{18}$-CoA) from acetyl-CoA, malonyl-CoA and NADPH. The KS mutations (G236S, M237W and F265Y) were constructed to restrict the loading of substrates beyond a certain length (indicated with a dotted line leading to the KS domain) and thus leading to the formation of shorter products. The AT (with the I306A mutation) was to enhance the loading of acetyl-CoA (indicated with the bold arrow at the AT domain) and/or act as a transferase to cleave off short chain products (dashed arrow from acyl products through the AT domain), a reaction not found in wild type FAS. The MPT mutation R130K was introduced to shift the balance in binding of malonyl and acyl chains in favor of the latter. Both the lowered malonyl loading (indicated by an arrow with a smaller tip at the MPT domain) as well as the easier acyl chain release add to an increase of short fatty acids. S. cerevisiae FAS naturally produces CoA esters, which are hydrolyzed by thioesterases, if they are shorter than a certain length. The free FA are then transported out of the cell into the media, from which they are extracted for their analysis.

Figure 1:
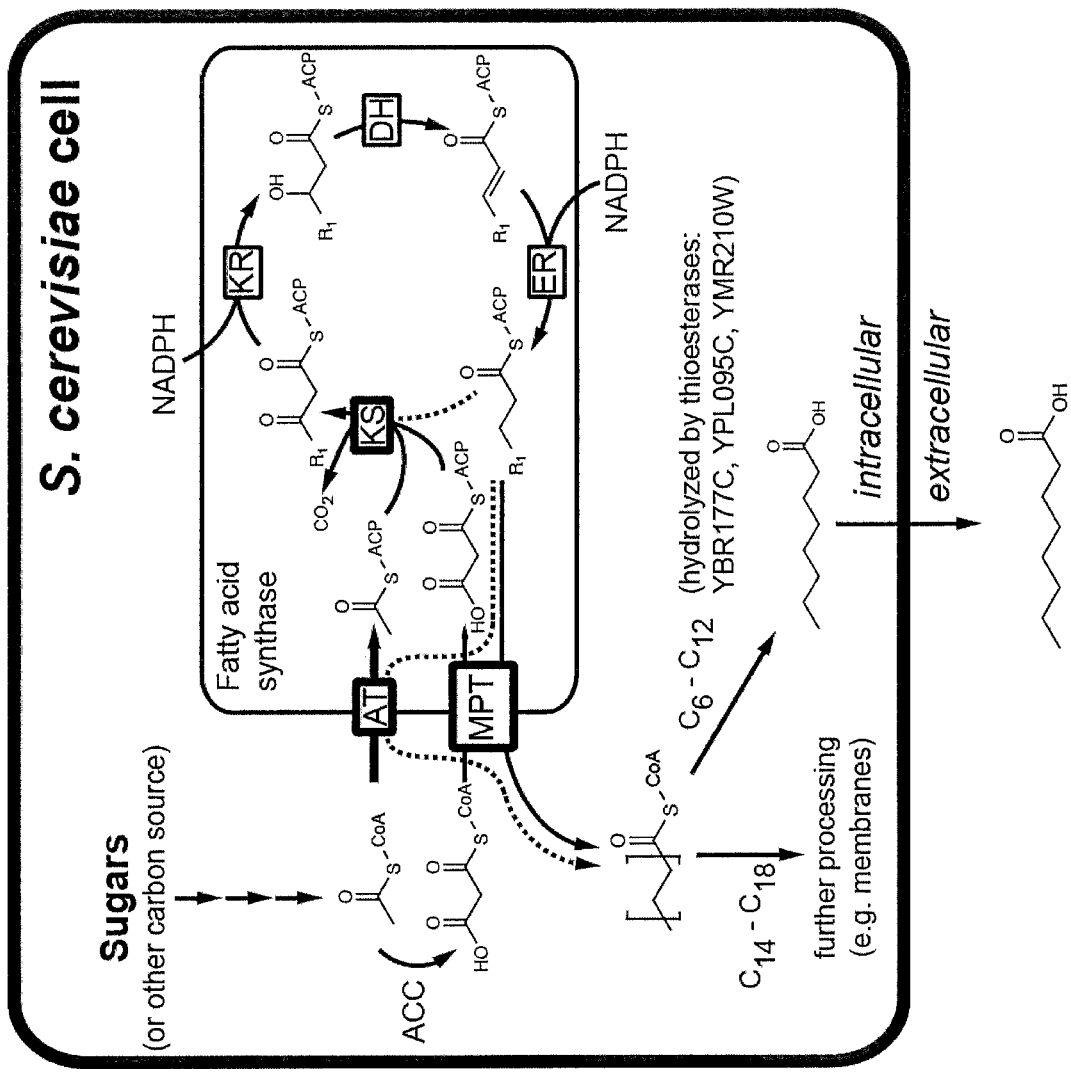
FIG. 1. Fatty acid cycle and its manipulation.
Figure 2:
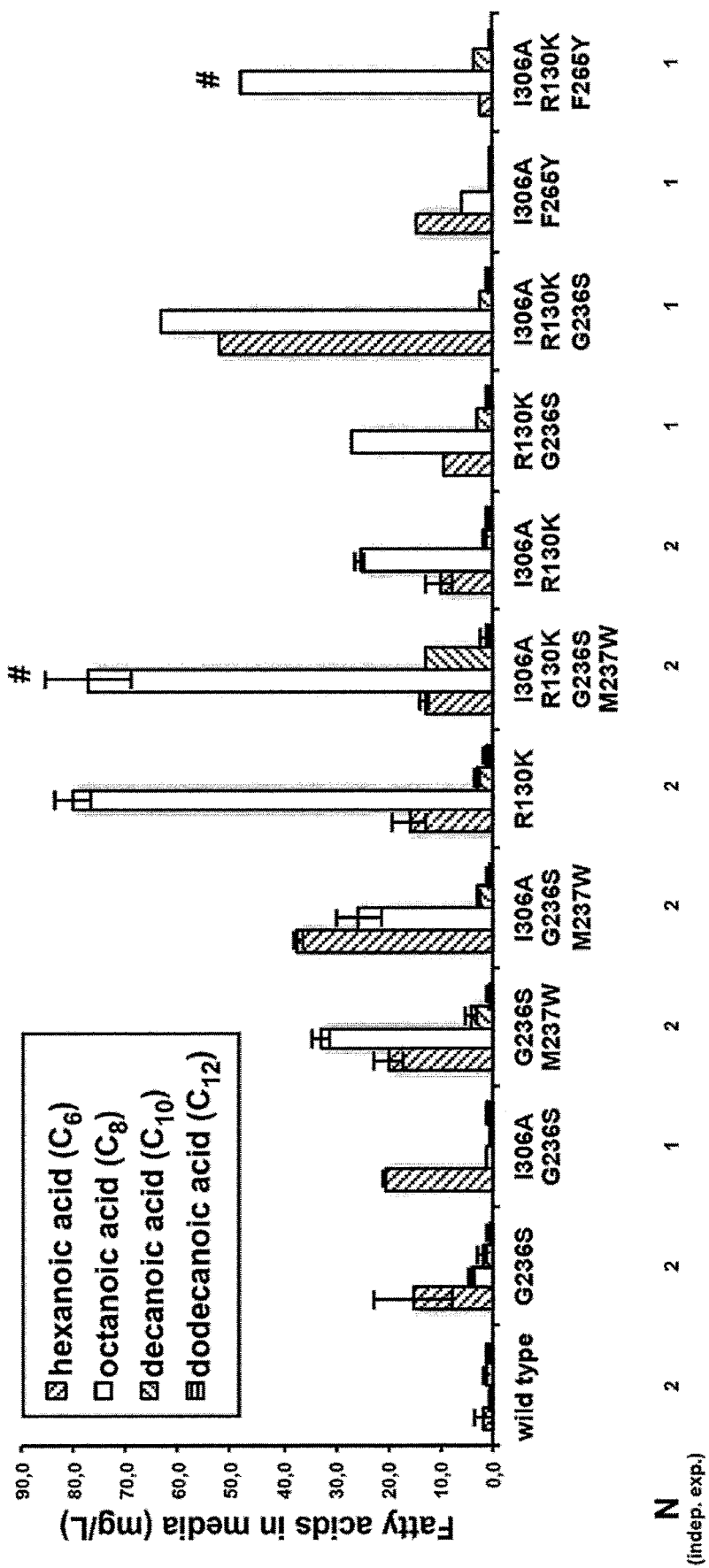

FIG. 2. Product spectra of selected mutated strains in YPD.

For the measurements of the product spectra, cultures of S. cerevisiae were grown for 48 h at 30° C., the media extracted and later quantified via GC-FID. Error bars shown here reflect the standard deviation from two independent experiments (beginning from separate transformations into S. cerevisiae). The strain carrying the I306A-R130K-G236S-M11251W mutations and the strain with the I306A-R130K-F265Y mutations (both marked #) only grew to approximately one third of the regular cell density of the rest.

Figure 3:
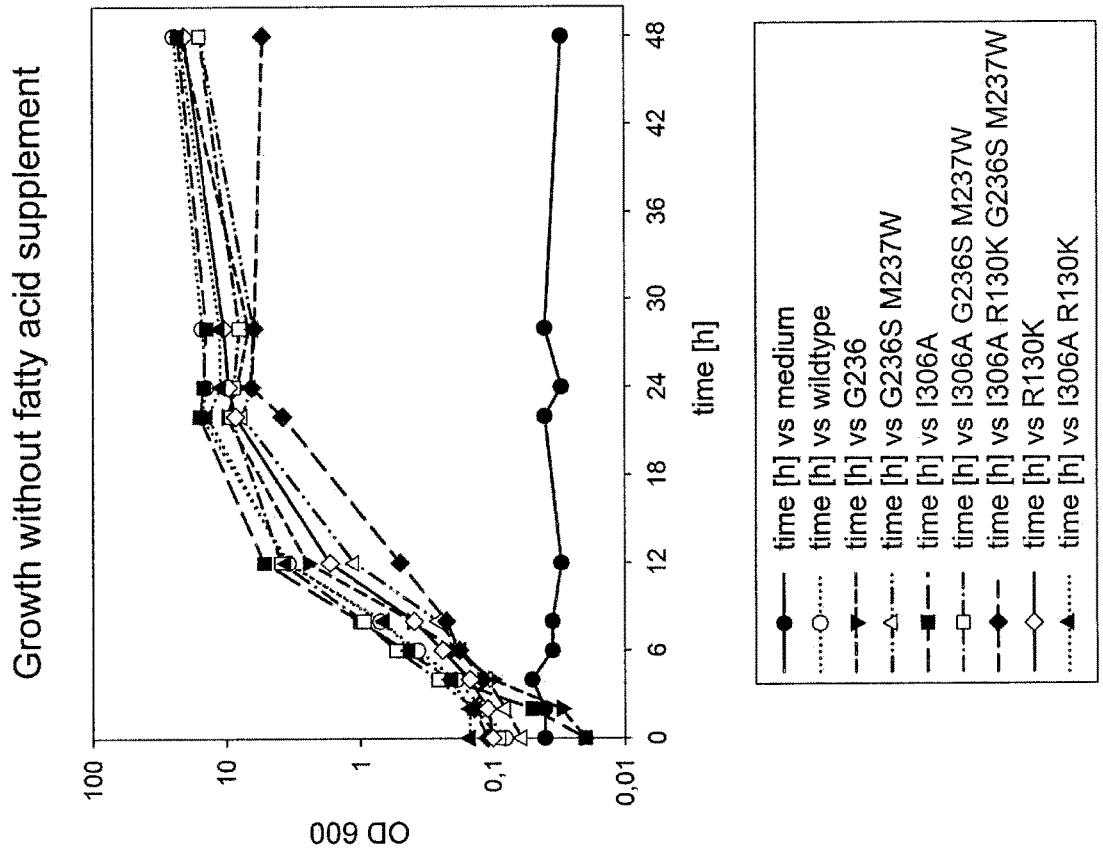

FIG. 3. Growing curve of manipulated Yeast strains.

For selected strains, the cell density was monitored at several time points.

Figure 4:
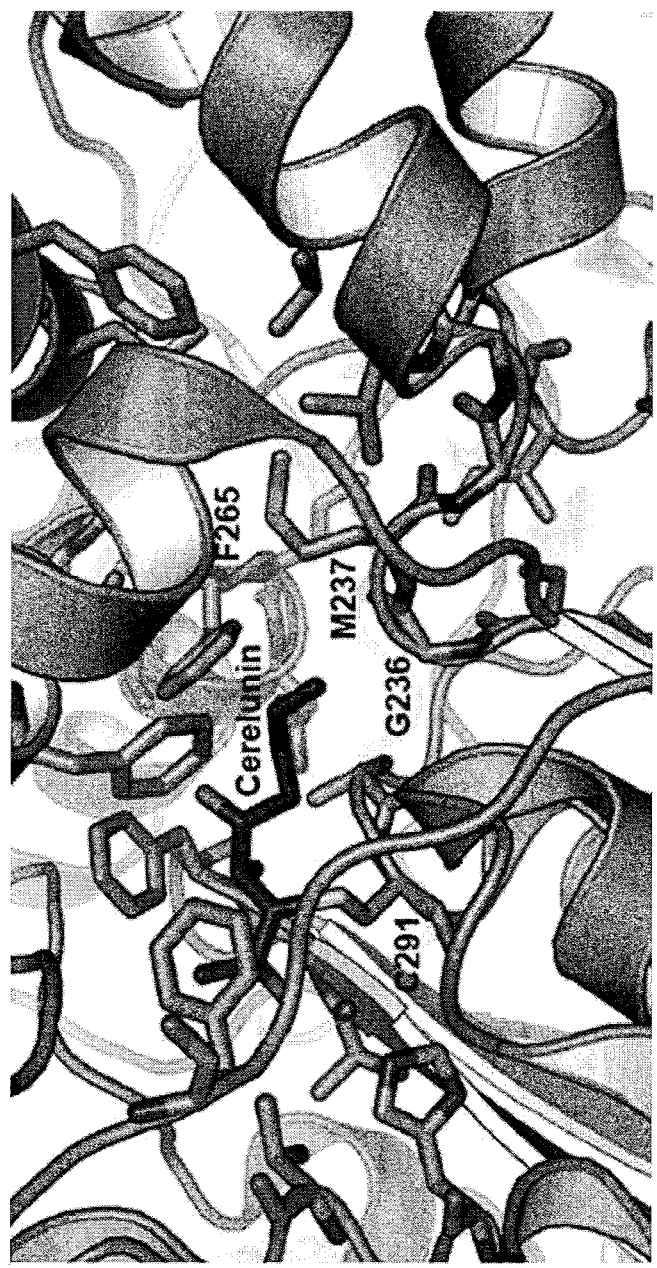

FIG. 4. Binding channel of the KS domain with mutation sites.

Here, the KS domain from the S. cerevisiae FAS (light grey) is shown in cartoon depiction with important residues shown in stick representation (based on PDB code 2VKZ). The active center C291 is located on the left with a bound Cerulenin molecule (dark grey), a known FAS inhibitor mimicking a bound acyl. The binding channel extends to the right, where three mutation sites, G236S, M1250W and F265Y are shown with their initial amino acids.

Figure 5:
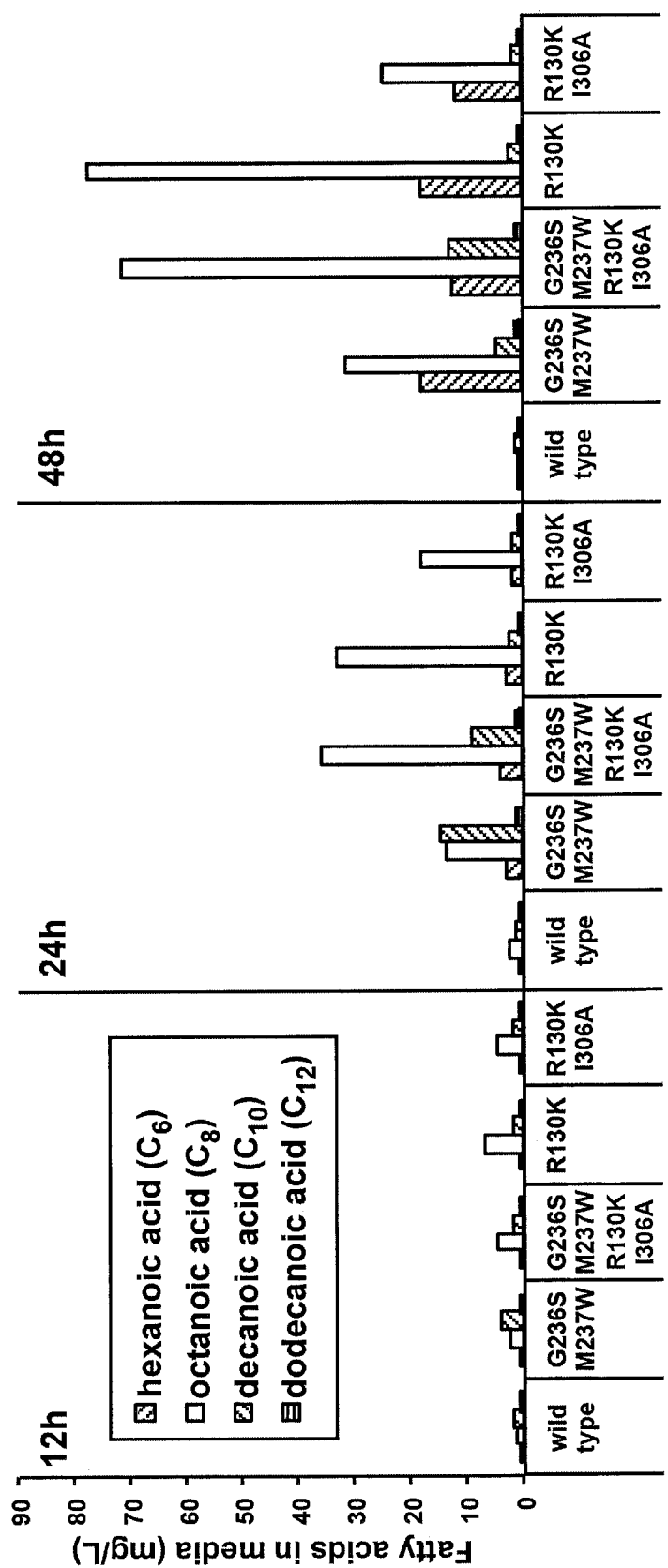

FIG. 5. Product Spectra at additional time points of selected strains.

Besides the regular product spectra after 48 h, additional measurements were performed for selected strains after 12 h and 24 h.

Figure 6:
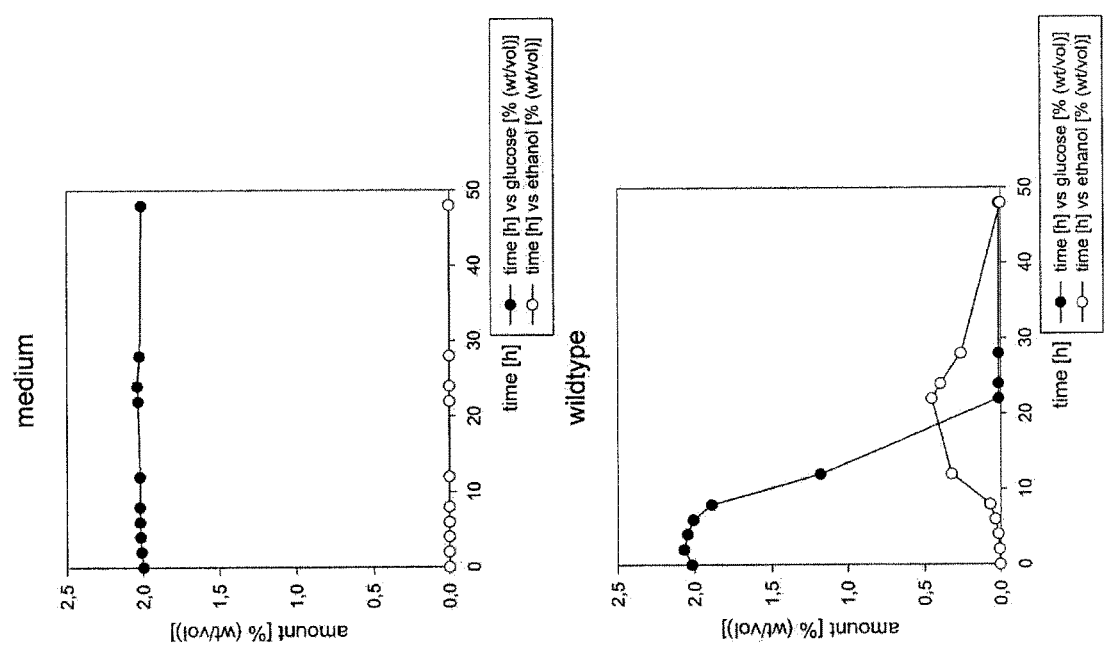
Figure 6:
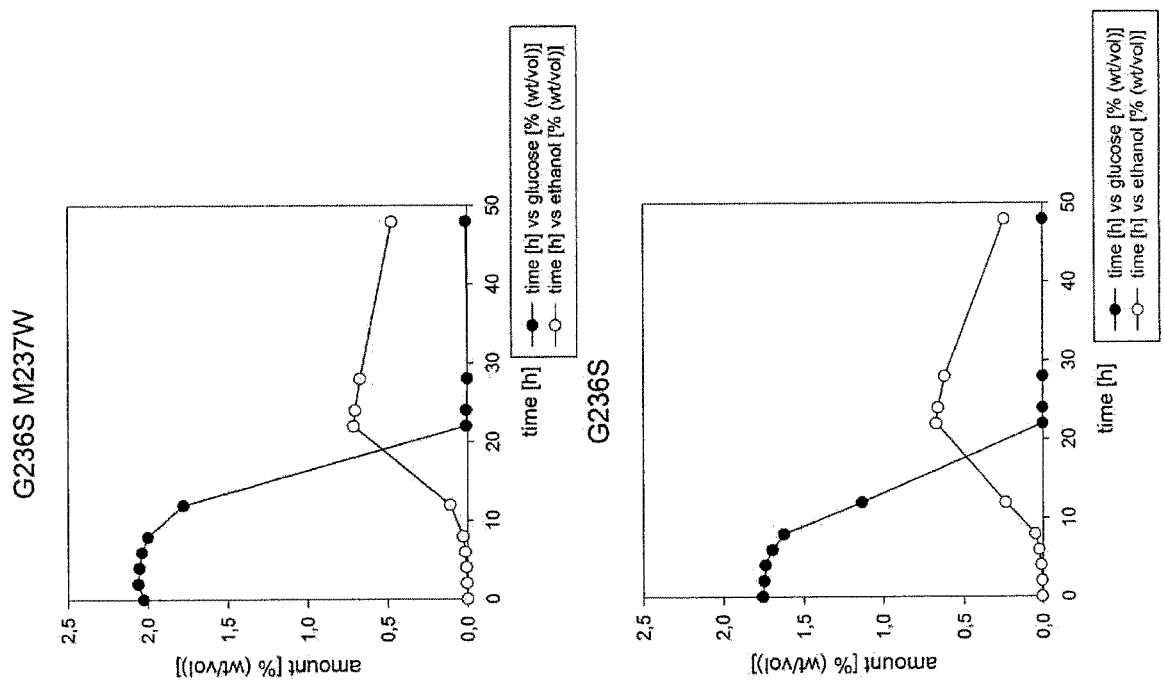
Figure 6:
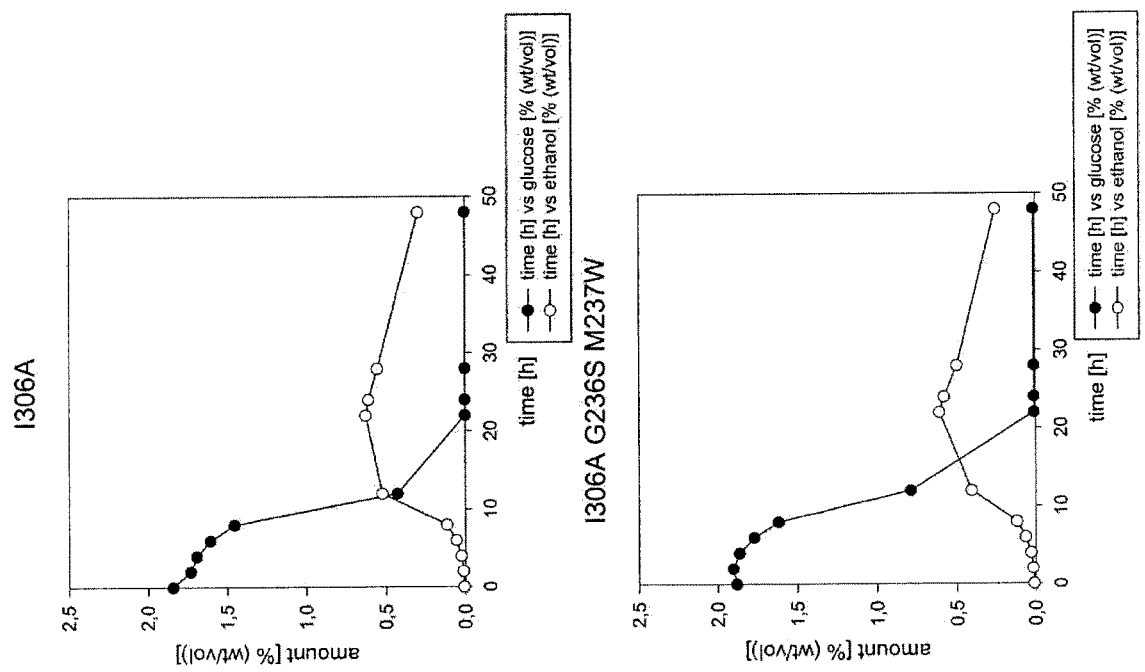
Figure 6:
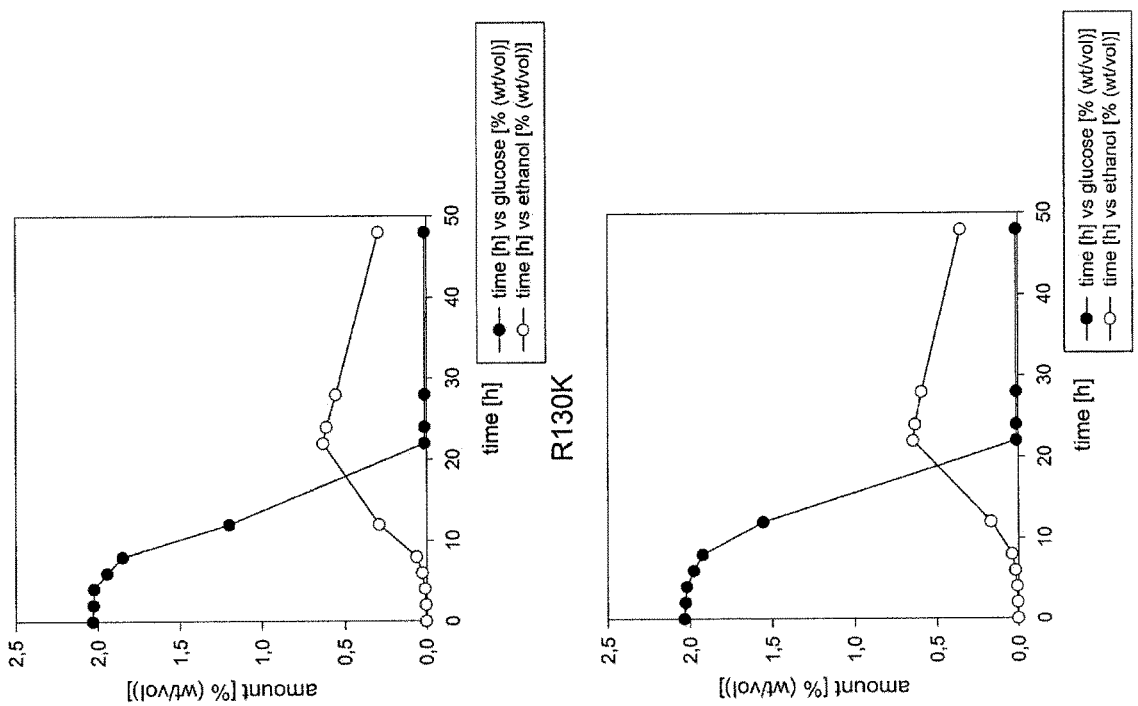
Figure 6:
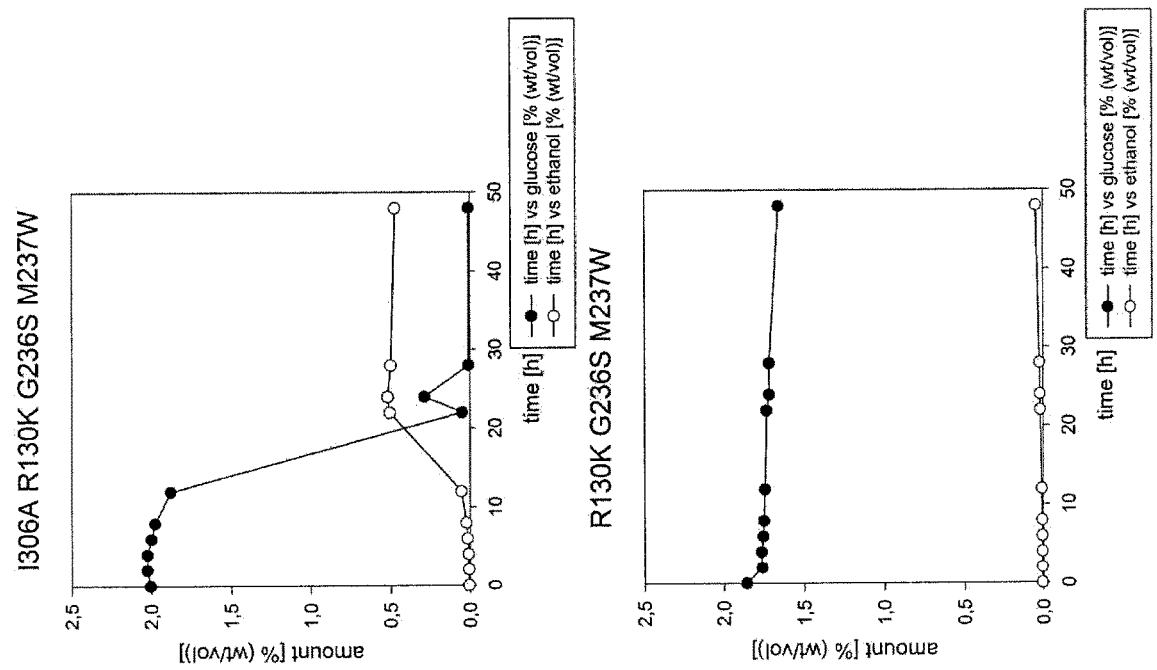

FIG. 6. Glucose and Ethanol concentration over time.

For selected strains, the medium was monitored at several time points during the 48 h cultivation. The amount of remaining glucose and produced ethanol in the fermentation medium was measured with HPLC.

Figure 7:
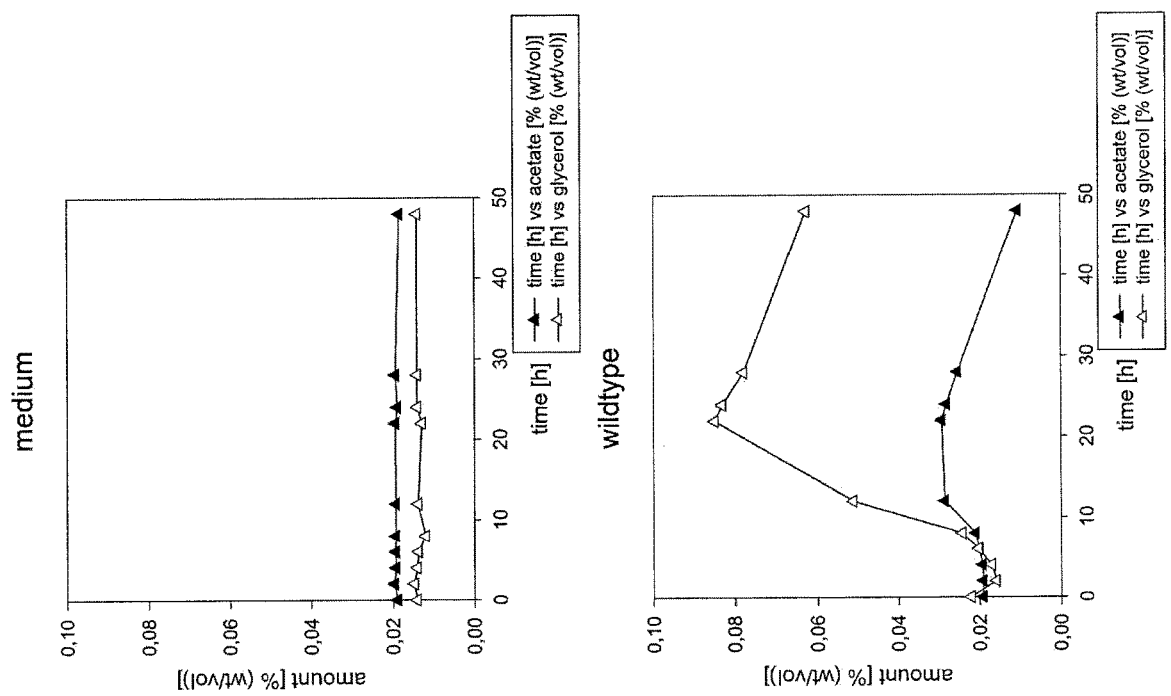
Figure 7:
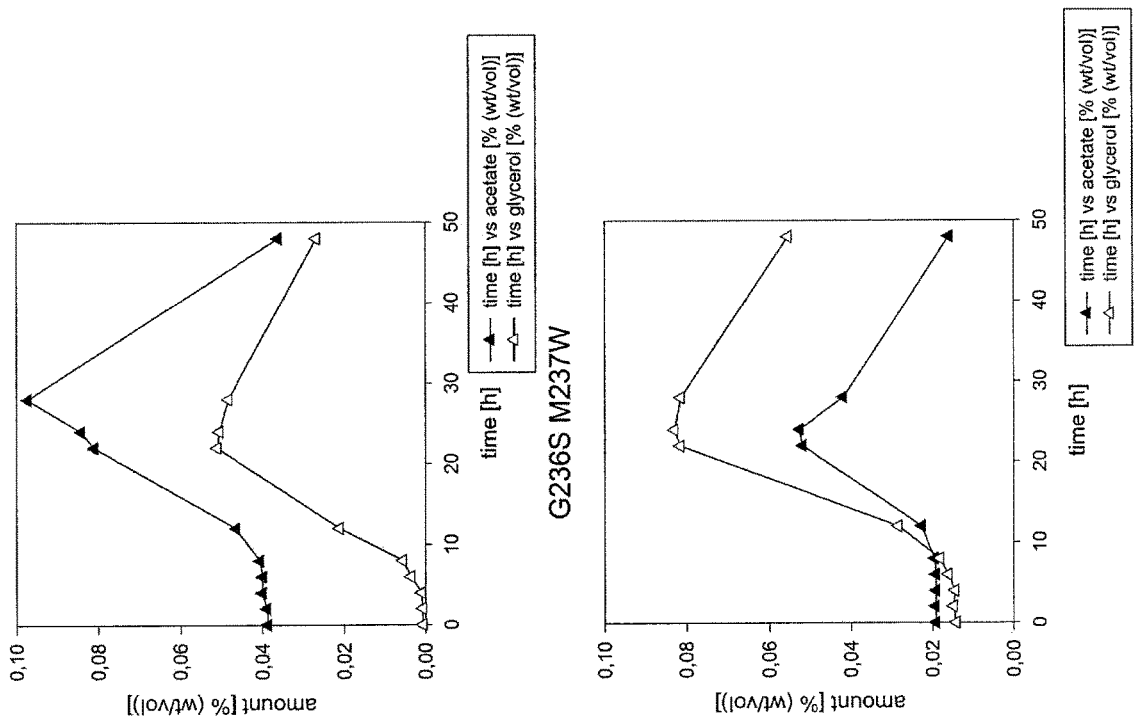
Figure 7:
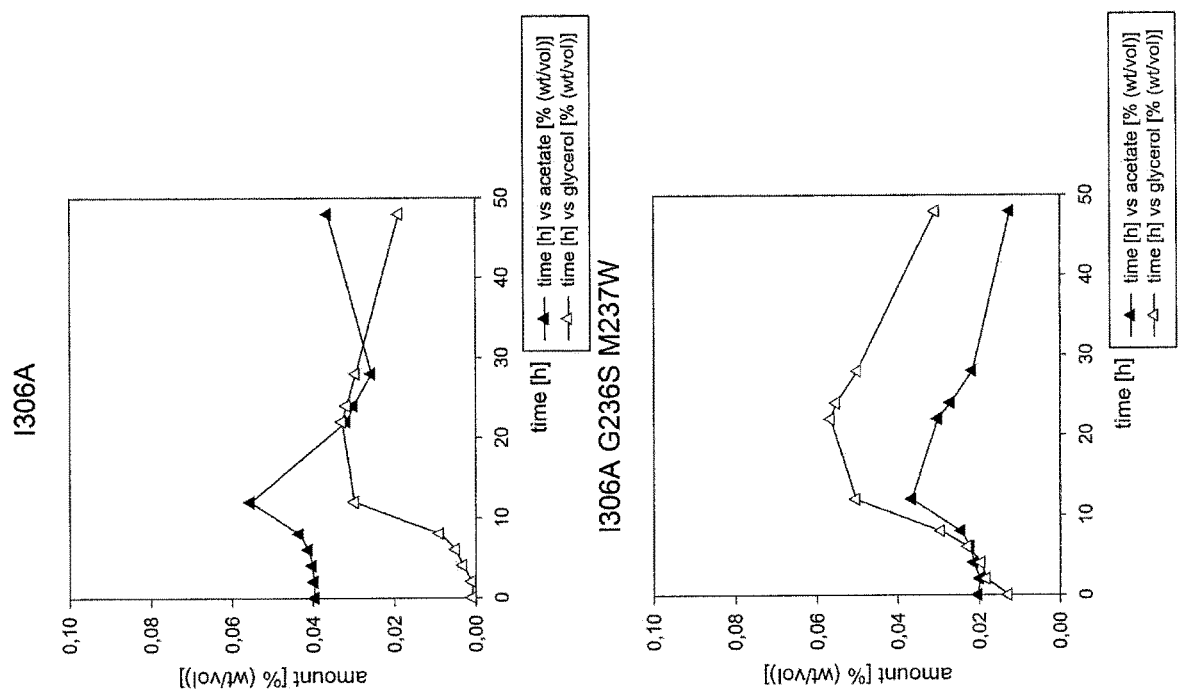
Figure 7:
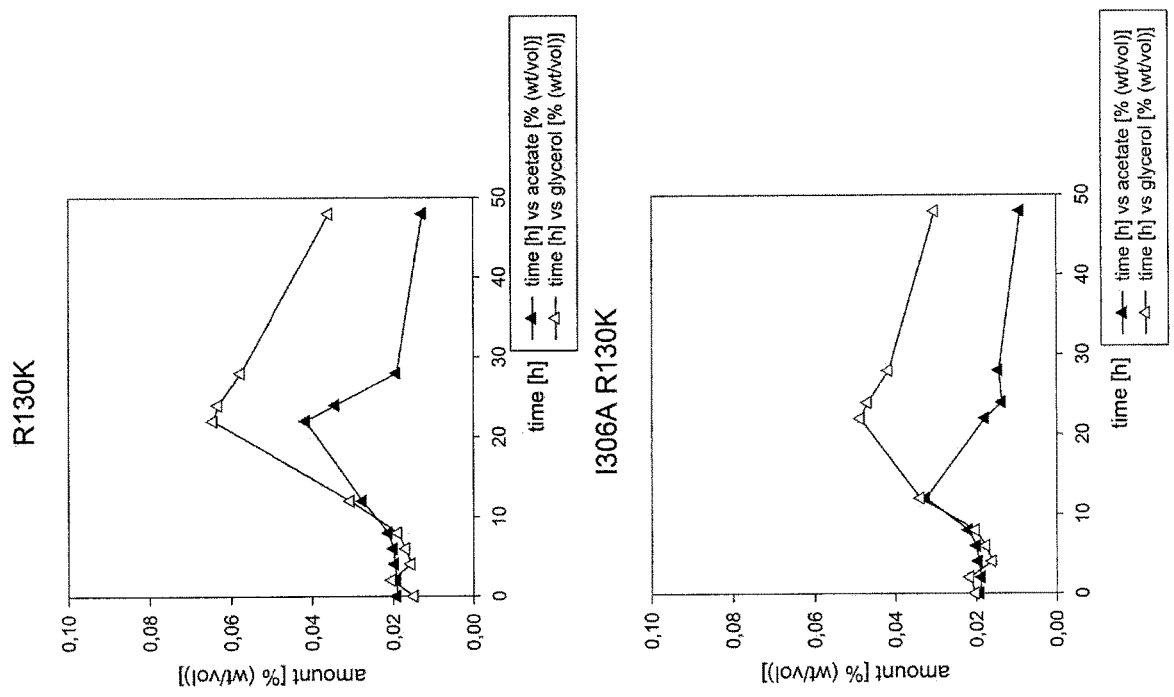
Figure 7:
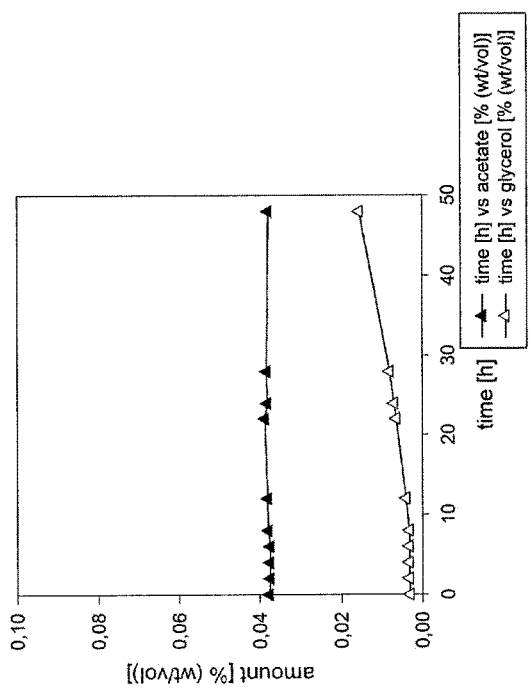
Figure 7:
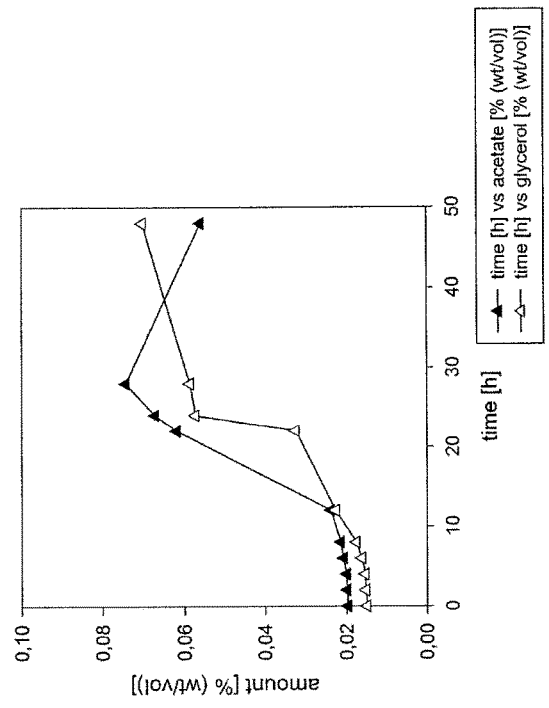

FIG. 7. Acetate and Glycerol concentration over time.

For the same selected strains as in FIG. 6, also the acetate and glycerol concentrations in the medium were analyzed by HPLC.

Figure 8:
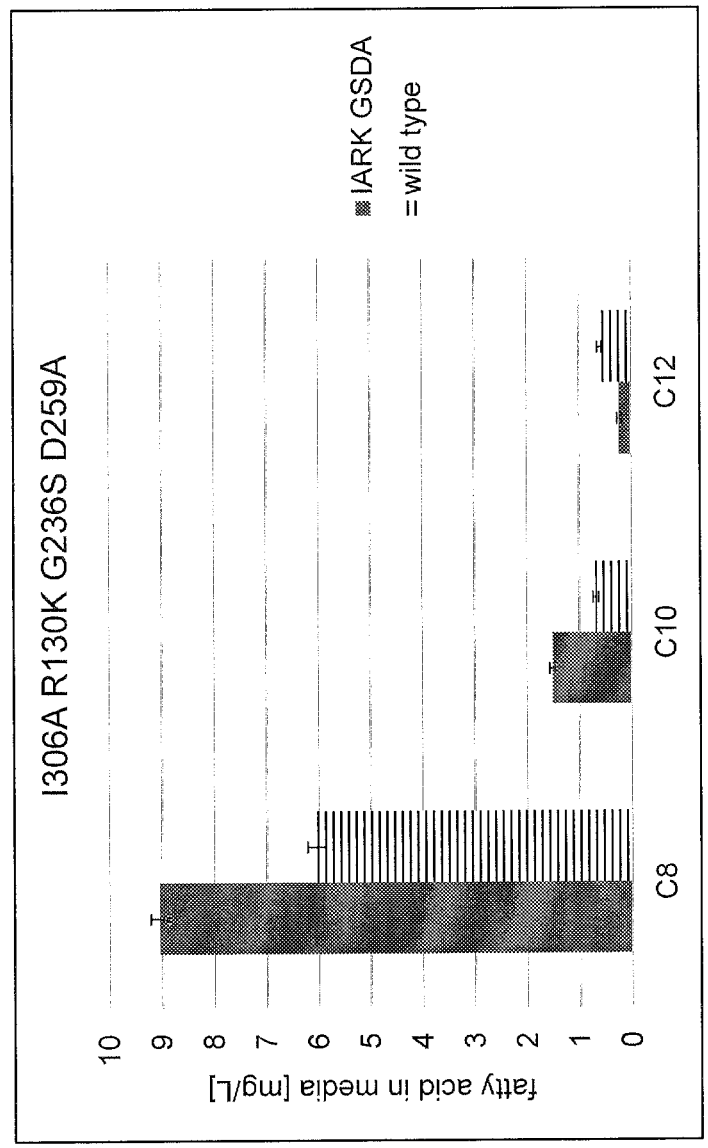

FIG. 8. Product spectrum of a further mutated strain in YPD.

The product spectrum of a strain carrying the I306A-R130K-G236S-D259A mutations is shown in comparison to the wild type. In this case, the medium was buffered to pH 6.5 (100 mM $K_2HPO_4/KH_2PO_4$) and the promotor was exchanged for both the wild type and the construct to ADH2.

For the measurements of the product spectrum, cultures of S. cerevisiae were grown at 30° C., cell growth was hindered and after 72 h cell density was only 5.0 ($OD_{600}$), the media extracted and later quantified via GC-FID. Error bars shown here reflect the standard deviation from three independent results (beginning from separate clones of S. cerevisiae).

Figure 9:
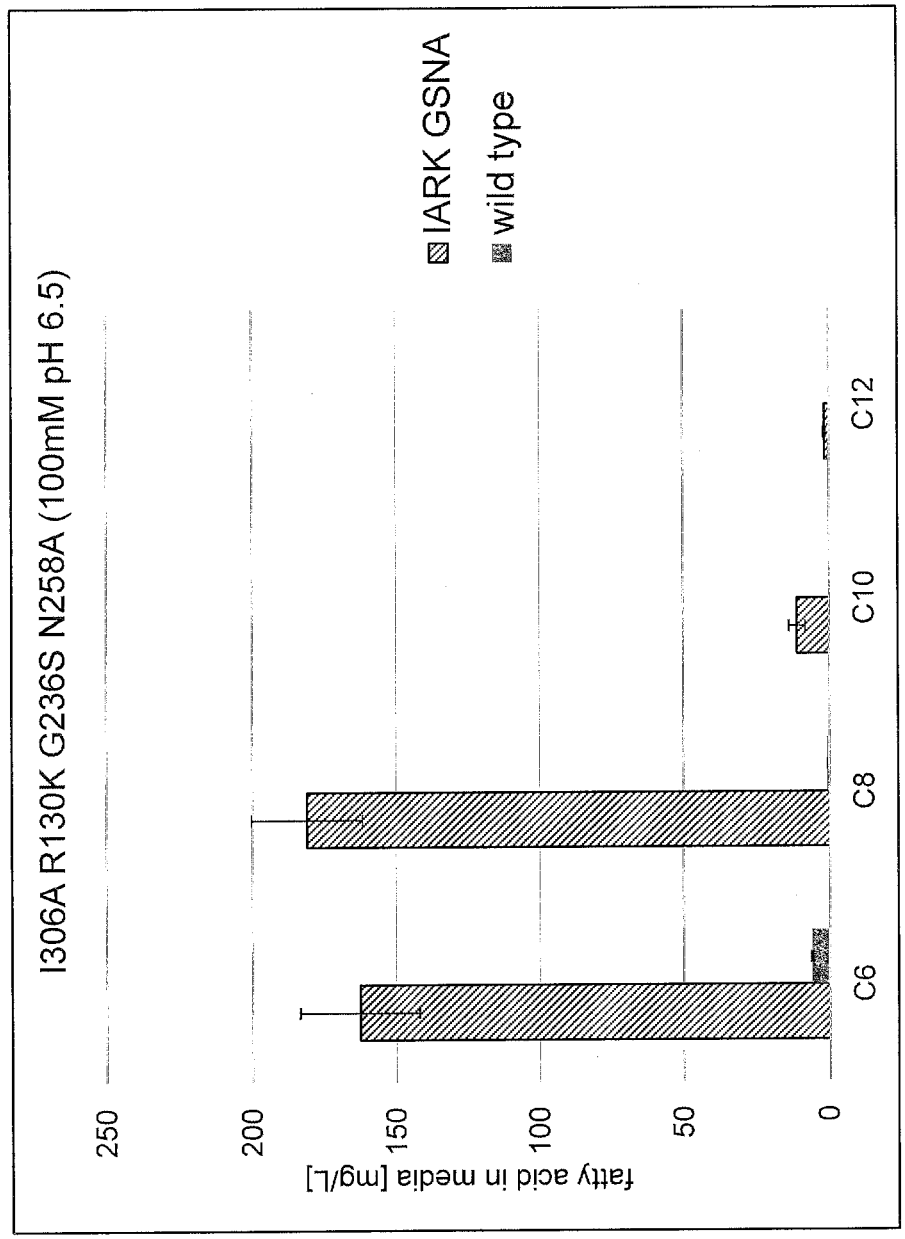

FIG. 9. Product spectrum of a further mutated strain in YPD.

The product spectrum of a strain carrying the I306A-R130K-G236S-N258A mutations is shown in comparison to the wild type. In this case, the medium was buffered to pH 6.5 (100 mM K$_2$HPO$_4$/KH$_2$PO$_4$) and the promotor was exchanged for both the wild type and the construct to ADH2).

For the measurements of the product spectrum, cultures of *S. cerevisiae* were grown at 30° C., cell growth was hindered and after 72 h cell density was only 5.0 (OD$_{600}$), the media extracted and later quantified via GC-FID. Error bars shown here reflect the standard deviation from three independent results (beginning from separate clones of *S. cerevisiae*).

EXAMPLES

Example 1

1. Materials and Methods
1.1 Description Yeast Strain

The haploid *S. cerevisiae* strain BY.PK1238_1A_KO, used in this work, has a BY background and the reading frames of FAS1 and FAS2 are each replaced by a kanMX4 cassette, resulting in a clean knock out of FAS I and antibiotic resistance against Geneticin. The exact genotype is Mata; ura3.Δ0; his3Δ0; leu2Δ0; TRP1; lys2Δ0; MET15; fas1::uptag-kanMX4-downtag; fas2::uptag-kanMX4-downtag.

1.2 Vector Description

The vectors used in this work are centromeric pRS shuttle vectors of types pRS313 and pRS315 (Sikorski & Hieter, 1989) with single copy number and HISS and LEU2 auxotrophy marker, respectively. FAS1 or mutations thereof were always provided on pRS315, while FAS2 or mutations thereof were always provided on pRS313, each regulated by its according native promoter (995 bp upstream for FAS1 and 480 bp upstream for FAS2) (Chirala 1992). Terminator sequences were set to 295 bp and 258 bp, respectively, downstream of the open reading frames. Cloning was always done in *E. coli* using the Infusion HD cloning kit (Clontech, Mountain View, USA).

Wild type FAS1 and FAS2 genes were assembled from several fragments, which were amplified from *S. cerevisiae* genomic DNA, into pRS vectors using BamHI and SalI restriction sites. Exact chromosomal coordinates including promoter and terminator sequences according to strain S288C are for FAS1 (YKL182w): Chr XI 99676-107121 and for FAS2 (YPL231w): ChrXVI 108172-114573.

1.3 Primers

For the introduction of mutations by site-directed mutagenesis, the primers are listed below. The mutation site is indicated in bold typing, while the overlap between the primers is underlined.

```
For FAS 1 variants:
I306A forward
                                    SEQ ID NO. 7
5'-TTCTTCGCTGGTGTTCGTTGTTACGAAGCATACCCAAACACTTCC-3'

I306A reverse
                                    SEQ ID NO. 8
5'-
ACACCAGCG AAG AATAATACAGTAATTGCTTTTCTTACGGAGACG-3'

R130K forward
                                    SEQ ID NO. 9
5'-AGTTGTGTTCTACAAAGGTATGACTATGCAAGTTGCTGTTCC-3'

R130K reverse
                                    SEQ ID NO. 10
5'-CATAGTCATACCTTTGTAGAACACAACTTCAACTAAAGATTCGATA
GAC-3'

For FAS 2 variants:
G236S forward
                                    SEQ ID NO. 11
5'-TCTGGTTCTTCTATGGGTGGTGTTTCTGCCTTACG-3'

G236S reverse
                                    SEQ ID NO. 12
5'-CATAGAAGAACCAGAACAGTTACCAACCTCAGAAACATGTACG-3'

M237W forward
                                    SEQ ID NO. 13
5'-TCTGGTTCTTCTTGGGGTGGTGTTTCTGCCTTACG-3'

M237W reverse
                                    SEQ ID NO. 14
5'-CCAAGAAGAACCAGAACAGTTACCAACCTCAGAAACATGTACG-3'

F265Y forward
                                    SEQ ID NO. 15
5'-ATTTTACAAGAATCA TAT ATCAACACCATGTCCGC-3'

F265Y reverse
                                    SEQ ID NO. 16
5'-TGATTCTTGTAAAATATCATTTTGGACAGGC-3'
```

1.4 Transformation

For yeast transformation, approximately 1 µg of each plasmid DNA was co-transformed following a modified lithium acetate protocol (Schiestl & Gietz, 1989). A 5 mL overnight culture of strain BY.PK1238_1A_KO in YPD (1% yeast extract, 2% peptone, both produced by BD, Difco Laboratories, Sparks, USA; 2% dextrose, purchased from Roth, Karlsruhe, Germany) containing 200 µg/mL Geneticin disulfate, free fatty acids (myristic, palmitic and stearic acid, each 50 µg/mL) and 1% Tween20 grown at 30° C. and 200 rpm was used to inoculate a main culture in the same medium. After shaking at 30° C. and 200 rpm to OD$_{600}$=0.8, a volume of 5 mL of this culture was harvested by centrifugation (3000 rcf, 5 min, 24° C.). The cells were washed by resuspending in 1 mL water and centrifuged again. After resuspension in lithium acetate solution (0.1 M), cells were incubated for 5 min at 24° C. and centrifuged (5000 rcf, 15 s, 24° C.), before the transformation mix was added (240 µL PEG 1,500 solution (50%), 76 µL water, 36 µL lithium acetate solution (1.0 M), 5.0 µL single stranded DNA solution from salmon testis (10 mg/mL), 2 µL of each plasmid DNA solution). The cell suspension was mixed well and incubated for 30 min at 30° C. followed by 20 min at 42° C. After pelleting the cells by centrifugation (4000 rcf, 15 s, 4° C.), they were washed with 1 mL water, pelleted again (4000 rcf, 15 s, 4° C.) and resuspended in 100 µL water. For selection of the yeast transformants, the cell suspension was spread on SCD-ura; -leu agar plates containing 200 µg/mL Geneticin disulfate, free fatty acids (myristic, palmitic and stearic acid, each 50 µg/mL) and 1% Tween20.

1.5 Cultures for Product Analysis

For the product analysis, several colonies of the *S. cerevisiae* strains were picked and united in one pre-culture (5 ml YPD with 200 µg/mL Geneticin disulfate, 50 mg/ml final concentration). After shaking at 200 rpm at 30° C. overnight, the OD$_{600}$ was measured. The main culture (50 ml YPD with 200 µg/mL Geneticin disulfate, 50 mg/ml final concentration) was inoculated to OD$_{600}$=0.1 and shaken for 48 h at 200 rpm and 30° C. Before further processing, the OD$_{600}$ was measured again.

For samples with long FA supplementation, C$_{18:1}$ and Tergitol NP-40 (solution in water, 70%) were added to all cultures to a final concentration of 1 mM or 1% in the case of Tergitol.

1.6 Sample Processing

For FA extraction, a protocol similar to a previously published one (Leber & da Silva, 2014) was used: First cells were spun down at 3,500 rcf for 15 min. The supernatant was aliquoted in 10 ml portions and 0.2 mg of the internal standard, heptanoic acid ($C_7$), was added. After acidification with 1 ml HCl (1 M), 2.5 ml of a mixture of equal amounts of methanol and chloroform were added. The samples were shaken vigorously for 5 min and then centrifuged again at 3 500 rcf for 10 min. The chloroform layer was transferred to a new vial and any residual water removed. The liquid was then fully evaporated in a SpeedVac. For methylation a previously published protocol was used (Ichihara & Fukubayashi, 2010).

1.7 Determination of Free Fatty Acid by Gas Chromatography (GC)

The resulting fatty acid methyl esters dissolved in hexane (Ichihara & Fukubayashi, 2010), were measured with a Perkin Elmer Clarus 400 gaschromatograph (Perkin Elmer, Rodgau, Germany) equipped with an Elite FFAP capillary column (30 m×0.25 mm, film thickness: 0.25 μm; Perkin Elmer, Rodgau, Germany) and a flame ionization detector (Perkin Elmer, Rodgau, Germany). 1 μL of the sample was analyzed after split injection (10 mL/min) and helium as carrier gas. The temperatures of the injector and detector were 200° C. and 250° C., respectively. The following temperature program was applied: 50° C. for 5 min, increase of 10° C./min to 120° C. (hold for 5 min), increase of 15° C./min to 180° C. (hold for 10 min), and increase of 20° C./min to 220° C. for 37 min.

1.8 Metabolite Analysis by HPLC

For quantification of glucose, ethanol, glycerol and acetate 450 μL cell-free samples were mixed with 50 μL of 50% (w/v) 5-sulfosalicylic acid, vigorously shaken and centrifuged (4° C., 5 min, 13 000 rcf). The supernatant was analyzed with an UHPLC+ system (Dionex UltiMate 3000, Thermo Scientific, Dreieich, Germany) equipped with a HyperREZ XP Carbohydrate H+ 8 μm column. To detect the substrates a refractive index detector (Thermo Shodex RI-101) was used. Separation was carried out at 65° C. with 5 mM sulfuric acid as mobile phase (flow rate of 0.6 ml/min). Five standards (mixtures of D-glucose, ethanol, glycerol and acetate with concentrations of 0.05-2% (w/v)) were analyzed for quantification of the different compounds.

1.9 Determination of Cell Density

The cell density in a liquid culture was measured with an Ultrospec 2100 pro spectrophotometer (GE Healthcare, USA) by determination of the optical density at 600 nm ($OD_{600}$).

2. Results

For the production of short FA in *S. cerevisiae*, a Δfas1 Δfas2 strain was created. Two heterozygotic strains with one deletion each, were mated and then sporulated to gain the double knockout strain. The two chains of FAS were transformed into cells on two separate low copy vectors (pRS315 and pRS313 respectively) under control of their natural promoters and terminators (Chirala 1992). The plasmid FAS system was then the only source of de-novo fatty acids.

2.1 Short FA Yield in YPD Supplemented with $C_{18:1}$

In some strains, growth was severely inhibited in regular YPD media, most likely because the plasmid FAS system did not produce enough long fatty acids necessary for cell growth. As an alternative, strains were also tested in YPD media supplemented with oleic acid ($C_{18:1}$, 1 mM) where all strains showed similar growth (Table 2). The reestablishment in growth is proof that an insufficient production of long chains prevented cells from growing before.

2.2 Vitality Parameters

In our in vivo study, the cells themselves were closely monitored. The cell density was measured for all samples at the end of the growing period and the wet cell pellet weight was noted (Table 2). In addition, for selected samples $OD_{600}$ was recorded at several time points (FIG. 3). For the growth in regular YPD, three groups can be distinguished: Strains that showed regular growth, ones with reduced growth and a group, were only an extremely low or no detectable growth could be seen. When the media was supplemented with $C_{18:1}$ (1 mM) all strains showed similar growth.

In order to test the theory, that reduced growth for the I306A-R130K-G236S-M237W mutant could derive from a strong initial production of $C_8$ eventually inhibiting further growth, product spectra of selected strains were measured after 12 h and 24 h in addition to the regular measurements after 48 h (FIG. 5). While cell density of the I306A-R130K-G236S-M237W mutant reached its stationary phase already after 24 h instead of a later time (as for the R130K mutant for example, FIG. 3), the FA production follows a similar pattern for both the samples.

TABLE 2

Cell density ($OD_{600}$ and wet pellet weight) after 48 h.

| | Samples in regular YPD | | Samples in YPD with $C_{18:1}$ | |
|---|---|---|---|---|
| | $OD_{600}$ | wet cell pellet (g) | $OD_{600}$ | wet cell pellet (g) |
| wild type | 24.7 | 1.1 | 17.4 | 1.3 |
| G236S | 21.9 | 1.1 | 19.2 | 1.4 |
| G236S M237W | 15.6 | 1.0 | 19.5 | 1.5 |
| I306A | 23.1 | 1.1 | 19.2 | 1.4 |
| I306A G236S M237W | 15.9 | 1.1 | 18.8 | 1.4 |
| R130K G236S M237W | 3.5 | 0.2 | 22.0 | 1.5 |
| I306A R130K G236S M237W | 5.4 | 0.5 | 20.4 | 1.7 |
| R130K | 20.7 | 1.1 | 24.1 | 1.4 |
| I306 R130K | 22.5 | 1.2 | 20.3 | 1.5 |
| I306A G236S | 15.6 | 1.3 | 18.9 | 1.4 |
| R130K G236S | 10.2 | 0.9 | 19.6 | 1.4 |
| I306A R130K G236S | 14.0 | 1.1 | 18.3 | 1.3 |
| G236S F265Y | 0.1 | 0.3 | 17.5 | 1.4 |
| I306A G236S F265Y | 0.3 | 0.3 | 16.7 | 1.3 |
| R130K G236S F265Y | 0.1 | 0.3 | 15.8 | 1.4 |
| I306A R130K G236S F265Y | 0.1 | 0.3 | 17.0 | 1.5 |
| I306A F265Y | 15.6 | 1.2 | 16.9 | 1.3 |
| I306A G236S M237W F265Y | —* | —* | 18.2 | 1.4 |
| I306A F265W | —* | —* | 17.7 | 1.3 |
| I306A G236S F265W | —* | —* | 21.8 | 1.4 |
| I306A G236S M237W F265W | —* | —* | 18.4 | 1.3 |
| I306A R130K F265Y | 4.3 | 0.6 | 21.1 | 1.4 |
| I306A R130K G236S M237W F265Y | —* | —* | 20.5 | 1.3 |
| I306A R130K F265W | —* | —* | 23.6 | 1.4 |
| I306A R130K G236S F265W | —* | —* | 15.8 | 1.4 |
| I306A R130K G236S M237W F265W | —* | —* | 21.1 | 1.3 |

Just before further processing, the $OD_{600}$ was measured for selected samples, both when they were grown in regular YPD and in YPD supplemented with $C_{18:1}$ (1 mM). For the growth in regular YPD, samples could be divided into three groups: regular growth (white background), reduced growth (light gray background) and very little/no growth (dark gray background). In YPD supplemented with $C_{18:1}$ all samples showed nearly the same densities. Also, the wet pellet weight was noted. It is, however, prone to errors since residual media that is stuck to the tube can make the results less reliable. For samples marked with an asterisk (*), no main culture was grown, after the preculture already showed no significant growth.

2.3 Glucose Consumption, Ethanol Production, FA Production on Ethanol

For cells grown with YPD media the glucose consumption and ethanol synthesis was measured. For all tested strains (FIG. 6) glucose is entirely consumed after 20 h, whereas the synthesis of ethanol starts after approx. 10 h, when a low glucose concentration (<1.2% (wt/vol)) is measurable. Corresponding to this, the amount of glycerol and acetate (FIG. 7) increases after 10 h of fermentation, which can be compared to the strain with the wild type FAS.

Example 2

1. Materials and Methods

For this example, materials and methods were the same as in Example 1, if not stated otherwise.

1.1 Vector Description

See Example 1. For constructs carrying any of the mutations Q193A, Q193E, N258A, N258D, D259A, the ADH2 promotor was used. For comparison, also one wild type construct was cloned with this promotor and used as a reference when constructs with this particular promotor were tested.

1.2 Primers

For the introduction of the point mutations in a PCR, the primers are listed below. The PCR products were then cloned into the vector containing the ADH2 promotor via homologous recombination. fw=forward, ry=reverse

```
FAS2-D259A_rv
                                            SEQ ID NO. 17
TCTTGTAAAATAGCATTTTGGACAGGCTCATCCTTGAAACGGTCCTTA
AAC

FAS2-D259A-fw
                                            SEQ ID NO. 18
CCTGTCCAAAATGCTATTTTACAAGAATCATTTATCAACACCATGTCC
GCTTGGG

FAS2-N258A rv
                                            SEQ ID NO. 19
TCTTGTAAAATATCAGCTTGGACAGGCTCATCCTTGAAACGGTCCTTAA
AC

FAS2-N258A fw
                                            SEQ ID NO. 20
CCTGTCCAAGCTGATATTTTACAAGAATCATTTATCAACACCATGTCCG
CTTGGG

FAS2_Q193A_rv
                                            SEQ ID NO. 21
GAATAATGTGATTGGGTCAACCGCAGAAATGATATCATCAGAGATACCA
TAAGTC

FAS2_Q193A _fw
                                            SEQ ID NO. 22
CTGCGGTTGACCCAATCACATTATTCGTTTTGGTCTCTGTTGTGGAAG

FAS2_Q193E rv
                                            SEQ ID NO. 23
GAATAATGTGATTGGGTCAACCTCAGAAATGATATCATCAGAGATACCA
TAAGTC

FAS2 Q193E_fw
                                            SEQ ID NO. 24
CTGAGGTTGACCCAATCACATTATTCGTTTTGGTCTCTGTTGTGGAAG
```

-continued
```
FAS2_N258D_rv
                                            SEQ ID NO. 25
TCTTGTAAAATATCATCTTGGACAGGCTCATCCTTGAAACGGTCCTTAA
AC FAS2_N258D_fw
                                            SEQ ID NO. 26
CCTGTCCAAGATGATATTTTACAAGAATCATTTATCAACACCATGTCCG
CTTGGG
```

The following primers were designed for homologous recombination of the cut vector and the ADH2 promotor.

```
pRS315-pADH2
                                            SEQ ID NO. 27
CAGTGAATTGTAATACGACTCACTATAGGGCGAATTGGAGCTGGCAAAAC
GTAGGGGCAAACAAACG pADH2-Fas2
                                            SEQ ID NO. 28
GCAAAATATGAGCTAATTCTTGCTCAACTTCCGGCTTCATTGTGTATTAC
GATATAGTTAATAG

Fas2-pADH2
                                            SEQ ID NO. 29
GCATACAATCAACTATCAACTATTAACTATATCGTAATACACAATGAAGC
CGGAAGTTGAGCAAGAATTAG pRS42_hxt7
                                            SEQ ID NO. 30
CACACAGGAAACAGCTATGAC
```

1.3 Cultures for Product Analysis

In contrast to the procedure described in Example 1, the main culture was buffered to pH 6.5 ((100 mM $K_2HPO_4$/$KH_2PO_4$). Cell cultivation was 72 hours.

The features disclosed in the foregoing description, in the claims and/or in the accompanying drawings may, both separately and in any combination thereof, be material for realizing the invention in diverse forms thereof.

REFERENCES

Aritomi K, et al. (2004) Self-cloning Yeast Strains Containing Novel <I>FAS2</I> Mutations Produce a Higher Amount of Ethyl Caproate in Japanese Sake TI. *Bioscience, Biotechnology, and Biochemistry* 68(1):206-214.

Beld J, Lee D J, & Burkart M D (2015) Fatty acid biosynthesis revisited: structure elucidation and metabolic engineering. *Molecular BioSystems* 11(1):38-59.

Bunkoczi G, et al. (2009) Structural Basis for Different Specificities of Acyltransferases Associated with the Human Cytosolic and Mitochondrial Fatty Acid Synthases. *Chemistry & Biology* 16(6):667-675.

Chirala S S (1992) Coordinated regulation and inositol-mediated and fatty acid-mediated repression of fatty acid synthase genes in *Saccharomyces cerevisiae*. *Proceedings of the National Academy of Sciences of the United States of America* 89(21):10232-10236.

Choi Y J & Lee S Y (2013) Microbial production of short-chain alkanes. *Nature* 502(7472):571-574.

Christensen C E, Kragelund B B, von Wettstein-Knowles P, & Henriksen A (2007) Structure of the human β-ketoacyl [ACP] synthase from the mitochondrial type II fatty acid synthase. *Protein Science* 16(2):261-272.

Grininger M (2014) Perspectives on the evolution, assembly and conformational dynamics of fatty acid synthase type I (FAS I) systems. *Current Opinion in Structural Biology* 25(0):49-56.

Hitchman T S, et al. (2001) Hexanoate Synthase, a Specialized Type I Fatty Acid Synthase in Aflatoxin B1 Biosynthesis. *Bioorganic Chemistry* 29(5):293-307.

Ichihara Ki & Fukubayashi Y (2010) Preparation of fatty acid methyl esters for gas-liquid chromatography. *Journal of Lipid Research* 51(3):635-640.

Jenni S, et al. (2007) Structure of Fungal Fatty Acid Synthase and Implications for Iterative Substrate Shuttling. *Science* 316(5822):254-261.

Johansson P, et al. (2008) Inhibition of the fungal fatty acid synthase type I multienzyme complex. *Proceedings of the National Academy of Sciences* 105(35):12803-12808.

Kawaguchi A, Arai K, Seyama Y, Yamakawa T, & Okuda S (1980) Substrate Control of Termination of Fatty Acid Biosynthesis by Fatty Acid Synthetase from *Brevibacterium ammoniagenes* TI. *The Journal of Biochemistry* 88(2):303-306.

Knight M J, Bull I D, & Cumow P (2014) The yeast enzyme Eht1 is an octanoyl-CoA:ethanol acyltransferase that also functions as a thioesterase. *Yeast* 31(12):463-474.

Leber C & Da Silva N A (2014) Engineering of *Saccharomyces cerevisiae* for the synthesis of short chain fatty acids. *Biotechnology and Bioengineering* 111(2):347-358.

Leber C, Polson B, Fernandez-Moya R, & Da Silva N A (2015) Overproduction and secretion of free fatty acids through disrupted neutral lipid recycle in *Saccharomyces cerevisiae*. *Metabolic Engineering* 28(0):54-62.

Leibundgut M, Jenni S, Frick C, & Ban N (2007) Structural Basis for Substrate Delivery by Acyl Carrier Protein in the Yeast Fatty Acid Synthase. *Science* 316(5822):288-290.

Liu H, et al. (2012) Production of extracellular fatty acid using engineered *Escherichia coli*. *Microbial Cell Factories* 11.

Peralta-Yahya, P. P., Zhang, F., del Cardayre, S. B. & Keasling, J. D. (2012) Microbial engineering for the production of advanced biofuels. *Nature* 488: 320-328.

Runguphan W & Keasling J D (2014) Metabolic engineering of *Saccharomyces cerevisiae* for production of fatty acid-derived biofuels and chemicals. *Metabolic Engineering* 21(0):103-113.

Schiestl R & Gietz R D (1989) High efficiency transformation of intact yeast cells using single stranded nucleic acids as a carrier. *Curr Genet* 16(5-6):339-346.

Sikorski R S & Hieter P (1989) A System of Shuttle Vectors and Yeast Host Strains Designed for Efficient Manipulation of DNA in *Saccharomyces Cerevisiae*. *Genetics* 122(1):19-27.

Tehlivets O, Scheuringer K, & Kohlwein S D (2007) Fatty acid synthesis and elongation in yeast. *Regulation of Lipid Metabolism in Yeast* 1771(3):255-270.

Zhang L, Joshi A K, Hofmann J, Schweizer E, & Smith S (2005) Cloning, Expression, and Characterization of the Human Mitochondrial β-Ketoacyl Synthase: COMPLEMENTATION OF THE YEAST CEM1 KNOCK-OUT STRAIN. *Journal of Biological Chemistry* 280(13): 12422-12429.

---

The invention claimed is:

1. A fatty acid synthase (FAS) comprising two polypeptide subunits having the sequences of S. cerevisiae FAS1 and FAS2 which comprise one to eight amino acid substitutions, wherein at least one of said amino acid substitutions is an amino acid substitution in a position corresponding to R130 of the amino acid sequence of SEQ ID NO: 1, and wherein the fatty acid synthase causes elevated overall production of short fatty acids, CoA esters of short fatty acids, ethyl esters of short fatty acids, esters of short fatty acids with other metabolites, and/or enzyme bound short fatty acids ($C_6$ to $C_{12}$) compared to the wild type protein(s) or the protein(s) without such amino acid substitution(s).

2. The fatty acid synthase according to claim 1, selected from the group of:
a protein comprising the amino acid substitutions I306A, R130K and F265Y;
a protein comprising the amino acid substitutions I306A, R130K and G236S;
a protein comprising the amino acid substitution R130K;
a protein comprising the amino acid substitutions I306A, R130K, G236S and M237W;
a protein comprising the amino acid substitutions I306A and R130K;
a protein comprising the amino acid substitutions R130K and G236S;
a protein comprising the amino acid substitutions R130K, G236S and M237W;
a protein comprising the amino acid substitutions R130K, G236S and F265Y;
a protein comprising the amino acid substitutions I306A, R130K, G236S and F265Y;
a protein comprising the amino acid substitutions R130K and M237W;
a protein comprising the amino acid substitutions R130K and F265Y;
a protein comprising the amino acid substitutions I306A, R130K and M237W;
a protein comprising the amino acid substitutions R130K, M237W and F265Y;
a protein comprising the amino acid substitutions I306A, R130K, M237W and F265Y;
a protein comprising the amino acid substitutions R130K, G236S, M237W and F265Y;
a protein comprising the amino acid substitutions I306A, R130K, G236S, M237W and F265Y;
a protein comprising the amino acid substitutions I306A, R130K, G236S and D259A;
a protein comprising the amino acid substitutions I306A, R130K, G236S, M237W and D259A;
a protein comprising the amino acid substitutions I306A, R130K, G236S and N258A;
a protein comprising the amino acid substitutions I306A, R130K, G236S, M237W and N258A;
a protein comprising the amino acid substitutions I306A, R130K, G236S and N258D;
a protein comprising the amino acid substitutions I306A, R130K, G236S, M237W and N258D;
a protein comprising the amino acid substitutions I306A, R130K, G236S and Q193A;
a protein comprising the amino acid substitutions I306A, R130K, G236S, M237W and Q193A;
a protein comprising the amino acid substitutions I306A, R130K, G236S and Q193E; and
a protein comprising the amino acid substitutions I306A, R130K, G236S, M237W and Q193E;
wherein
R130K refers to R130K in the amino acid sequence of SEQ ID NO: 1;
I306A refers to I306A in the amino acid sequence of SEQ ID NO: 2;
G236S refers to G236S in the amino acid sequence of SEQ ID NO: 3;
M237W refers to M237W in the amino acid sequence of SEQ ID NO: 3;
F265Y refers to F265Y in the amino acid sequence of SEQ ID NO: 3;
D259A refers to D259A in the amino acid sequence of SEQ ID NO: 3;
N258A refers to N258A in the amino acid sequence of SEQ ID NO: 3;
N258D refers to N258D in the amino acid sequence of SEQ ID NO: 3;
Q193A refers to Q193A in the amino acid sequence of SEQ ID NO: 3; and
Q193E refers to Q193E in the amino acid sequence of SEQ ID NO: 3.

3. The fatty acid synthase according to claim 1, selected from:
variant I306A/R130K/F265Y;
variant I306A/R130K/G236S;
variant R130K;
variant I306A/R130K/G236S/M237W;
variant I306A/R130K;
variant R130K/G236S;
variant R130K/G236S/M237W;
variant R130K/G236S/F265Y;
variant I306A/R130K/G236S/F265Y;
variant R130K/M237W;
variant R130K/F265Y;
variant I306A/R130K/M237W;
variant R130K/M237W/F265Y;
variant I306A/R130K/M237W/F265Y;
variant R130K/G236S/M237W/F265Y;
variant I306A/R130K/G236S/M237W/F265Y;
variant I306A/R130K/G236S/D259A;

variant I306A/R130K/G236S/M237W/D259A;
variant I306A/R130K/G236S/N258A;
variant I306A/R130K/G236S/M237W/N258A;
variant I306A/R130K/G236S/N258D;
variant I306A/R130K/G236S/M237W/N258D;
variant I306A/R130K/G236S/Q193A;
variant I306A/R130K/G236S/M237W/Q193A;
variant I306A/R130K/G236S/Q193E; and
variant I306A/R130K/G236S/M237W/Q193E;
wherein
R130K refers to R130K in the amino acid sequence of SEQ ID NO: 1;
I306A refers to I306A in the amino acid sequence of SEQ ID NO: 2;
G236S refers to G236S in the amino acid sequence of SEQ ID NO: 3;
M237W refers to M237W in the amino acid sequence of SEQ ID NO: 3; F265Y refers to F265Y in the amino acid sequence of SEQ ID NO: 3;
D259A refers to D259A in the amino acid sequence of SEQ ID NO: 3;
N258A refers to N258A in the amino acid sequence of SEQ ID NO: 3;
N258D refers to N258D in the amino acid sequence of SEQ ID NO: 3;
Q193A refers to Q193A in the amino acid sequence of SEQ ID NO: 3; and
Q193E refers to Q193E in the amino acid sequence of SEQ ID NO: 3.

4. The fatty acid synthase according to claim 1, wherein the amino acid substitution(s) selected from:
I306A, R130K and F265Y;
R130K;
I306A, R130K, G236S and M237W;
R130K and G236S;
I306A and R130K;
I306A, R130K and G236S;
R130K, G236S and M237W;
R130K, G236S and F265Y;
I306A, R130K, G236S and F265Y;
R130K and M237W;
R130K and F265Y;
I306A, R130K and M237W;
R130K, M237W and F265Y;
I306A, R130K, M237W and F265Y;
R130K, G236S, M237W and F265Y;
I306A, R130K, G236S, M237W and F265Y;
I306A, R130K, G236S and D259A,
I306A, R130K, G236S and N258A;
I306A, R130K, G236S and N258D;
I306A, R130K, G236S and Q193A;
I306A, R130K, G236S and Q193E;
I306A, R130K, G236S, M237W and D259A;
I306A, R130K, G236S, M237W and N258A;
I306A, R130K, G236S, M237W and N258D;
I306A, R130K, G236S, M237W and Q193A; and
I306A, R130K, G236S, M237W and Q193E;
wherein
R130K refers to R130K in the amino acid sequence of SEQ ID NO: 1;
I306A refers to I306A in the amino acid sequence of SEQ ID NO: 2;
G236S refers to G236S in the amino acid sequence of SEQ ID NO: 3;
M237W refers to M237W in the amino acid sequence of SEQ ID NO: 3; F265Y refers to F265Y in the amino acid sequence of SEQ ID NO: 3;
D259A refers to D259A in the amino acid sequence of SEQ ID NO: 3;
N258A refers to N258A in the amino acid sequence of SEQ ID NO: 3;
N258D refers to N258D in the amino acid sequence of SEQ ID NO: 3;
Q193A refers to Q193A in the amino acid sequence of SEQ ID NO: 3; and
Q193E refers to Q193E in the amino acid sequence of SEQ ID NO: 3;
increase(s) the selectivity for the production of $C_8$ fatty acids, $C_8$ fatty acid CoA esters, $C_8$ fatty acid ethyl esters, $C_8$ fatty acid esters with other metabolites, and/or enzyme bound $C_8$ fatty acids compared to wild type protein(s) or the protein without such amino acid substitution(s).

* * * * *